(12) United States Patent
Dambacher et al.

(10) Patent No.: US 12,344,890 B2
(45) Date of Patent: *Jul. 1, 2025

(54) PROCESS FOR COGNATE NUCLEOTIDE DETECTION IN A NUCLEIC ACID SEQUENCING WORKFLOW

(71) Applicant: Omniome, Inc., San Diego, CA (US)

(72) Inventors: Corey M. Dambacher, La Jolla, CA (US); Joseph Rokicki, San Diego, CA (US); Keunho Ahn, San Diego, CA (US); Brittany Ann Rohrman, San Diego, CA (US); Michael Nguyen, San Diego, CA (US); Kandaswamy Vijayan, San Diego, CA (US)

(73) Assignee: PACIFIC BIOSCIENCES OF CALIFORNIA, INC., Menlo Park, CA (US)

( * ) Notice: Subject to any disclaimer, the term of this patent is extended or adjusted under 35 U.S.C. 154(b) by 967 days.

This patent is subject to a terminal disclaimer.

(21) Appl. No.: 17/190,894

(22) Filed: Mar. 3, 2021

(65) Prior Publication Data

US 2021/0340612 A1    Nov. 4, 2021

Related U.S. Application Data

(63) Continuation of application No. 15/873,343, filed on Jan. 17, 2018, now Pat. No. 10,975,427.

(60) Provisional application No. 62/574,308, filed on Oct. 19, 2017, provisional application No. 62/506,759, filed on May 16, 2017, provisional application No. 62/450,397, filed on Jan. 25, 2017, provisional application No. 62/448,839, filed on Jan. 20, 2017.

(51) Int. Cl.

| | | |
|---|---|---|
| *C12Q 1/68* | (2018.01) | |
| *C07H 21/02* | (2006.01) | |
| *C07H 21/04* | (2006.01) | |
| *C07H 99/00* | (2006.01) | |
| *C12Q 1/6806* | (2018.01) | |
| *C12Q 1/6869* | (2018.01) | |
| *C12Q 1/6874* | (2018.01) | |
| *C12N 9/12* | (2006.01) | |

(52) U.S. Cl.
CPC .......... *C12Q 1/6869* (2013.01); *C07H 21/02* (2013.01); *C07H 21/04* (2013.01); *C07H 99/00* (2013.01); *C12Q 1/6806* (2013.01); *C12Q 1/6874* (2013.01); *C12N 9/1241* (2013.01)

(58) Field of Classification Search
None
See application file for complete search history.

(56) References Cited

U.S. PATENT DOCUMENTS

| | | |
|---|---|---|
| 5,302,509 A | 4/1994 | Cheeseman |
| 5,614,365 A | 3/1997 | Tabor et al. |
| 6,485,909 B1 | 11/2002 | Hong et al. |
| 6,720,177 B2 | 4/2004 | Ghadiri et al. |
| 6,828,094 B2 | 12/2004 | Kilger et al. |
| 6,828,159 B1 | 12/2004 | Drexhage et al. |
| 6,908,736 B1 | 6/2005 | Densham |
| 7,008,766 B1 | 3/2006 | Densham |
| 7,008,798 B2 | 3/2006 | Waggoner |
| 7,223,540 B2 | 5/2007 | Pourmand et al. |
| 7,264,934 B2 | 9/2007 | Fuller |
| 7,329,492 B2 | 2/2008 | Hardin et al. |
| 7,449,297 B2 | 11/2008 | Freije et al. |
| 7,482,120 B2 | 1/2009 | Buzby |
| 7,604,963 B2 | 10/2009 | Densham |
| 7,635,578 B2 | 12/2009 | Ju et al. |
| 7,713,698 B2 | 5/2010 | Ju et al. |
| 7,790,869 B2 | 9/2010 | Ju et al. |
| 7,871,771 B2 | 1/2011 | Fuller et al. |
| 7,939,264 B1 | 5/2011 | Densham |
| 8,071,755 B2 | 12/2011 | Efcavitch et al. |
| 8,088,575 B2 | 1/2012 | Ju et al. |
| 8,133,672 B2 | 3/2012 | Bjornson et al. |
| 8,236,532 B2 | 8/2012 | Ronaghi et al. |
| 8,298,792 B2 | 10/2012 | Ju et al. |
| 8,399,196 B2 | 3/2013 | Hoser |

(Continued)

FOREIGN PATENT DOCUMENTS

| | | |
|---|---|---|
| EP | 1115848 A1 | 7/2001 |
| WO | 1990013666 A1 | 11/1990 |

(Continued)

OTHER PUBLICATIONS

EP18709165.7, "Office Action", Jan. 16, 2023, 8 pages.
U.S. Appl. No. 16/164,417, "Non-Final Office Action", Apr. 4, 2021, 16 pages.
"APCH231: Chemical Analysis Complexometric Titrations EDTA", Notes compiled by Dr. C. Southway, Available Online At: (http://cheminnerweb.ukzn.ac.za/libraries/apch231_h_govender_s_notes/apch231_edta.sflb.ashx), post date of Nov. 23, 2015, pp. 30-42.
"Ion Torrent Amplicon Sequencing", Application Note Amplicon Sequencing, Available Online at http://www.iontorrent.com/lib/images/PDFs/amplicon_application_note_040411.pdf, XP-002681382, Apr. 4, 2011, 5 pages.

(Continued)

*Primary Examiner* — Stephanie K Mummert
(74) *Attorney, Agent, or Firm* — Kilpatrick Townsend & Stockton LLP

(57) ABSTRACT

Method and composition for identifying cognate nucleotides in a Sequencing By Binding™ procedure, wherein one or more labeled nucleotides are detected in ternary complexes but never incorporated. Labeled nucleotides can be incorporable nucleotides that contact preformed blocked primed template nucleic acids. Alternatively, labeled nucleotides are labeled non-incorporable nucleotides. Labeled nucleotides, including labeled non-incorporable nucleotides, can be detected in ternary complexes in the same reaction mixture that incorporates a reversible terminator nucleotide to create a blocked primed template nucleic acid. Detection of ternary complexes can take place in the presence of a catalytic metal ion.

15 Claims, 7 Drawing Sheets

(56) References Cited

U.S. PATENT DOCUMENTS

| | | | |
|---|---|---|---|
| 8,481,266 | B2 | 7/2013 | Shao et al. |
| 8,535,881 | B2 | 9/2013 | Schneider |
| 8,603,741 | B2 | 12/2013 | Emig et al. |
| 8,632,975 | B2 | 1/2014 | Vander Horn et al. |
| 8,658,365 | B2 | 2/2014 | Bjornson et al. |
| 8,703,461 | B2 | 4/2014 | Peris et al. |
| 8,911,972 | B2 | 12/2014 | Chaisson et al. |
| 8,986,930 | B2 | 3/2015 | Fedorov et al. |
| 9,255,258 | B2 | 2/2016 | Vander Horn et al. |
| 9,279,155 | B2 | 3/2016 | Bjornson et al. |
| 9,279,154 | B2 | 6/2016 | Previte et al. |
| 9,651,490 | B2 | 5/2017 | Zilles et al. |
| 10,294,514 | B2* | 5/2019 | Iyidogan ............... C12Q 1/6848 |
| 10,443,098 | B2* | 10/2019 | Vijayan .................. G01N 33/50 |
| 10,975,427 | B2* | 4/2021 | Dambacher .......... C12Q 1/6806 |
| 2004/0096853 | A1 | 5/2004 | Mayer |
| 2006/0292583 | A1 | 12/2006 | Schneider et al. |
| 2007/0009925 | A1 | 1/2007 | Fang et al. |
| 2007/0148645 | A1 | 6/2007 | Hoser |
| 2009/0061447 | A1 | 3/2009 | Schneider |
| 2010/0316999 | A1 | 12/2010 | Densham |
| 2010/0317012 | A1 | 12/2010 | Ju et al. |
| 2011/0008794 | A1 | 1/2011 | Schneider |
| 2011/0237464 | A1 | 9/2011 | Cunningham et al. |
| 2013/0165328 | A1 | 6/2013 | Previte et al. |
| 2014/0127680 | A1 | 5/2014 | Emig et al. |
| 2014/0234940 | A1 | 8/2014 | Peris et al. |
| 2015/0337366 | A1 | 11/2015 | Davis et al. |
| 2016/0010150 | A1 | 1/2016 | Emig et al. |
| 2016/0168633 | A1 | 6/2016 | Previte et al. |
| 2016/0177384 | A1 | 6/2016 | Bjornson et al. |
| 2016/0208318 | A1* | 7/2016 | Vander Horn ....... C12Q 1/6872 |
| 2017/0022553 | A1 | 1/2017 | Vijayan et al. |
| 2017/0191125 | A1 | 7/2017 | Vijayan et al. |
| 2017/0314064 | A1 | 11/2017 | Iyidogan et al. |
| 2017/0314072 | A1 | 11/2017 | Vijayan et al. |
| 2018/0044727 | A1 | 2/2018 | Vijayan et al. |
| 2018/0187245 | A1 | 7/2018 | Dambacher et al. |
| 2018/0208983 | A1 | 7/2018 | Dambacher et al. |

FOREIGN PATENT DOCUMENTS

| | | | |
|---|---|---|---|
| WO | 0116375 | A2 | 3/2001 |
| WO | 0204680 | A2 | 1/2002 |
| WO | 2005121363 | A2 | 12/2005 |
| WO | 2009/145828 | A2 | 12/2009 |
| WO | 2009145820 | A2 | 12/2009 |
| WO | 2010068884 | A2 | 6/2010 |
| WO | 2010111690 | A2 | 9/2010 |
| WO | 2011159942 | A1 | 12/2011 |
| WO | 2012166742 | A3 | 12/2012 |
| WO | 2013096692 | A1 | 6/2013 |
| WO | 2014114665 | A1 | 7/2014 |
| WO | 2016001963 | A1 | 1/2016 |
| WO | 2017014762 | A1 | 1/2017 |
| WO | 2017190012 | A1 | 11/2017 |
| WO | 2018034780 | A1 | 2/2018 |
| WO | 2018035134 | A1 | 2/2018 |
| WO | 2018136487 | A1 | 7/2018 |

OTHER PUBLICATIONS

U.S. Appl. No. 15/873,343, "Final Office Action", Aug. 6, 2020, 11 pages.

U.S. Appl. No. 15/873,343, "Non-Final Office Action", Mar. 20, 2020, 11 pages.

U.S. Appl. No. 15/873,343, "Non-Final Office Action", Oct. 21, 2019, 11 pages.

U.S. Appl. No. 15/873,343, "Notice of Allowance", Dec. 7, 2020, 7 pages.

Agnarsson et al., "On-Chip Modulation of Evanescent Illumination and Live-Cell Imaging With Polymer Waveguides.", Optics Express, vol. 19, Issue No. 23, Nov. 7, 2011, pp. 22929-22935.

Anker et al., "Biosensing with Plasmonic Nanosensors", Nature Materials, vol. 7, Issue No. 6, Jun. 2008, pp. 442-453.

Anonymous, "5-Propargytamino-ddUTP Cy5", Available online at https://www.jenabioscience.com/images/PDF/NU-1619-CY5.pdf, Mar. 15, 2018, 1 page.

AU2018210944, "First Examination Report", Jan. 25, 2021, 4 pages.

Bandwar et al., "Peculiar 2-Aminopurine Fluorescence Monitors the Dynamics of Open Complex Formation by Bacteriophage T7 RNA Polymerase", The Journal of Biological Chemistry, vol. 275, No. 17, Apr. 27, 2001, pp. 14075-14082.

Brockman et al., "A Multistep Chemical Modification Procedure to Create DNA Arrays on Gold Surfaces for the Study of Protein-DNA Interactions with Surface Plasmon Resonance Imaging", Journal of the American Chemical Society, vol. 121, Aug. 19, 1999, pp. 8044-8051.

Brown et al., "Pre-Steady-State Kinetic Analysis of Truncated and Full-Length Saccharomyces Cerevisiae DNA Polymerase Eta", Journal of Nucleic Acids, vol. 2010, Article ID 871939, Jul. 25, 2010, 11 pages.

CA3,050,695, "Office Action", Jul. 31, 2020, 5 pages.

Campagnola et al., "High-Throughput Screening Identification of Poliovirus RNA-Dependent RNA Polymerase Inhibitors", Antiviral Res., vol. 91, No. 3, Sep. 2011, pp. 241-251.

Chan et al., "A General Method for Discovering Inhibitors of Protein-DNA Interactions Using Photonic Crystal Biosensors", ACS Chem Biol, vol. 3, No. 7, Jul. 18, 2008, pp. 437-448.

Chen et al., "The History and Advances of Reversible Terminators Used in New Generations of Sequencing Technology", Genomics Proteomics Bioinformatics, vol. 11, No. 1, Feb. 1, 2013, pp. 34-40.

Chin et al., "The Effect of Divalent Nickel (Ni2+) on in Vivo DNA Replication by DNA Polymerase α1", Cancer Research, vol. 54, May 1, 1994, pp. 2337-2341.

Choi et al., "EML4-ALK Mutations in Lung Cancer that Confer Resistance to ALK Inhibitors", The New England Journal of Medicine, vol. 18, Oct. 28, 2010, pp. 1734-1739.

Concepcion et al., "Label-Free Detection of Biomolecular Interactions Using BioLayer Interferometry for Kinetic Characterization", Combinatorial Chemistry and High Throughput Screening, vol. 12, No. 8, Sep. 2009, pp. 791-800.

Crumpacker, "Mechanism of Action of Foscarnet Against Viral Polymerase", American Journal of Medicine, vol. 92, No. 2, Supplement 2A, Feb. 14, 1992, pp. 2A-3S-2A-7S.

Datta et al., "Salt Dependence of DNA binding by Thermus Aquaticus and *Escherichia coli* DNA Polymerases", Journal of Biological Chemistry, vol. 278, No. 8, Feb. 21, 2003, pp. 5694-5701.

Deredge et al., "The Glutamate Effect on DNA Binding by Pol I DNA Polymerases: Osmotic Stress and the Effective Reversal of Salt Linkage", Journal of Molecular Biology, vol. 401, No. 2, Aug. 13, 2010, pp. 223-238.

Doublie et al., "An Open and Closed Case for All Polymerases", Structure, vol. 7, No. 2, Feb. 1999, pp. R31-R35.

Dunlap et al., "Use of 2-Aminopurine and Tryptophan Fluorescence as Probes in Kinetic Analyses of DNA Polymerase Beta", Biochemistry, vol. 41, No. 37, Sep. 17, 2002, pp. 11226-11235.

Dzantiev et al., "A Conformational Change in *E. coli* DNA Polymerase I (Klenow Fragment) Is Induced in the Presence of a dNTP Complementary to the Template Base in the Active Site", Biochemistry, vol. 39, No. 2, Jan. 18, 2000, pp. 356-361.

Engtrom et al., "A Label-Free Continuous Total-Internal-Reflection-Fluorescence-Based Immunosensor", Analytical Biochemistry, vol. 357, No. 2, Oct. 15, 2006, pp. 159-166.

EP18709165.7, "Office Action", Oct. 16, 2020, 6 pages.

Eriksson et al., "Pyrophosphate Analogues as Inhibitors of DNA Polymerases of Cytomegalovirus, Herpes Simplex Virus and Cellular Origin", Biochimica et Biophysica Acta, vol. 696, No. 2, Feb. 26, 1982, pp. 115-123.

Escobedo et al., "Integrated Nanohole Array Surface Plasmon Resonance Sensing Device Using a Dual-Wavelength Source", Journal of Micromechanics and Microengineering, vol. 21, No. 11, Oct. 2011, pp. 1-6.

(56) References Cited

OTHER PUBLICATIONS

Espinoza-Herrera et al., "Following DNA Chain Extension and Protein Conformational Changes in Crystals of a Y-Family DNA Polymerase via Raman Crystallography", Biochemistry, vol. 52, No. 29, Jul. 23, 2013, 22 pages.
Fang et al., "Genome-Wide Mapping of Methylated Adenine Residues in Pathogenic *Escherichia coli* Using Single-Molecule Real-Time Sequencing", Nature Biotechnology, vol. 30, No. 12, Dec. 2012, pp. 1232-1243.
Favicchio et al., "Fluorescence Spectroscopy and Anisotropy in the Analysis of DNA-Protein Interactions", Methods in Molecular Biology, vol. 543, Feb. 2009, pp. 589-611.
Federley, "New Insights Into the Mechanism of DNA Replication on Unmodified and Benzo[a]pyrene Modified Templates Using Surface Plasmon Resonance", Wayne State University Dissertations, Paper 235., Jan. 2011, 208 pages.
Fuller et al., "The Challenges of Sequencing by Synthesis", Nature Biotechnology, vol. 27, No. 11, Nov. 2009, pp. 1013-1023.
Gralla et al., "Potassium Glutamate As A Transcriptional Inhibitor During Bacterial Osmoregulation", The EMBO Journal, vol. 25, No. 7, Apr. 5, 2006, pp. 1515-1521.
Horn et al., "EML4-ALK: Honing In on a New Target in Non-Small-Cell Lung Cancer", Journal of Clinical Oncology, vol. 27, No. 26, Sep. 10, 2009, pp. 4232-4235.
Hoshino et al., "Effect of Ultrasound on DNA Polymerase Reactions: Monitoring on a 27-MHz Quartz Crystal Microbalance", Biomacromolecules, vol. 7, No. 3, Mar. 2006, pp. 682-685.
Hutter et al., "Labeled Nucleoside Triphosphates with Reversibly Terminating Aminoalkoxyl Groups", Nucleosides, Nucleotides and Nucleic Acids, vol. 29, No. 11-12, Nov. 2010, pp. 879-895.
Jindal et al., "Suramin Affects DNA Synthesis in HeLa Cells by Inhibition of DNA Polymerases", Cancer Research, vol. 50, Dec. 15, 1990, pp. 7754-7757.
Jochmans et al., "Indolopyridones Inhibit Human Immunodeficiency Virus Reverse Transcriptase with a Novel Mechanism of Action", Journal of Virology, vol. 80, No. 24, Dec. 2006, pp. 12283-12292.
Kaplan et al., "Photolabile Chelators for the Rapid Photorelease of Divalent Cations", Proc. Natl. Acad. Sci., vol. 85, Sep. 1988, pp. 6571-6575.
Kaushik et al., "Biochemical Analysis of Catalytically Crucial Aspartate Mutants of Human Immunodeficiency Virus Type 1 Reverse Transcriptase", Biochemistry, vol. 35, No. 36, Sep. 10, 1996, pp. 11536-11546.
Kim, "An FET-type Charge Sensor for Highly Sensitive Detection of DNA Sequence", Biosensors and Bioelectronics, vol. 20, No. 1, Jul. 30, 2004, pp. 69-74.
Klenow et al., "Effect of Monovalent Cations on the Activity of the DNA Polymerase of *Escherichia coli* B", European J. Biochem., vol. 9, 1969, pp. 133-141.
Kumar et al., "Altered Order of Substrate Binding by DNA Polymerase X from African Swine Fever Virus", Biochemistry, vol. 47, 2008, pp. 7875-7887.
Leinbach et al., "Mechanism of Phosphonoacetate Inhibition of Herpesvirus-Induced DNA Polymerase", Biochemistry, vol. 15, No. 2, 1976, pp. 426-430.
Livak et al., "Detection of Single Base Differences Using Biotinylated Nucleotides With Very Long Linker Arms", Nucleic Acids Research, vol. 20, Issue No. 18, 1992, pp. 4831-4837.
Lutz et al., "An in Vitro Screening Technique for DNA Polymerases that can Incorporate Modified Nucleotides. Pseudothymidine as a Substrate for Thermostable Polymerases", Nucleic Acids Research, vol. 27, No. 13, 1999, pp. 2792-2798.
Maga et al., "HIV-1 RT Inhibitors with a Novel Mechanism of Action: NNRTIs that Compete with the Nucleotide Substrate", Viruses, vol. 2, No. 4, 2010, pp. 880-899.
Maga et al., "Selective Interaction of the Human Immunodeficiency Virus Type 1 Reverse Transcriptase Nonnucleoside Inhibitor Efavirenz and Its Thio-Substituted Analog with Different Enzyme-Substrate Complexes", Antimicrobial Agents and Chemotherapy, vol. 44, No. 5, May 2000, pp. 1186-1194.
Mano, "Non-Solid Oncogenes in Solid Tumors: EML4-ALK Fusion Genes in Lung Cancer", Cancer Sci., vol. 99, No. 12, Dec. 2008, pp. 2349-2355.
Markiewicz et al., "Single-Molecule Microscopy Reveals New Insights into Nucleotide Selection by DNA Polymerase I", Nucleic Acids Research, vol. 40, No. 16, Jun. 4, 2012, pp. 7975-7984.
Masheyekhi et al., "Analysis of Read-Length Limiting Factors in Pyrosequencing Chemistry", Anal Biochem, vol. 363, Issue 3, Apr. 15, 2007, pp. 275-287.
Maxwell et al., "DNA Lesion Alters Global Conformational Dynamics of Y-family DNA Polymerase During Catalysis", The Journal of Biological Chemistry, vol. 287, No. 16, Apr. 13, 2012, pp. 13040-13047.
Nakano et al., "The Structural Stability and Catalytic Activity of DNA and RNA Oligonucleotides in the Presence of Organic Solvents", Biophysical Reviews, vol. 8, Issue No. 1, Jan. 11, 2016, pp. 11-23.
Namasivayam, "Light-Induced Molecular Cutting: Localized Reaction on a Single DNA Molecule", Anal. Chem., vol. 75, No. 16, Aug. 15, 2003, pp. 4118-4194.
Nath et al., "Label Free Colorimetric Biosensing Using Nanoparticles", Journal of Fluorescence, vol. 14, No. 4, Jul. 2004, pp. 377-389.
Nazirizadeh et al., "Low-Cost Label-Free Biosensors Using Photonic Crystals Embedded Between Crossed Polarizers", Optics Express, vol. 18, No. 18, Aug. 30, 2010, pp. 19120-19128.
Nikiforov, "Oligonucleotides Labeled With Single Fluorophores as Sensors for Deoxynucleotide Triphosphate Binding by DNA Polymerases", Analytical Biochemistry, vol. 444, 2014, pp. 60-66.
Patel, "Insights into DNA Polymerization Mechanisms from Structure and Function Analysis of HIV-1 Reverse Transcriptase", Biochemistry, vol. 34, 1995, pp. 5351-5363.
PCT/US2018/014005, "International Preliminary Report on Patentability", Aug. 1, 2019, 11 pages.
PCT/US2018/014005, "International Search Report and Written Opinion", Apr. 18, 2018, 15 pages.
PCT/US2018/056507, "International Preliminary Report on Patentability", Apr. 30, 2020, 9 pages.
PCT/US2018/056507, "International Search Report and Written Opinion", Dec. 13, 2018, 13 pages.
Peletskaya et al., "Cross-Linking of the Fingers Subdomain of Human Immunodeficiency Virus Type 1 Reverse Transcriptase to Template-Primer", Journal of Virology, vol. 75, No. 19, Oct. 2001, pp. 9435-9445.
Pitta et al., "Synthesis and HIV-1 RT Inhibitory Action of Novel (4/6-substituted Benzo[d]thiazol-2-yl) Thiazolidin-4-ones. Divergence From the Non-competitive Inhibition Mechanism", Journal of Enzyme Inhibition and Medicinal Chemistry, vol. 28, No. 1, 2013, pp. 113-122.
Potapova et al., "Interaction of dNTP, Pyrophosphate and their Analogs With the dNTP-binding Sites of *E. coli* DNA Polymerase I Klenow Fragment and Human DNA Polymerase", FEBS Letters, vol. 277, Nos. 1-2, Dec. 1990, pp. 194-196.
Puttaswamy, "Optical Method for Measuring Spatial pH Change on Conductive Microelectrodes", Submitted in fulfillment for the International Master's Program (IMP) Nanomaterials and Nanotechnology, KTH, Royal Institute of Technology, Stockholm, Sweden, 2007, pp. 1-66.
Ren et al., "Inhibition of Klenow DNA Polymerase and Poly(a)-Specific Ribonuclease by Aminoglycosides", RNA, vol. 8, 2002, pp. 1393-1400.
Richard et al., "Thermal Stability Landscape for Klenow DNA Polymerase as a Function of pH and Salt Concentration", Biochimica et Biophysica Acta, vol. 1764, 2006, pp. 1546-1552.
Roettger et al., "Mismatched and Matched dNTP Incorporation by DNA Polymerase β Proceed via Analogues Kinetic Pathways", Biochemistry, vol. 47, No. 37, 2008, pp. 9718-9727.
Santoso et al., "Conformational Transitions in DNA Polymerase I Revealed by Single-Molecule Fret", Proceedings of the National Academy of Sciences, vol. 107, No. 2, Jan. 12, 2010, pp. 715-720.

(56) References Cited

OTHER PUBLICATIONS

Schadt et al., "Modeling Kinetic Rate Variation in Third Generation DNA Sequencing Data to Detect Putative Modifications to DNA Bases", Genome Research, vol. 23, No. 1, Jan. 2013, pp. 129-141.
Schultz et al., "Single-Target Molecule Detection With Nonbleaching Multicolor Optical Immunolabels", PNAS, vol. 96, Issue No. 3, Feb. 1, 2000, pp. 996-1001.
Sen et al., "Intrinsic Fluorescence of *E. coli* RNA Polymerase as a Probe for Its Conformational Changes During Transcription Initiation", Biochem Biophys Res Commun, vol. 201, No. 2, Jun. 15, 1994, pp. 820-828.
Soda et al., "Identification of the Transforming EML4-ALK Fusion Gene in Non-Small-Cell Lung Cancer", Nature, vol. 228, Aug. 2, 2007, pp. 561-566.
Star et al., "Electronic Detection of Specific Protein Binding Using Nanotube FET Devices", Nano Letters, vol. 3, No. 4, 2003, 5 pages.
Su et al., "Surface Plasmon Resonance Spectroscopy and Quartz Crystal Microbalance Study of Streptavidin Film Structure Effects on Biotinylated Dna Assembly and Target DNA Hybridization", Langmuir, vol. 21, No. 1, 2005, pp. 348-353.
Tsai, "Kinetics of DNA Polymerase Conformational Changes during Nucleotide Binding and Incorporation", Dissertation, May 2005, 148 pages.
Tsai et al., "Site-Specific Labeling of T7 DNA Polymerase with a Conformationally Sensitive Fluorophore and its Use in Detecting Single-Nucleotide Polymorphisms", Analytical Biochemistry, vol. 384, No. 1, Jan. 1, 2009, pp. 136-144.
Vaidyanathan et al., "Binary and Ternary Binding Affinities Between Exonuclease-Deficient Klenow Fragment (Kf-exo-) and Various Arylamine DNA Lesions Characterized by Surface Plasmon Resonance", Chemical Research in Toxicology, vol. 25, No. 8, Aug. 20, 2012, pp. 1568-1570.
Vaidyanathan et al., "Binding Kinetics of DNA-Protein Interaction Using Surface Plasmon Resonance", Protocol Exchange, May 22, 2013, 11 pages.
Vollmer et al., "Whispering-Gallery-Mode Biosensing: Label-Free Detection Down to Single Molecules", Nature Methods, vol. 5, No. 7, Jul. 2008, pp. 591-596.
Walsh et al., "Synthetic Nucleotides as Probes of DNA Polymerase Specificity", Journal of Nucleic Acids, vol. 2012, Jun. 2012, 17 pages.
Washington et al., "Human DNA Polymerase Utilizes Different Nucleotide Incorporation Mechanisms Dependent upon the Template Base", Molecular and Cellular Biology, vol. 24, No. 2, Jan. 2004, pp. 936-943.
Xia et al., "DNA Mismatch Synthesis Complexes Provide Insights into Base Selectivity of a B Family DNA Polymerase", J Am Chem Soc., vol. 135, No. 1, Jan. 9, 2013, pp. 193-202.
Yuzenkova et al., "Tagetitoxin Inhibits Transcription by Stabilizing Pre-Translocated State of the Elongation Complex", Nucleic Acids Research, vol. 41, No. 20, Nov. 2013, pp. 1-9.
CA3,050,695, "Office Action", Jul. 5, 2021, 3 pages.
AU2018353136, "First Examination Report", Aug. 6, 2021, 5 pages.
AU2018353136, "Notice of Acceptance", May 5, 2022, 3 pages.
CA3,079,411, "Notice of Allowance", Jun. 30, 2023, 1 page.
CA3,079,411, "Office Action", May 5, 2022, 3 pages.
CA3,079,411, "Office Action", May 17, 2021, 4 pages.
EP18797436.5, "Office Action", Mar. 22, 2023, 6 pages.
PCT/US2015/041415, "International Search Report and Written Opinion", Feb. 9, 2016, 14 pages.
CA3,050,695, "Notice of Allowance", Oct. 5, 2023, 1 page.
CA3,050,695, "Office Action", Jun. 9, 2022, 5 pages.

\* cited by examiner

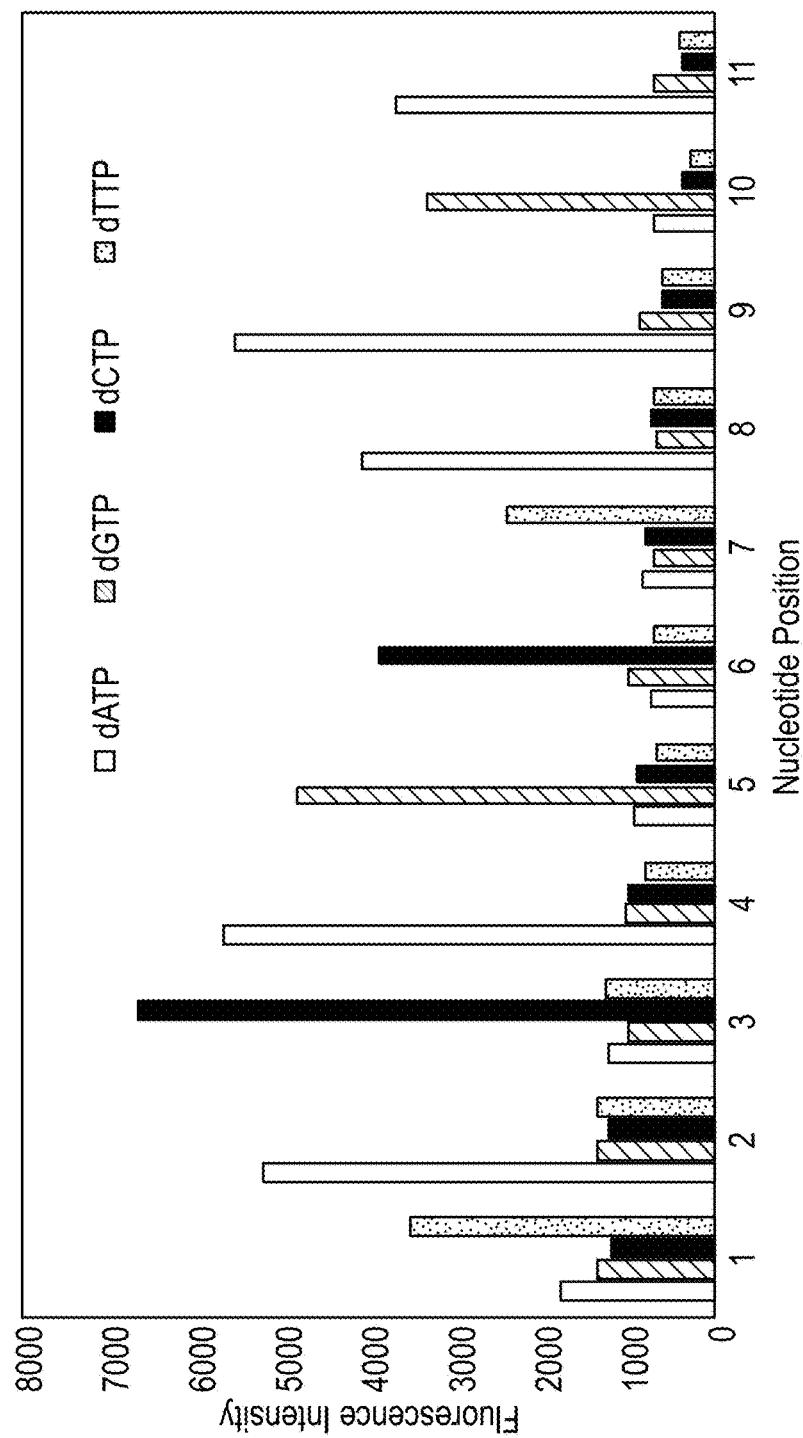
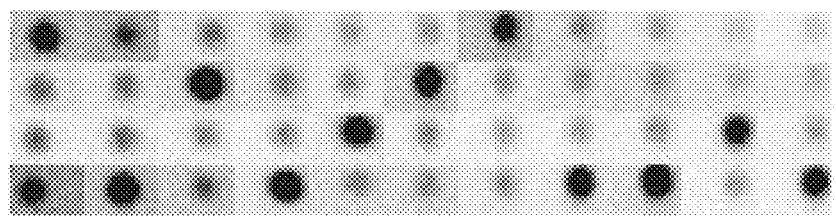
FIG. 5A
FIG. 5B

… (1)

PROCESS FOR COGNATE NUCLEOTIDE DETECTION IN A NUCLEIC ACID SEQUENCING WORKFLOW

RELATED APPLICATIONS

This application is a continuation of U.S. application Ser. No. 15/873,345, filed on Jan. 17, 2018, which claims the benefit of U.S. Provisional Application No. 62/448,839, filed Jan. 20, 2017; U.S. Provisional Application No. 62/450,397, filed Jan. 25, 2017; U.S. Provisional Application No. 62/506,759, filed May 16, 2017; and U.S. Provisional Application No. 62/574,308, filed Oct. 19, 2017. The disclosures of these earlier applications are hereby incorporated by reference in their entireties.

TECHNICAL FIELD

The present disclosure generally relates to the field of biotechnology. More specifically, the disclosure concerns a nucleic acid sequencing method and system.

BACKGROUND

The power and promise of next-generation sequencing (NGS) platforms result from the ability to generate extensive sequence information rapidly by parallel processing of different target nucleic acids on a massive scale. Not only are large numbers of targets sequenced simultaneously, but the cycle time can be kept short to facilitate this processing. Thus, reduction of the cycle time needed to determine one base supports the rapid processing.

Certain NGS approaches rely on the use of stepwise identification of cognate nucleotides by incorporating only one nucleotide at a time. Here, labeled reversible terminator nucleotides can be incorporated, the incorporated label identified, and cognate nucleotide identification made by associating the label identity with a nucleotide identity. Removal of the covalently attached reversible terminator moiety and the detectable label from the primed template renders the substrate available for the next round of nucleotide identification.

While very successful, the use of labeled reversible terminators slows the sequencing workflow. Additionally, inefficiencies in the repetitive chemistry steps compromise the approach and introduce the opportunity for undesired phasing and base calling errors. For example, removing a reversible terminator moiety from only some of the blocked primed template nucleic acids will prevent the next round of incorporation and cause correct nucleotide identification to lose register. Thus, there remains a need for a sequencing chemistry that is both rapid and efficient.

The present disclosure provides techniques that address this need, and provide other advantages as well.

SUMMARY OF THE DISCLOSURE

In one aspect, the disclosure relates to a method of identifying a next correct nucleotide within the sequence of a primed template nucleic acid molecule. The method includes the step of (a) providing a blocked primed template nucleic acid molecule immobilized to a solid support. There also is the step of (b) contacting the blocked primed template nucleic acid molecule with (i) a polymerase, and (ii) a nucleotide analog, whereby a ternary complex forms, without nucleotide incorporation, if the nucleotide analog includes the next correct nucleotide. The ternary complex includes each of the blocked primed template nucleic acid molecule, the polymerase, and the nucleotide analog, where the nucleotide analog includes a detectable label. There also is the step of (c) isolating the ternary complex from any of the nucleotide analog that contacted the blocked primed template nucleic acid molecule in step (b) but did not participate in ternary complex formation. There also is the step of (d) detecting the detectable label of the nucleotide analog present in the ternary complex isolated in step (c). There also is the step of (e) identifying the next correct nucleotide within the primed template nucleic acid molecule using the result from step (d). According to one generally preferred embodiment, step (a) can involve incorporating a reversible terminator nucleotide into an immobilized primed template nucleic acid molecule with a polymerase to produce the blocked primed template nucleic acid molecule. Preferably, the polymerase of step (b) is the same type of polymerase that is used for incorporating the reversible terminator nucleotide in step (a). According to another generally preferred embodiment, the blocked primed template nucleic acid molecule includes a reversible terminator moiety at its 3' terminus, and the method further includes the step of cleaving the reversible terminator moiety from the blocked primed template nucleic acid molecule to produce a 3' terminus available for polymerization. According to another generally preferred embodiment, the solid support in step (a) is contained within a flow cell, step (b) involves flowing into the flow cell a reagent that includes the polymerase and the nucleotide analog, step (c) involves flowing a stabilizing fluid through the flow cell to replace the reagent, and step (d) involves detecting in the presence of the stabilizing fluid. Preferably, the detectable label of the nucleotide analog includes a fluorescent detectable label, and step (d) involves detecting by fluorometry. More preferably, the fluorescent detectable label does not include an intercalating dye that changes fluorescence after contacting DNA. Alternatively, the fluorescent label can be covalently attached to the nucleotide analog by a linker at a position on the nitrogenous base. When this is the case, the stabilizing fluid can be a non-aqueous stabilizing fluid, or the stabilizing fluid can be a water-immiscible stabilizing fluid. In accordance with yet another alternative, the stabilizing fluid can be a water-immiscible stabilizing fluid. In accordance with a different embodiment, when the solid support in step (a) is contained within a flow cell, and step (b) involves flowing into the flow cell a reagent that includes the polymerase and the nucleotide analog, and step (c) involves flowing a stabilizing fluid through the flow cell to replace the reagent, and step (d) involves detecting in the presence of the stabilizing fluid, there are various preferred alternatives. For example, the reagent that includes the polymerase and the nucleotide analog can further include a divalent catalytic metal ion. Alternatively, the reagent does not include a noncatalytic metal ion that stabilizes ternary complexes and inhibits incorporation. Alternatively, step (d) is performed between 10 seconds and 10 minutes after step (c). Alternatively, the ternary complex is detectable after 5 minutes in the stabilizing fluid. According to still yet another generally preferred embodiment, the method further includes, after step (d), the steps of: stripping the polymerase and the nucleotide analog of the ternary complex from the blocked primed template nucleic acid molecule; cleaving a reversible terminator moiety from the blocked primed template nucleic acid molecule to create a deblocked primed template nucleic acid molecule including a 3' terminus available for polymerization; incorporating a reversible terminator into the deblocked primed template nucleic acid molecule; and then repeating steps (a)-(e). According to another generally preferred embodiment, the nucleotide analog in step (b) includes no more than two different nucleotide analogs, and the detectable label is the same for each different nucleotide analog. According to another generally preferred embodiment, the nucleotide analog in step (b) includes at least two different nucleotide analogs, and the detectable labels are different for each different nucleotide analog. According to another generally preferred embodiment, the solid support in step (a) is contained within a flow cell, step (c) includes flowing a stabilizing fluid through the flow cell to replace any liquid volume contained therein, and the stabilizing fluid is substantially free of the nucleotide analog that includes the detectable label. Preferably, step (e) is performed after a plurality of cycles of performing steps (b)-(d), and each of the plurality of cycles uses a different nucleotide analog.

In another aspect, the disclosure relates to a method of identifying cognate nucleotides for different primed template nucleic acid molecules immobilized among a plurality of nucleic acid features. The method includes the step of (a) contacting the plurality of nucleic acid features with a first reagent that includes a plurality of reversible terminator nucleotides, a plurality of distinguishably labeled non-incorporable nucleotide analogs, at least one polymerase, and a catalytic metal ion, whereby a first reaction mixture is created, and whereby one of the reversible terminator nucleotides of the first reaction mixture incorporates into each of the different primed template nucleic acid molecules to produce a blocked primed template nucleic acid molecule at each of the plurality of nucleic acid features. There also is the step of (b) detecting, in the first reaction mixture, complexes including one of the polymerases, one of the blocked primed template nucleic acid molecules and one of the distinguishably labeled non-incorporable nucleotide analogs at each of the plurality of nucleic acid features. There also is the step of (c) identifying cognate nucleotides for different primed template nucleic acid molecules immobilized among the plurality of nucleic acid features by identifying the distinguishably labeled non-incorporable nucleotide analogs of the complexes detected in step (b). According to one generally preferred embodiment, the plurality of reversible terminator nucleotides includes four different reversible terminator nucleotides, and the plurality of distinguishably labeled non-incorporable nucleotides includes four different distinguishably labeled non-incorporable nucleotide analogs. Preferably, at least one of the four different distinguishably labeled non-incorporable nucleotide analogs includes a fluorescent label, and none of the four different distinguishably labeled non-incorporable nucleotide analogs includes an intercalating dye that changes fluorescence after contacting DNA. Preferably, each of the four different distinguishably labeled non-incorporable nucleotide analogs includes a different detectable label. More preferably, step (b) involves detecting the different detectable labels of the four different distinguishably labeled non-incorporable nucleotide analogs. Alternatively, each of the different detectable labels can include a different fluorescent label. In accordance with embodiments where the plurality of reversible terminator nucleotides includes four different reversible terminator nucleotides, and the plurality of distinguishably labeled non-incorporable nucleotides includes four different distinguishably labeled non-incorporable nucleotide analogs, there are alternatives that can be used. For example, each of the four different reversible terminator nucleotides can include a reversible terminator moiety, and each of the four different distinguishably labeled non-incorporable nucleotide analogs can include a different fluorescent label. Alternatively, each of the four different reversible terminator nucleotides can include a reversible terminator moiety, each of the four different distinguishably labeled non-incorporable nucleotide analogs can include a different detectable label, and none of the different detectable labels is an intercalating dye that changes fluorescence after contacting DNA. Alternatively, each of the different fluorescent labels can be covalently attached to one of the four different distinguishably labeled non-incorporable nucleotide analogs at a position on its base moiety. Alternatively, each of the four different distinguishably labeled non-incorporable nucleotide analogs can include a triphosphate group with a modified linkage between alpha and beta phosphorus atoms. More preferably, each of the different fluorescent labels can be covalently attached to one of the four different distinguishably labeled non-incorporable nucleotide analogs at a position on its base moiety. In accordance with other embodiments wherein the plurality of reversible terminator nucleotides includes four different reversible terminator nucleotides, and the plurality of distinguishably labeled non-incorporable nucleotides includes four different distinguishably labeled non-incorporable nucleotide analogs, there are still other alternatives that can be used. For example, each of the four different distinguishably labeled non-incorporable nucleotide analogs can include a different fluorescent label, and the four different reversible terminator nucleotides do not include distinguishable fluorescent labels. Alternatively, each of the four different reversible terminator nucleotides can include a 3'-OH modification. More preferably, the 3'-OH modification can include a 3'-ONH$_2$ moiety. According to yet another alternative, the method further includes the steps of: (d) replacing the first reagent with a second reagent that destabilizes ternary complexes; and (e) replacing the second reagent with a third reagent that removes a reversible terminator moiety from each of the blocked primed template nucleic acid molecules. More preferably, step (d) takes place before step (c), and step (c) is performed using results from step (b) that have been stored electronically. According to yet another alternative, the catalytic metal ion of the first reagent is either $Mg^{2+}$ ion or $Mn^{2+}$ ion. Alternatively, steps (a)-(e) can be repeated to identify successive cognate nucleotides for each of the different primed template nucleic acid molecules. In accordance with embodiments wherein at least one of the four different distinguishably labeled non-incorporable nucleotide analogs includes a fluorescent label, and none of the four different distinguishably labeled non-incorporable nucleotide analogs includes an intercalating dye that changes fluorescence after contacting DNA, one of the polymerases in step (b) does not include an exogenous label in energy transfer relationship with the fluorescent label of any of the distinguishably labeled non-incorporable nucleotide analogs, and the catalytic metal ion of the first reagent is either $Mg^{2+}$ ion or $Mn^{2+}$ ion. According to another generally preferred embodiment, at least one of the distinguishably labeled non-incorporable nucleotide analogs includes a fluorescent label, and none of the distinguishably labeled non-incorporable nucleotide analogs includes an intercalating dye that changes fluorescence after contacting DNA. More preferably, the one of the polymerases in step (b) does not include an exogenous label in energy transfer relationship with the fluorescent label of any of the distinguishably labeled non-incorporable nucleotide analogs, and the catalytic metal ion of the first reagent is either $Mg^{2+}$ ion or $Mn^{2+}$ ion. According to another generally preferred embodiment, each of the plurality of distinguishably labeled non-incorporable nucleotide analogs includes a different detectable label. More preferably, step (b) can involve detecting the different detectable labels of the plurality of distinguishably labeled non-incorporable nucleotide analogs. Alternatively, each of the different detectable labels can include a different fluorescent label. According to another generally preferred embodiment, each of the plurality of reversible terminator nucleotides can include a reversible terminator moiety, and each of the plurality of distinguishably labeled non-incorporable nucleotide analogs can include a different fluorescent label. More preferably, each of the different fluorescent labels can be covalently attached to one of the plurality of distinguishably labeled non-incorporable nucleotide analogs at a position on its base moiety. Alternatively, each of the plurality of distinguishably labeled non-incorporable nucleotide analogs includes a triphosphate group with a modified linkage between alpha and beta phosphorus atoms. More preferably, each of the different fluorescent labels is covalently attached to one of the plurality of distinguishably labeled non-incorporable nucleotide analogs at a position on its base moiety. According to another generally preferred embodiment, each of the plurality of reversible terminator nucleotides can include a reversible terminator moiety, each of the plurality of distinguishably labeled non-incorporable nucleotide analogs can include a different detectable label, and none of the different detectable labels is an intercalating dye that changes fluorescence after contacting DNA. According to another generally preferred embodiment, each of the plurality of distinguishably labeled non-incorporable nucleotide analogs includes a different fluorescent label, and the plurality of reversible terminator nucleotides does not include distinguishable fluorescent labels. According to another generally preferred embodiment, each of the plurality of reversible terminator nucleotides includes a 3'-OH modification. More preferably, the 3'-OH modification includes a 3'-ONH$_2$ moiety. According to another generally preferred embodiment, the method further includes the steps of: (d) replacing the first reagent with a second reagent that destabilizes ternary complexes; and (e) replacing the second reagent with a third reagent that removes a reversible terminator moiety from each of the blocked primed template nucleic acid molecules. Preferably, step (d) takes place before step (c), and step (c) is performed using results from step (b) that have been stored electronically. Alternatively, steps (a)-(d) can be repeated to identify successive cognate nucleotides for each of the different primed template nucleic acid molecules. According to another generally preferred embodiment, the catalytic metal ion of the first reagent is either Mg$^{2+}$ ion or Mn$^{2+}$ ion.

In another aspect, the disclosure relates to a method of identifying a cognate nucleotide within the sequence of a primed template nucleic acid molecule. The method includes the step of (a) contacting the primed template nucleic acid molecule with a first reagent to create a first reaction mixture, where the first reagent includes at least one polymerase, a catalytic metal ion, one or more nucleotide analogs including a reversible terminator moiety, and one or more labeled nucleotide analogs, each labeled nucleotide analog including a nucleotide base-specific label. As a consequence, a single nucleotide analog harboring the reversible terminator moiety incorporates into the primed template nucleic acid molecule at the N+1 position thereof to produce a reversibly blocked primed template nucleic acid molecule. There also is the step of (b) detecting, in the first reaction mixture, formation of a stabilized ternary complex including the reversibly blocked primed template nucleic acid molecule, one of the polymerases, and one of the labeled nucleotide analogs. There also is the step of (c) identifying the cognate nucleotide for the N+2 position of the primed template nucleic acid molecule by identifying the nucleotide base-specific label present in the stabilized ternary complex. According to one generally preferred embodiment, each nucleotide base-specific label includes a fluorescent moiety indicating nucleotide base identity. According to another generally preferred embodiment, each nucleotide base-specific label includes a base-specific fluorescent moiety that does not substantially change fluorescence after binding to DNA. According to another generally preferred embodiment, each nucleotide base-specific label includes a base-specific fluorescent moiety, and neither the nucleotide analog including the reversible terminator moiety nor the at least one polymerase includes an energy transfer partner required for detecting formation of the stabilized ternary complex in step (b). According to another generally preferred embodiment, the nucleotide analog harboring the reversible terminator moiety is an unlabeled nucleotide analog that does not include a fluorescent moiety. According to another generally preferred embodiment, each labeled nucleotide analog is a non-incorporable nucleotide analog. According to another generally preferred embodiment, the method further includes the steps of: (d) contacting the reversibly blocked primed template nucleic acid molecule with a second reagent that destabilizes ternary complexes; and (e) contacting the reversibly blocked primed template nucleic acid molecule with a third reagent that removes the reversible terminator moiety from the reversibly blocked primed template nucleic acid molecule. More preferably, the method further includes the step of (f) repeating steps (a)-(e) to determine the next cognate nucleotide within the sequence of the primed template nucleic acid molecule. In accordance with certain embodiments wherein each nucleotide base-specific label includes a base-specific fluorescent moiety that does not substantially change fluorescence after binding to DNA, it is preferred that neither the nucleotide analog including the reversible terminator moiety nor the at least one polymerase includes an energy transfer partner required for detecting formation of the stabilized ternary complex in step (b). More preferably, the nucleotide analog that includes the reversible terminator moiety is an unlabeled nucleotide analog that does not include a fluorescent moiety. More preferably, each labeled nucleotide analog is a non-incorporable nucleotide analog. Still more preferably, the method further includes the steps of: (d) contacting the reversibly blocked primed template nucleic acid molecule with a second reagent that destabilizes ternary complexes; and (e) contacting the reversibly blocked primed template nucleic acid molecule with a third reagent that removes the reversible terminator moiety from the reversibly blocked primed template nucleic acid molecule. Yet still more preferably, the method further includes the step of (f) repeating steps (a)-(e) to determine the next cognate nucleotide within the sequence of the primed template nucleic acid molecule. According to another generally preferred embodiment, the nucleotide analogs are distinguishably labeled reversible terminator nucleotides.

In another aspect, the disclosure relates to a method of identifying a cognate nucleotide within the sequence of a primed template nucleic acid molecule. The method includes the step of (a) contacting the primed template nucleic acid molecule with a first reagent to create a first reaction mixture, where the first reagent includes at least one polymerase, a catalytic metal ion, and four reversible terminator nucleotide analogs, each of the reversible terminator nucleotide analogs including a different base and a distinguishable base-specific label. As a consequence of this, one of the reversible terminator nucleotide analogs incorporates into the primed template nucleic acid molecule at the N+1 position thereof to produce a reversibly blocked primed template nucleic acid molecule. There also is the step of (b) detecting, in the first reaction mixture, formation of a stabilized ternary complex including the reversibly blocked primed template nucleic acid molecule, one of the polymerases, and one of the reversible terminator nucleotide analogs. There also is the step of (c) identifying the cognate nucleotide for the N+2 position of the primed template nucleic acid molecule by identifying the distinguishable base-specific label present in the stabilized ternary complex. According to one generally preferred embodiment, each of the distinguishable base-specific labels can be covalently linked to a moiety that is removed from the reversible terminator nucleotide analog upon incorporation into the primed template nucleic acid molecule. For example, each of the distinguishable base-specific labels can be covalently linked to a phosphate moiety. According to another generally preferred embodiment, each of the reversible terminator nucleotide analogs is linked to a reversible terminator moiety at the 3' position of the sugar moiety. According to another generally preferred embodiment, the method further includes the steps of: (d) contacting the reversibly blocked primed template nucleic acid molecule with a second reagent that destabilizes ternary complexes; and (e) contacting the reversibly blocked primed template nucleic acid molecule with a third reagent that removes the reversible terminator moiety from the reversibly blocked primed template nucleic acid molecule. More preferably, the method further includes the step of (f) repeating steps (a)-(e) to determine the next cognate nucleotide within the sequence of the primed template nucleic acid molecule. According to another generally preferred embodiment, the primed template nucleic acid molecule is contained within a flow cell, and step (a) includes flowing the first reagent through the flow cell. According to another generally preferred embodiment, each nucleotide base-specific label includes a fluorescent moiety indicating nucleotide base identity. According to another generally preferred embodiment, each nucleotide base-specific label includes a base-specific fluorescent label that does not substantially change fluorescence after binding to DNA. According to another generally preferred embodiment, each nucleotide base-specific label includes a base-specific fluorescent label, and neither the nucleotide analog that includes the reversible terminator moiety nor the at least one polymerase includes an energy transfer partner required for detecting formation of the stabilized ternary complex in step (b). According to another generally preferred embodiment, the nucleotide analog that includes the reversible terminator moiety is an unlabeled nucleotide analog that does not include a fluorescent label.

In another aspect, the disclosure relates to a reaction mixture. The reaction mixture includes: (a) a primed template nucleic acid molecule including a 3'-end available for polymerization; (b) one or more polymerases; (c) one or more incorporable reversible terminator nucleotides; (d) one or more distinguishably labeled nucleotide analogs; and (e) a catalytic metal ion. According to one generally preferred embodiment, the one or more incorporable reversible terminator nucleotides can include four incorporable reversible terminator nucleotides. For example, the one or more distinguishably labeled nucleotide analogs can include four distinguishably labeled nucleotide analogs. More preferably, the four incorporable reversible terminator nucleotides are not distinguishably labeled. Alternatively, the four incorporable reversible terminator nucleotides are distinguishably labeled. Alternatively, each of the distinguishably labeled nucleotide analogs is a distinguishably labeled non-incorporable nucleotide analog. In some embodiments, the four incorporable reversible terminator nucleotides are not distinguishably labeled. Preferably, each of the distinguishably labeled non-incorporable nucleotide analogs includes a different fluorescent label, and each of the different fluorescent labels is covalently attached to one of the distinguishably labeled non-incorporable nucleotide analogs at a position on its base moiety. More preferably, none of the different fluorescent labels is an intercalating dye that changes fluorescence after contacting DNA. Alternatively, each of the distinguishably labeled nucleotide analogs is a distinguishably labeled incorporable nucleotide analog. In some embodiments, the four incorporable reversible terminator nucleotides are distinguishably labeled. Alternatively, each of the four distinguishably labeled non-incorporable nucleotide analogs includes a triphosphate group with a modified linkage between alpha and beta phosphorus atoms. According to another generally preferred embodiment, the one or more distinguishably labeled nucleotide analogs can include four distinguishably labeled nucleotide analogs. According to another generally preferred embodiment, the one or more incorporable reversible terminator nucleotides are not distinguishably labeled. According to another generally preferred embodiment, the one or more incorporable reversible terminator nucleotides are distinguishably labeled. According to another generally preferred embodiment, each of the distinguishably labeled nucleotide analogs is a distinguishably labeled non-incorporable nucleotide analog. According to another generally preferred embodiment, each of the distinguishably labeled nucleotide analogs is a distinguishably labeled incorporable nucleotide analog. According to another generally preferred embodiment, each of the distinguishably labeled nucleotide analogs includes a distinguishable fluorescent label, and none of the distinguishable fluorescent labels is an intercalating dye that changes fluorescence after contacting DNA. According to another generally preferred embodiment, the catalytic metal ion is either $Mg^{2+}$ ion or $Mn^{2+}$ ion. According to another generally preferred embodiment, each of the incorporable reversible terminator nucleotides includes a 3'-OH modification. According to another generally preferred embodiment, the primed template nucleic acid molecule is attached to a feature of an array. More preferably, the array includes a plurality of features, and wherein each feature is attached to a different primed template nucleic acid molecule.

In another aspect, the disclosure relates to a method of identifying a next correct nucleotide within the sequence of a primed template nucleic acid molecule. The method includes the step of (a) incorporating a reversible terminator nucleotide into the primed template nucleic acid molecule to produce a blocked primed template nucleic acid molecule. There also is the step of (b) contacting the blocked primed template nucleic acid molecule with a first reagent that includes (i) a polymerase, and (ii) at least one labeled nucleotide analog, where each labeled nucleotide analog includes a distinguishable label specific for the base of that nucleotide analog. This results in formation of a stabilized ternary complex that includes each of the blocked primed template nucleic acid molecules, the polymerase, and the labeled nucleotide analog that is the next correct nucleotide. There also is the step of (c) detecting the distinguishable label of the labeled nucleotide analog of the stabilized ternary complex, thereby identifying the next correct nucleotide within the primed template nucleic acid molecule. According to one generally preferred embodiment, the reversible terminator nucleotide is an unlabeled reversible terminator nucleotide. According to another generally preferred embodiment, each of the at least one labeled nucleotide analog in step (b) is at least one labeled non-incorporable nucleotide analog, and step (c) involves detecting the distinguishable label of the labeled non-incorporable nucleotide analog of the stabilized ternary complex, thereby identifying the next correct nucleotide within the primed template nucleic acid molecule. Preferably, each of the four labeled non-incorporable nucleotide analogs is present at a concentration in the range of from 10 nM to 200 nM. Preferably, the at least one labeled non-incorporable nucleotide analog includes four distinguishably labeled non-incorporable nucleotide analogs. Preferably, the distinguishable label of the labeled non-incorporable nucleotide analog present in the stabilized ternary complex includes a fluorescent label, and the fluorescent label is not an intercalating dye that changes fluorescence after contacting DNA. More preferably, neither the reversible terminator nucleotide nor the at least one polymerase includes an energy transfer partner required for detecting the fluorescent label in step (c). In some embodiments, the first reagent further includes a divalent catalytic metal ion. In some embodiments, the method further includes the step of (d) contacting the blocked primed template nucleic acid molecule, after step (c), with a second reagent that destabilizes ternary complexes and removes the reversible terminator moiety, whereby the blocked primed template nucleic acid molecule is deblocked and made available for polymerization. In some embodiments, the method further includes the step of (e) repeating steps (a)-(c) using the deblocked product of step (d) as the primed template nucleic acid molecule to determine a next correct nucleotide within the sequence of the primed template nucleic acid molecule. In some embodiments, the distinguishable label of each of the at least one labeled non-incorporable nucleotide analogs includes a distinguishable fluorescent label that is not an intercalating dye that changes fluorescence after contacting DNA. Preferably, neither the reversible terminator nucleotide nor the at least one polymerase includes an energy transfer partner required for detecting the distinguishable fluorescent label in step (c). More preferably, the at least one labeled non-incorporable nucleotide analog includes four labeled non-incorporable nucleotide analogs. In some embodiments, the at least one labeled non-incorporable nucleotide analog includes four distinguishably labeled non-incorporable nucleotide analogs. Preferably, the distinguishable label of each of the four labeled non-incorporable nucleotide analogs includes a distinguishable fluorescent moiety. Preferably, each distinguishable fluorescent moiety is covalently attached by a linker at position 5 of the nitrogenous base for pyrimidine nucleotide analogs, or at position 7 of the nitrogenous base for purine nucleotide analogs. More preferably, each of the four labeled non-incorporable nucleotide analogs is present at a concentration in the range of from 10 nM to 200 nM. According to another generally preferred embodiment, each distinguishable label includes a base-specific fluorescent moiety, and neither the reversible terminator nucleotide nor the at least one polymerase includes an energy transfer partner required for detecting the base-specific fluorescent moiety of the distinguishable label in step (c). Preferably, the base-specific fluorescent moiety does not include an intercalating dye that changes fluorescence after contacting DNA. According to another generally preferred embodiment, the distinguishable label of the labeled nucleotide analog present in the stabilized ternary complex includes a fluorescent label, and the fluorescent label is not an intercalating dye that changes fluorescence after contacting DNA. Preferably, the fluorescent label is covalently attached to labeled nucleotide analog by a linker at a position on the nitrogenous base. More preferably, the linker is attached at position 5 of the nitrogenous base for pyrimidines, and wherein the linker is attached at position 7 of the nitrogenous base for purines. According to another generally preferred embodiment, the at least one labeled nucleotide analog includes four labeled nucleotide analogs. According to another generally preferred embodiment, the first reagent further includes a divalent catalytic metal ion. Preferably, the first reagent does not include a non-catalytic metal ion that inhibits polymerization. More preferably, the at least one labeled nucleotide analog includes four labeled nucleotide analogs. Still more preferably, the distinguishable label of each of the four labeled nucleotide analogs includes a distinguishable fluorescent moiety covalently attached at a position on the nitrogenous base by a linker. Even more preferably, the linker is attached at position 5 of the nitrogenous base for pyrimidines, and wherein the linker is attached at position 7 of the nitrogenous base for purines. Yet still more preferably, each of the four labeled nucleotide analogs is present at a concentration in the range of from 10 nM to 200 nM. In some embodiments, each of the four labeled nucleotide analogs is present at a concentration in the range of from 10 nM to 200 nM. According to another generally preferred embodiment, the first reagent does not include a non-catalytic metal ion that inhibits polymerization. According to another generally preferred embodiment, each of the at least one labeled nucleotide analogs of the first reagent is present at a concentration in the range of from 10 nM to 200 nM. According to another generally preferred embodiment, neither the reversible terminator nucleotide nor the polymerase includes an energy transfer partner required for detecting the distinguishable label in step (c).

In another aspect, the disclosure relates to a method of identifying cognate nucleotides for each of a plurality of nucleic acid features, with each feature including a primed template nucleic acid molecule. The method includes the step of (a) preparing first stabilized ternary complexes at each of the plurality of nucleic acid features, each stabilized ternary complex including the primed template nucleic acid molecule at its respective nucleic acid feature, a reversible terminator nucleotide, and a polymerase. There also is the step of (b) contacting the first stabilized ternary complexes from step (a) with a reagent including a catalytic metal ion, at least one distinguishably labeled incorporable nucleotide, and a polymerase, to produce a reaction mixture. As a result, the reversible terminator nucleotide incorporates into the primed template nucleic acid molecule to produce a blocked primed template nucleic acid molecule at each of the plurality of nucleic acid features, and there forms at each of the plurality of nucleic acid features a second stabilized ternary complex including the blocked primed template nucleic acid molecule and one of the distinguishably labeled incorporable nucleotides. There also is the step of (c) identifying cognate nucleotides for the primed template nucleic acid molecules at each of the plurality of nucleic acid features by detecting, in the reaction mixture, a label joined to the distinguishably labeled incorporable nucleotide of the second stabilized ternary complex. According to one generally preferred embodiment, step (a) involves preparing, in a first reaction mixture, the first stabilized ternary complexes, and step (b) involves contacting in a second reaction mixture, that is different from the first reaction mixture, the first stabilized ternary complexes. According to another generally preferred embodiment, the reversible terminator nucleotide is unlabeled, and includes a reversible terminator moiety. According to another generally preferred embodiment, the polymerases in the first and second reaction mixtures are identical. According to another generally preferred embodiment, each of the plurality of nucleic acid features is contained in a flow cell. According to another generally preferred embodiment, the catalytic metal ion in the second reaction mixture is selected from the group consisting of $Mg^{2+}$ ion, and $Mn^{2+}$ ion. According to another generally preferred embodiment, none of the at least one distinguishably labeled incorporable nucleotide includes a reversible terminator moiety. According to another generally preferred embodiment, each of the at least one distinguishably labeled incorporable nucleotide includes a distinguishable fluorescent label, and the label detected in the second reaction mixture is one of the distinguishable fluorescent labels. According to another generally preferred embodiment, the at least one distinguishably labeled incorporable nucleotide of the second reaction mixture includes four distinguishably labeled incorporable nucleotides. According to another generally preferred embodiment, the method further includes the step of (d) preparing a third reaction mixture by contacting the second stabilized ternary complex with one or more wash reagents that destabilize ternary complexes and remove a reversible terminator moiety of each of the reversible terminator nucleotide, whereby 3'-ends of each of the primed template nucleic acid molecules are made available for polymerization. In some embodiments, the method further involves repeating steps (a)-(d).

In another aspect, the disclosure relates to a method of identifying cognate nucleotides for different primed template nucleic acid molecules immobilized among a plurality of nucleic acid features. The method includes the step of (a) contacting the plurality of nucleic acid features with a first reagent that includes a plurality of reversible terminator nucleotides, a plurality of distinguishably labeled non-incorporable nucleotide analogs, at least one polymerase, and a catalytic metal ion. As a result, a first reaction mixture is created, and one of the reversible terminator nucleotides of the first reaction mixture incorporates into each of the different primed template nucleic acid molecules to produce a blocked primed template nucleic acid molecule at each of the plurality of nucleic acid features. There also is the step of (b) detecting, in the first reaction mixture, complexes including one of the polymerases, one of the blocked primed template nucleic acid molecules and one of the distinguishably labeled non-incorporable nucleotide analogs at each of the plurality of nucleic acid features. There also is the step of (c) identifying cognate nucleotides for different primed template nucleic acid molecules immobilized among the plurality of nucleic acid features by identifying the distinguishably labeled non-incorporable nucleotide analogs of the complexes detected in step (b), where the distinguishably labeled non-incorporable nucleotide analogs are selected from the group consisting of:

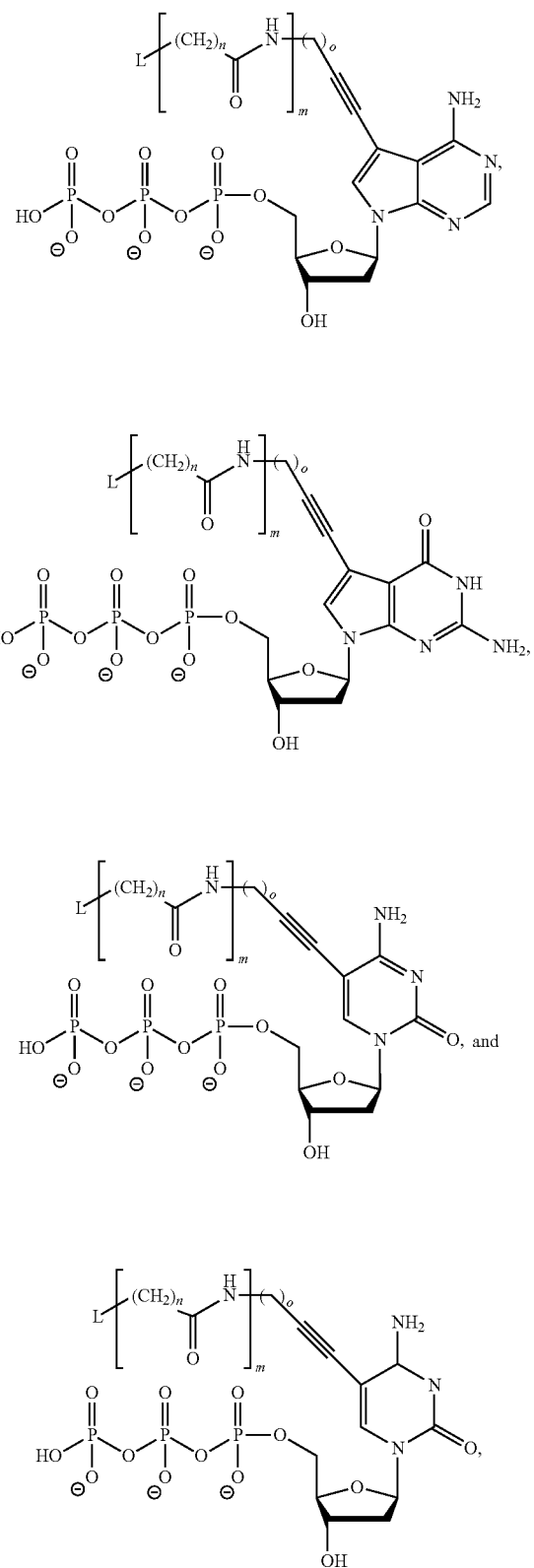

wherein L is a label moiety, n is any integer from 1 to 10, m is any integer from 1 to 5, and o is any integer from 1 to 10. Preferably, the distinguishably labeled non-incorporable nucleotide analogs are selected from the group consisting of:

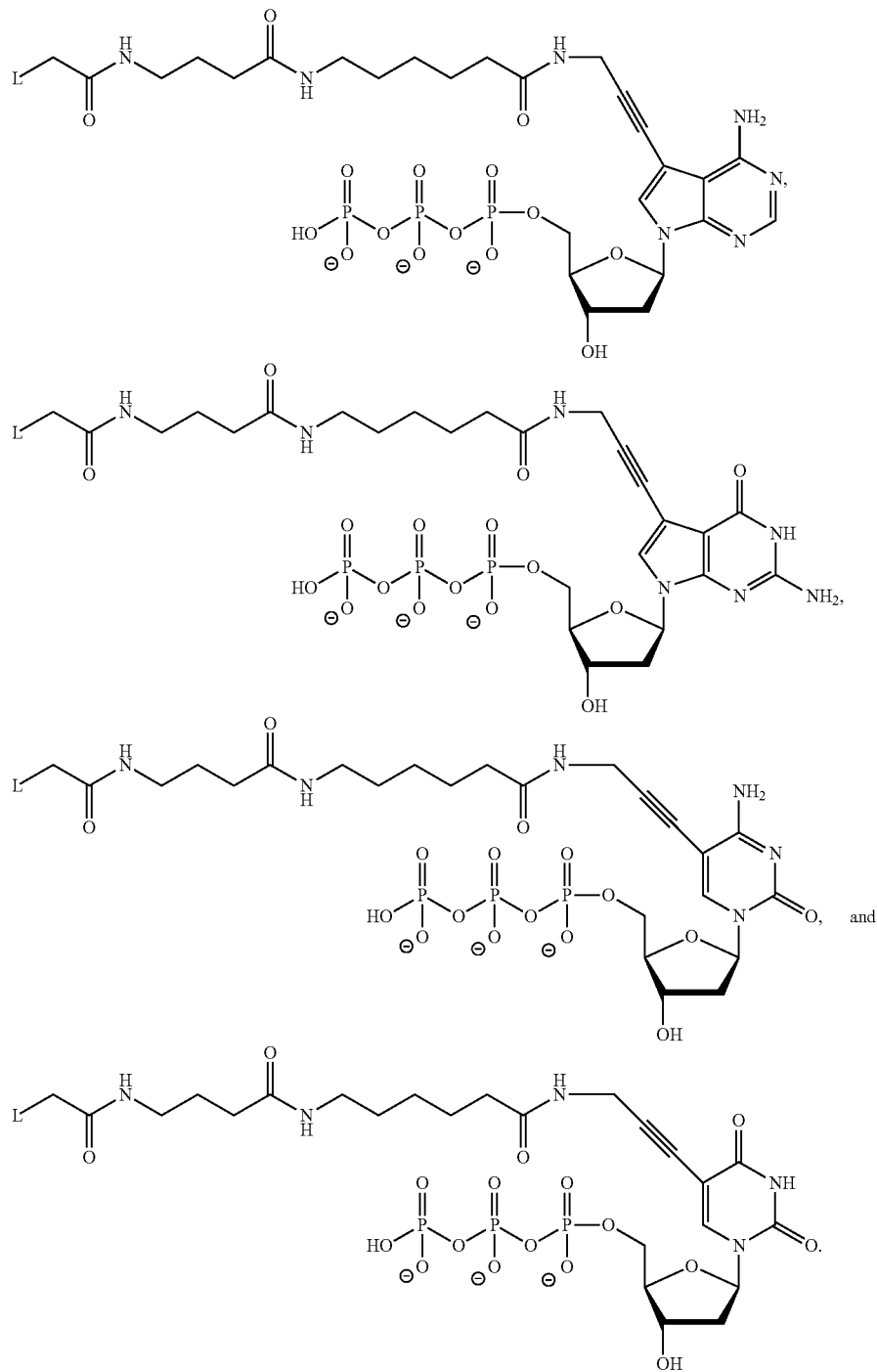

In another aspect, the disclosure relates to a method of identifying a cognate nucleotide within the sequence of a primed template nucleic acid molecule. The method includes the step of (a) contacting the primed template nucleic acid molecule with a first reagent to create a first reaction mixture, wherein the first reagent includes at least one polymerase, a catalytic metal ion, one or more nucleotide analogs including a reversible terminator moiety, and one or more labeled nucleotide analogs, each labeled nucleotide analog including a nucleotide base-specific label. As a result, a single nucleotide analog harboring the reversible terminator moiety incorporates into the primed template nucleic acid molecule at the N+1 position thereof to produce a reversibly blocked primed template nucleic acid molecule. There also is the step of (b) detecting, in the first reaction mixture, formation of a stabilized ternary complex including the reversibly blocked primed template nucleic acid molecule, one of the polymerases, and one of the labeled nucleotide analogs. There also is the step of (c) identifying the cognate nucleotide for the N+2 position of the primed template nucleic acid molecule by identifying the nucleotide base-specific label present in the stabilized ternary complex, where the one or more labeled nucleotide analogs are selected from the group consisting of:
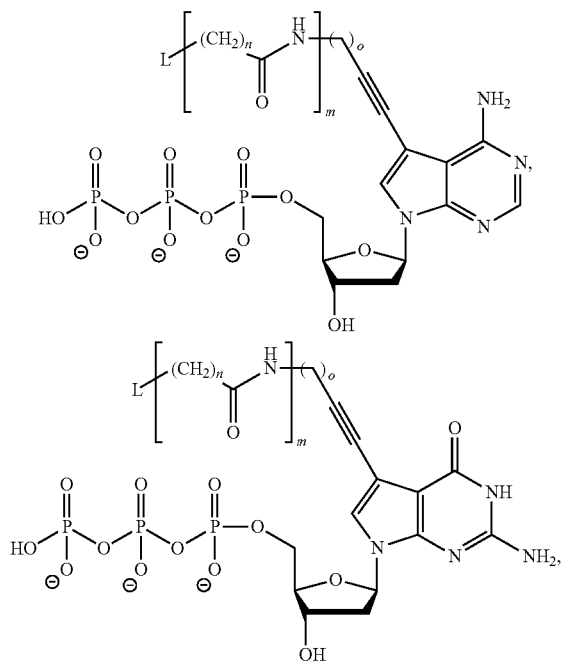
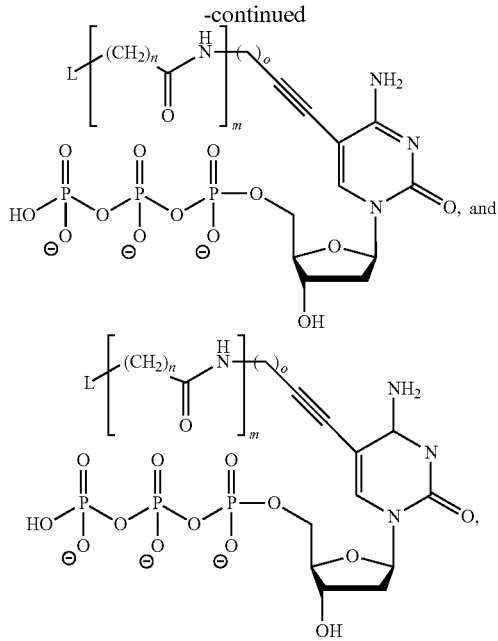
wherein L is a label moiety, n is any integer from 1 to 10, m is any integer from 1 to 5, and o is any integer from 1 to 10. More preferably, the distinguishably labeled non-incorporable nucleotide analogs are selected from the group consisting of:
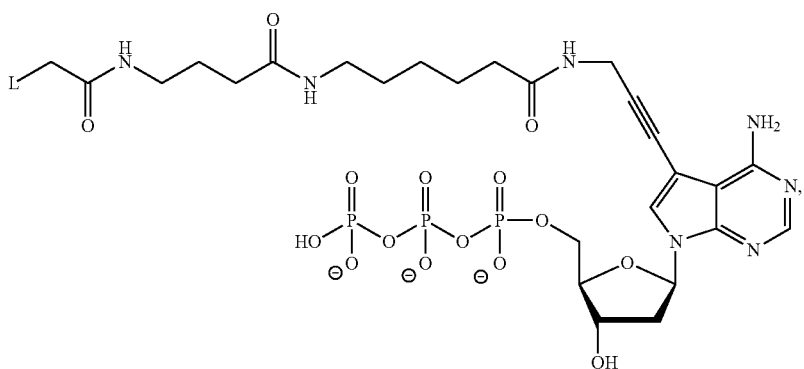
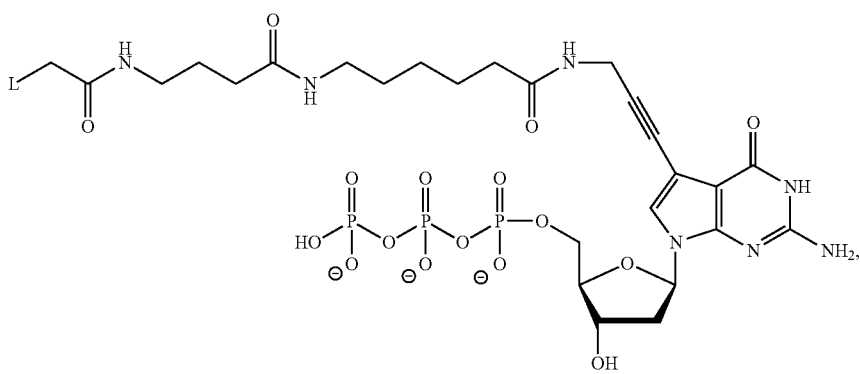

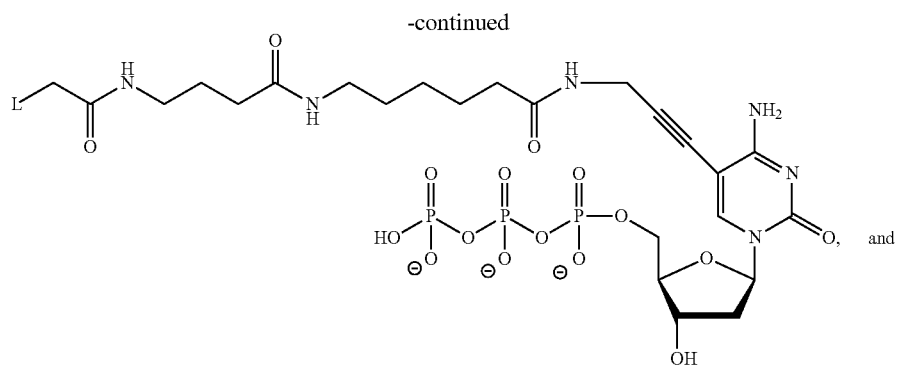

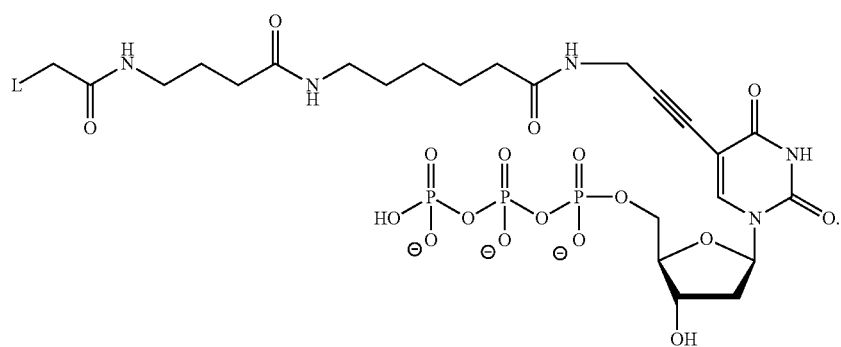

In another aspect, the disclosure relates to a method of identifying a next correct nucleotide within the sequence of a primed template nucleic acid molecule. The method includes the step of (a) incorporating a reversible terminator nucleotide into the primed template nucleic acid molecule to produce a blocked primed template nucleic acid molecule. There also is the step of (b) contacting the blocked primed template nucleic acid molecule with a first reagent including (i) a polymerase, and (ii) at least one labeled nucleotide analog, where each labeled nucleotide analog includes a distinguishable label specific for the base of that nucleotide analog. As a result, there forms a stabilized ternary complex including each of the blocked primed template nucleic acid molecules, the polymerase, and the labeled nucleotide analog that is the next correct nucleotide. There also is the step of (c) detecting the distinguishable label of the labeled nucleotide analog of the stabilized ternary complex, thereby identifying the next correct nucleotide within the primed template nucleic acid molecule. The at least one labeled nucleotide analog is selected from the group consisting of:

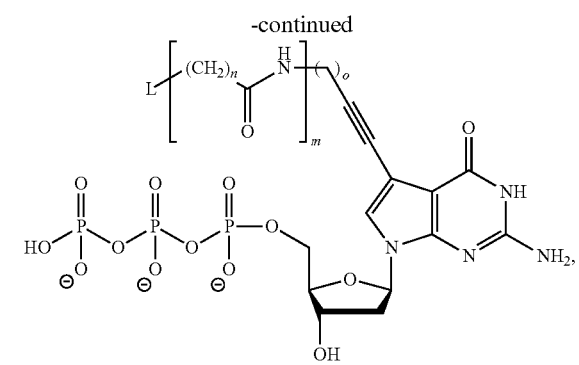

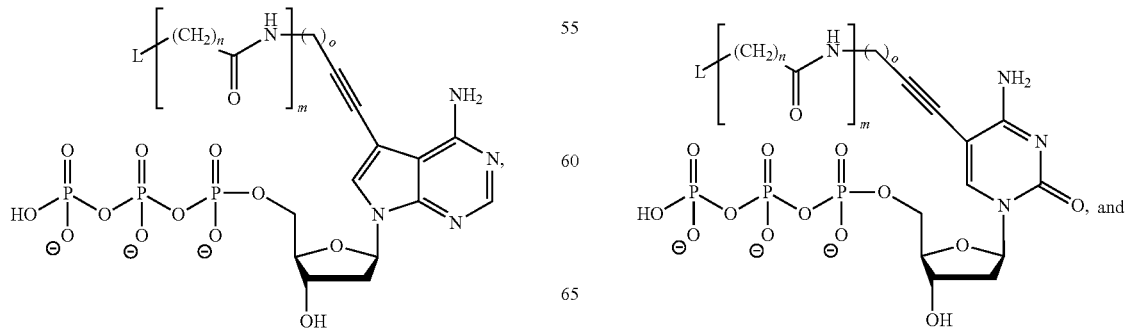

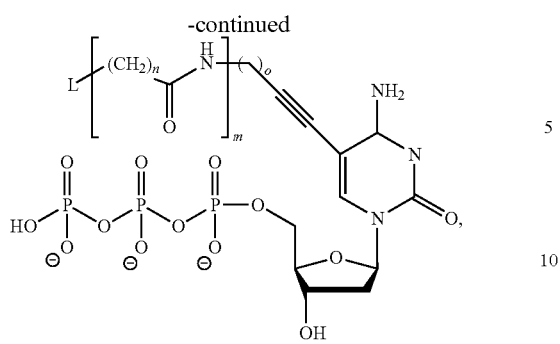
wherein L is a label moiety, n is any integer from 1 to 10, m is any integer from 1 to 5, and o is any integer from 1 to 10. Preferably, the at least one labeled nucleotide analog is selected from the group consisting of:
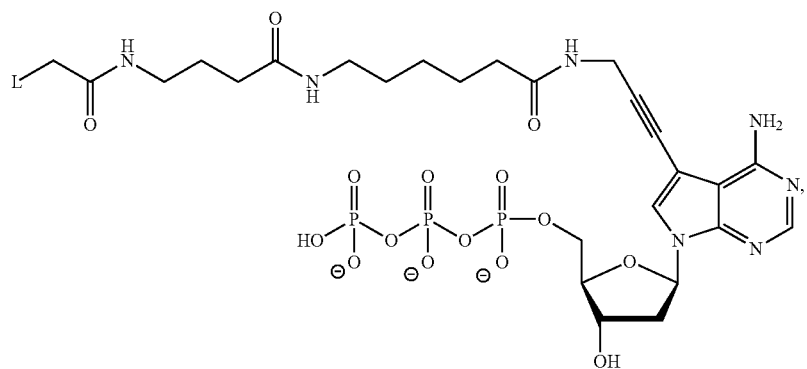
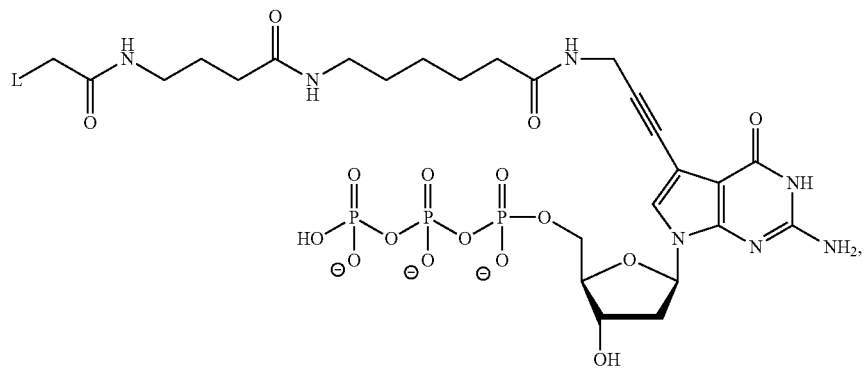
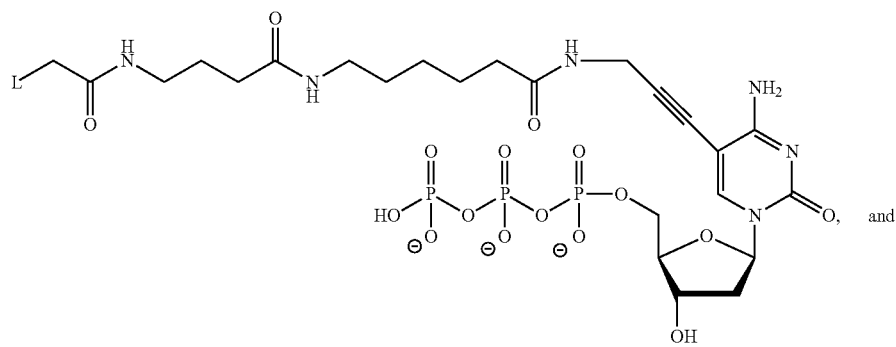
and

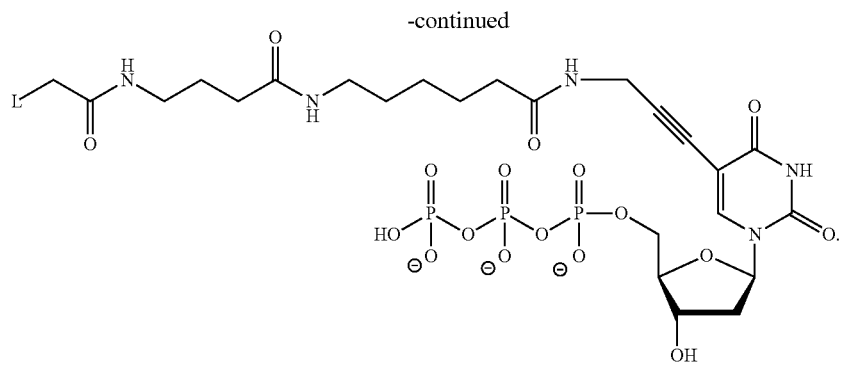

In another aspect, the disclosure relates to a method of identifying cognate nucleotides for each of a plurality of nucleic acid features, where each feature includes a primed template nucleic acid molecule. The method includes the step of (a) preparing first stabilized ternary complexes at each of the plurality of nucleic acid features, where each stabilized ternary complex includes the primed template nucleic acid molecule at its respective nucleic acid feature, a reversible terminator nucleotide, and a polymerase. There also is the step of (b) contacting the first stabilized ternary complexes from step (a) with a reagent including a catalytic metal ion, at least one distinguishably labeled incorporable nucleotide, and a polymerase, to produce a reaction mixture. As a result, the reversible terminator nucleotide incorporates into the primed template nucleic acid molecule to produce a blocked primed template nucleic acid molecule at each of the plurality of nucleic acid features, and there forms at each of the plurality of nucleic acid features a second stabilized ternary complex including the blocked primed template nucleic acid molecule and one of the distinguishably labeled incorporable nucleotides. There also is the step of (c) identifying cognate nucleotides for the primed template nucleic acid molecules at each of the plurality of nucleic acid features by detecting, in the reaction mixture, a label joined to the distinguishably labeled incorporable nucleotide of the second stabilized ternary complex. The at least one distinguishably labeled nucleotide analog is selected from the group consisting of:

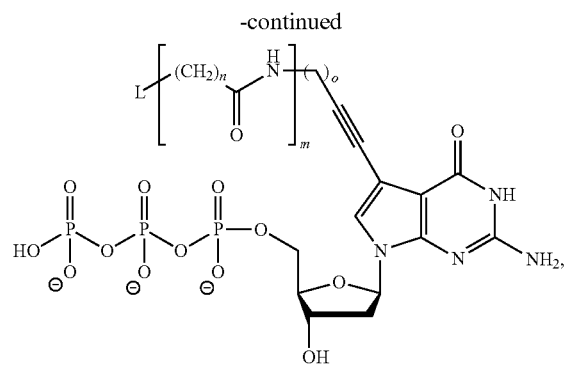

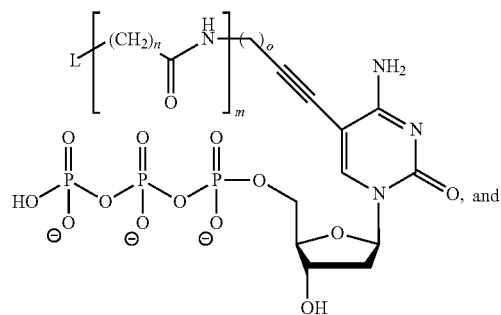

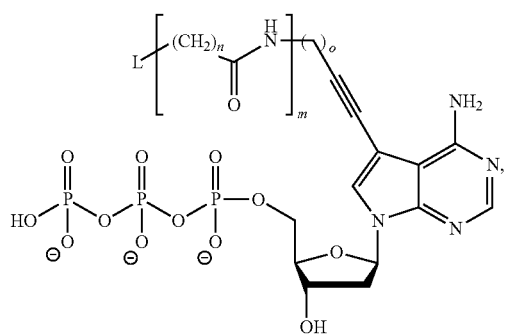

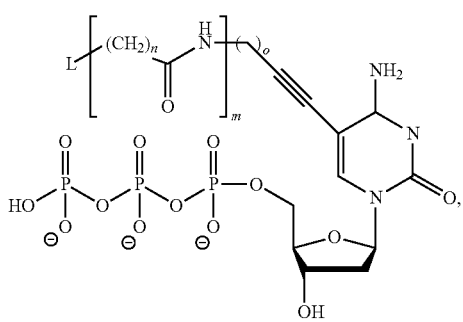

wherein L is a label moiety, n is any integer from 1 to 10, m is any integer from 1 to 5, and o is any integer from 1 to 10. Preferably, the at least one distinguishably labeled nucleotide analog is selected from the group consisting of:

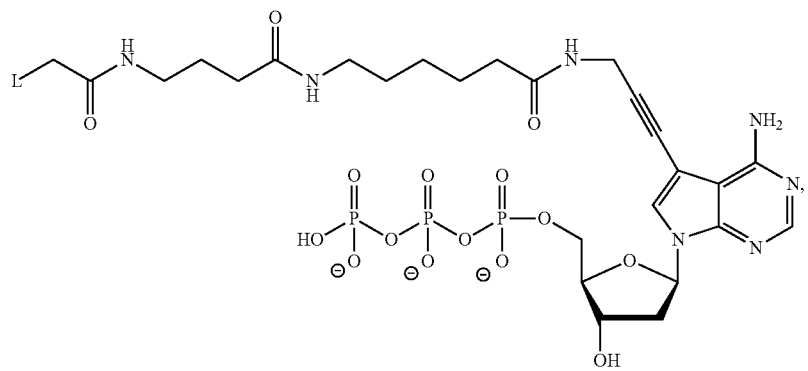
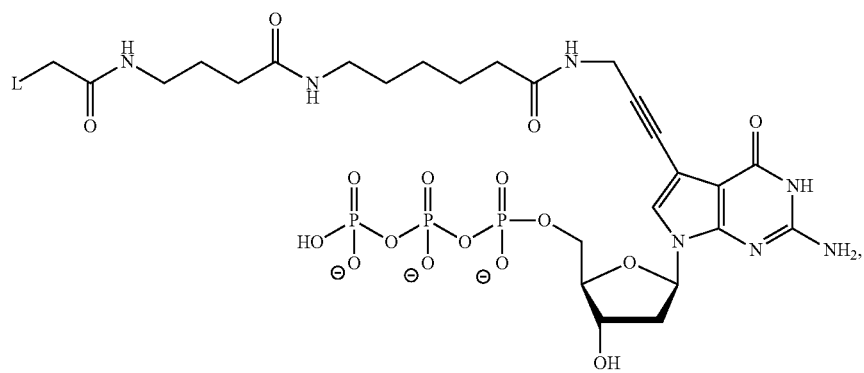
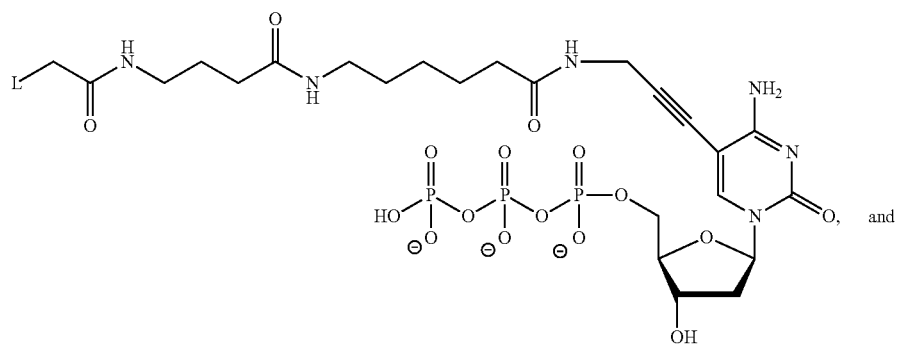
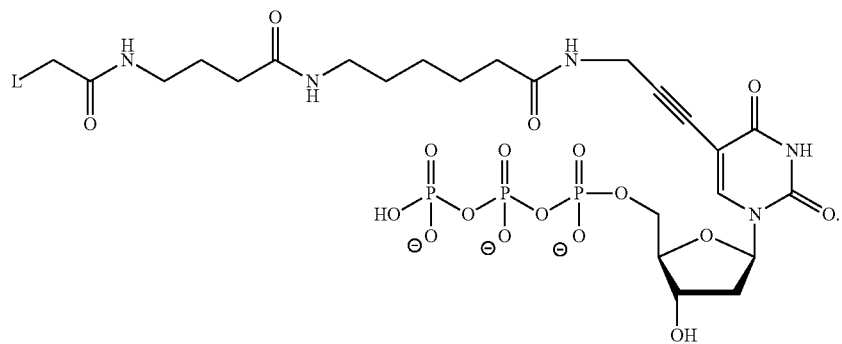

In another aspect, the disclosure relates to a stabilized ternary complex including a primed nucleic acid, polymerase and a labeled nucleotide analog selected from the group consisting of:

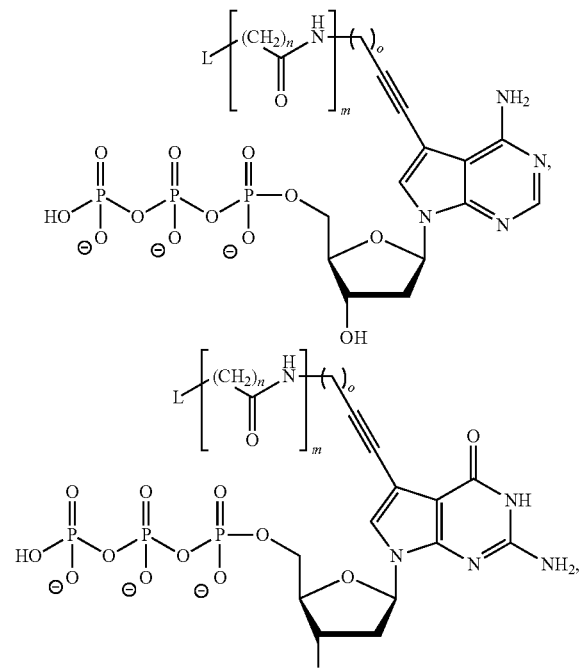

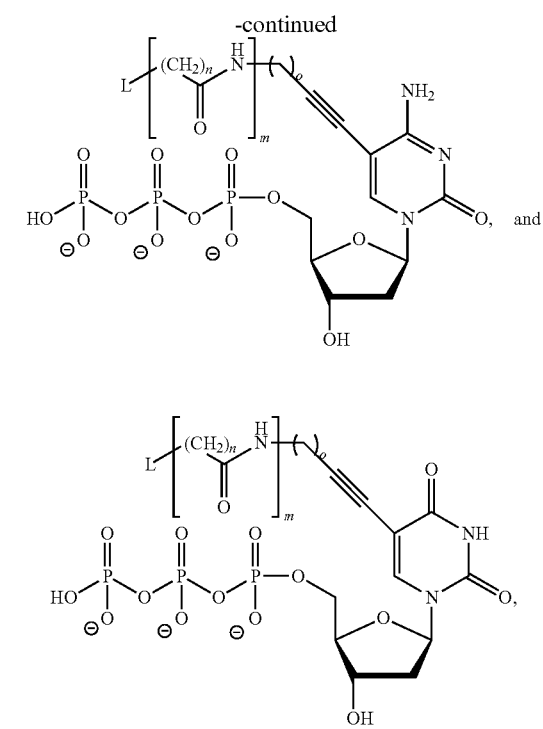

wherein L is a label moiety, n is any integer from 1 to 10, m is any integer from 1 to 5, and o is any integer from 1 to 10. Preferably, the labeled nucleotide analog is selected from the group consisting of:

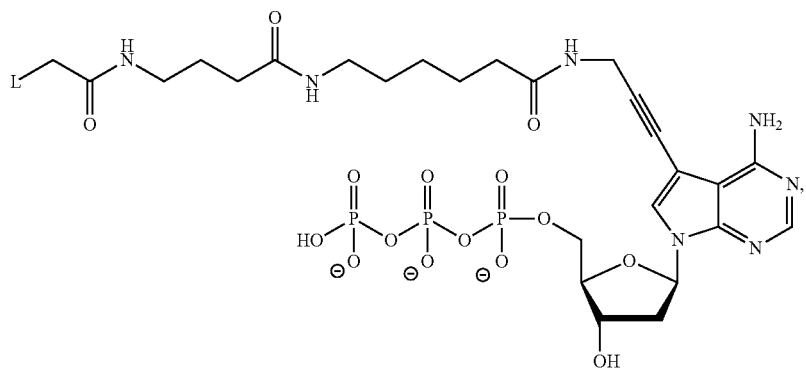

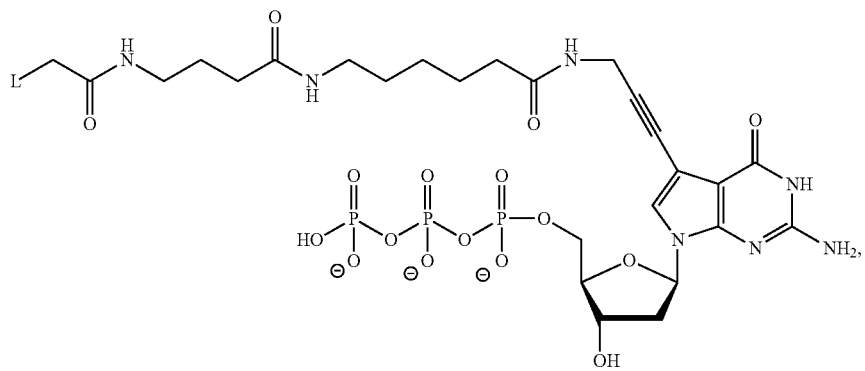

-continued

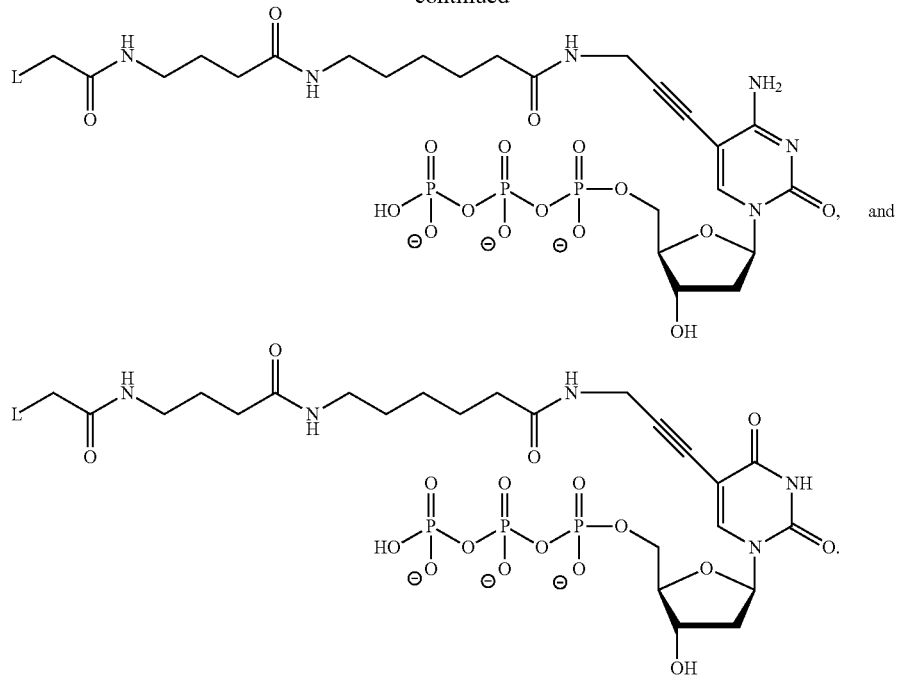

and

BRIEF DESCRIPTION OF THE DRAWINGS

FIGS. 5A-5B show results from a labeled nucleotide sequencing procedure employing decane as a stabilizing fluid during an imaging wash step. FIG. 5A shows a collection of fluorescent imaging results for a single bead. Columns represent images captured during imaging wash steps, where ternary complexes included dATP, dGTP, dCTP, and dTTP (each of these nucleotides being labeled with a fluorescent Cy5 moiety), respectively. Rows represent incremental steps that each lengthened blocked primed template nucleic acid molecules by a single nucleotide. FIG. 5B presents quantitative data obtained from the digital images of FIG. 5A. The highest magnitude signal among results from each set of four nucleotides indicates identity of the cognate nucleotide. Fluorescence intensities were measured in relative fluorescence units.

FIG. 6A shows fluorescent background signals obtained using air as a stabilizing fluid in an imaging wash step. FIG. 6B shows fluorescent background signals obtained using an aqueous pre-incorporation solution as a wash reagent during an imaging step. Fluorescence intensities were measured in relative fluorescence units.

DEFINITIONS

Figure 1:
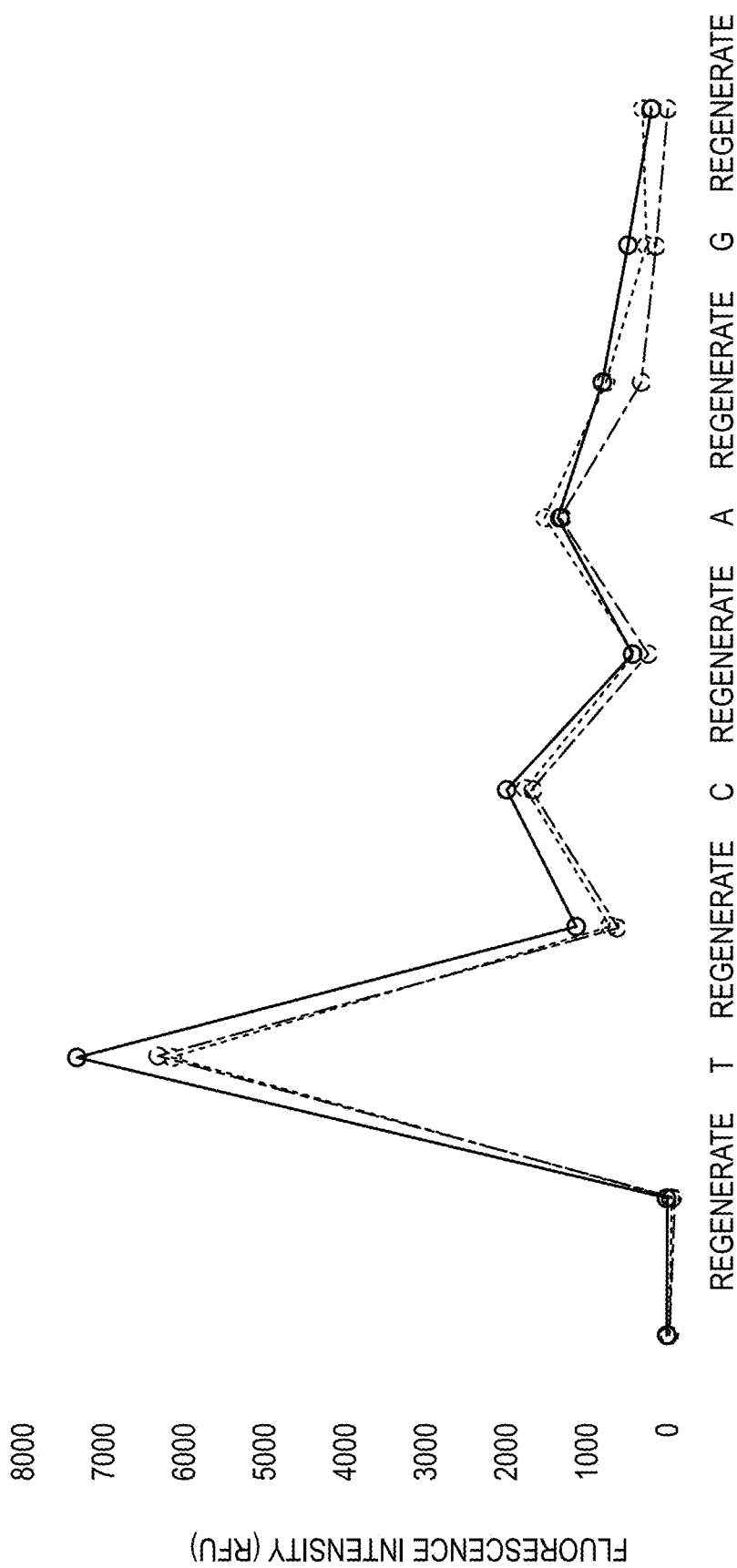
FIG. 1 is a graph showing background-subtracted fluorescent signal intensity (vertical axis) as a function of reaction cycles (horizontal axis). Identities of Cy-5 labeled nucleotides used in the procedure are indicated along the horizontal axis ("T" represents the Cy-5 labeled dTTP analog; "C" represents the Cy-5 labeled dCTP analog; "A" represents the Cy-5 labeled dATP analog; and "G" represents the Cy-5 labeled dGTP analog). "Regenerate" indicates timing of the regeneration solution wash that immediately preceded a contacting step using one of the fluorescent analogs in combination with an unlabeled reversible terminator analog of dATP. The incorporated reversible terminator nucleotide, once incorporated, remained in place through subsequent examination reactions.

Unless defined otherwise, all technical and scientific terms used herein have the same meaning as is commonly understood by one of ordinary skill in the art. For clarity, the following specific terms have the specified meanings. Other terms are defined in other sections herein.

The singular forms "a" "an" and "the" include plural referents unless the context clearly dictates otherwise. Approximating language, as used in the description and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the compositions, apparatus, or methods of the present disclosure. At the very least, each numerical parameter should at least be construed in light of the number of reported significant digits and by applying ordinary rounding techniques.

As used herein, "Sequencing By Binding" refers to a sequencing technique wherein specific binding of a polymerase to a primed template nucleic acid is used for identifying the next correct nucleotide to be incorporated into the primer strand of the primed template nucleic acid. The specific binding interaction precedes chemical incorporation of the nucleotide into the primer strand, and so identification of the next correct nucleotide can take place either without or before incorporation of the next correct nucleotide.

As used herein, the "next correct nucleotide" (sometimes referred to as the "cognate" nucleotide) is the nucleotide having a base complementary to the base of the next template nucleotide. The next correct nucleotide will hybridize at the 3'-end of a primer to complement the next template nucleotide. The next correct nucleotide can be, but need not necessarily be, capable of being incorporated at the 3' end of the primer. For example, the next correct nucleotide can be a member of a ternary complex that will complete an incorporation reaction or, alternatively, the next correct nucleotide can be a member of a stabilized ternary complex that does not catalyze an incorporation reaction. The next correct nucleotide can be a nucleotide analog such as a nucleotide analog shown in FIG. 2 or conforming to a Formula set forth below. A nucleotide having a base that is not complementary to the next template base is referred to as an "incorrect" (or "non-cognate") nucleotide. The next correct nucleotide, when participating in a ternary complex, is non-covalently bound to the primed template nucleic acid of the ternary complex.

As used herein, the position of the 3' terminal nucleotide of a primer represents position "N." Thus, "N+1" refers to the position of the first cognate nucleotide to be incorporated into the primer, while "N+2" refers to the position of the second cognate nucleotide to be incorporated into the primer.

As used herein, "stabilize," and its grammatical variants mean to hold steady or limit fluctuations. "Stabilizing" a complex refers to promoting or prolonging the existence of the complex or inhibiting disruption of the complex. The term can be applied to any of a variety of complexes including, but not limited to a binary complex or ternary complex. For example, the complex that is stabilized can be a ternary complex between a polymerase, primed template nucleic acid molecule (or blocked primed template nucleic acid) and cognate nucleotide. Generally, stabilization of the ternary complex prevents incorporation of the nucleotide component of the ternary complex into the primed nucleic acid component of the ternary complex. Accordingly, stabilizing a ternary complex can refer to promoting or prolonging non-covalent interactions that bind components of the ternary complex, or inhibiting disruption of non-covalent interactions that bind components of the ternary complex.

As used herein, "destabilize" and its grammatical variants mean to cause something to be unable to continue existing or working in its usual way. "Destabilizing" a complex refers to the process of promoting dissolution or breakdown of the complex (e.g., separation of the components of the complex). "Destabilizing" a complex also includes the process of inhibiting or preventing formation of the complex. The term can be applied to any of a variety of complexes including, but not limited to a binary complex or ternary complex. A ternary complex can be destabilized in a way that does not necessarily result in formation of a covalent bond between a primed template nucleic acid and next correct nucleotide. For example, destabilization can result in dissociation of one or more components from a ternary complex.

As used herein, a "salt providing monovalent cation" is an ionic compound that dissociates in aqueous solution to produce cations having a single positive charge. For example, the cations can be metal cations where the oxidation state +1.

As used herein, "a glutamate salt" is an ionic compound that dissociates in aqueous solution to produce glutamate anions.

As used herein, "nucleic acid" or "oligonucleotide" or "polynucleotide" means at least two nucleotides covalently linked together. Thus, the terms include, but are not limited to, DNA, RNA, analogs (e.g., derivatives) thereof or any combination thereof, that can be acted upon by a polymerizing enzyme during nucleic acid synthesis. The term includes single-, double-, or multiple-stranded DNA, RNA and analogs (e.g., derivatives) thereof. Double-stranded nucleic acids advantageously can minimize secondary structures that may hinder nucleic acid synthesis. A double stranded nucleic acid may possess a nick or a single-stranded gap. A nucleic acid may represent a single, plural, or clonally amplified population of nucleic acid molecules.

As used herein, the "next template nucleotide" (or the "next template base") refers to the nucleotide in a template nucleic acid that is located immediately 5' of the base in the template that is hybridized to the 3'-end of a hybridized primer.

As used herein, a "template nucleic acid" is a nucleic acid to be detected, sequenced, evaluated or otherwise analyzed using a method or apparatus disclosed herein.

As used herein, a "primed template nucleic acid" (or alternatively, "primed template nucleic acid molecule") is a template nucleic acid primed with (i.e., hybridized to) a primer, wherein the primer is an oligonucleotide having a 3'-end with a sequence complementary to a portion of the template nucleic acid. The primer can optionally have a free 5'-end (e.g., the primer being noncovalently associated with the template) or the primer can be continuous with the template (e.g., via a hairpin structure). The primed template nucleic acid includes the complementary primer and the template nucleic acid to which it is bound. Unless explicitly stated, a primed template nucleic acid can have either a 3' end that is extendible by a polymerase, or a 3' end that is blocked from extension. An "extendable primed template nucleic acid molecule" is extendable in a polymerization reaction.

As used herein, a "blocked primed template nucleic acid" (or alternatively, "blocked primed template nucleic acid molecule") is a primed template nucleic acid modified to preclude or prevent phosphodiester bond formation at the 3'-end of the primer. Blocking may be accomplished, for example, by chemical modification with a blocking group at either the 3' or 2' position of the five-carbon sugar at the 3' terminus of the primer. Alternatively, or in addition, chemical modifications that preclude or prevent phosphodiester bond formation may also be made to the nitrogenous base of a nucleotide. Reversible terminator nucleotide analogs including each of these types of blocking groups will be familiar to those having an ordinary level of skill in the art. Incorporation of these analogs at the 3' terminus of a primer of a primed template nucleic acid molecule results in a blocked primed template nucleic acid molecule. The blocked primed template nucleic acid includes the complementary primer, blocked from extension at its 3'-end, and the template nucleic acid to which it is bound.

As used herein, "polymerase" refers to a protein or other molecule that forms a ternary complex with a cognate nucleotide and primed template nucleic acid (or blocked primed template nucleic acid) including but not limited to, DNA polymerase, RNA polymerase, reverse transcriptase, primase and transferase. Typically, the polymerase includes one or more active sites at which nucleotide binding may occur. Optionally a polymerase includes one or more active sites at which catalysis of nucleotide polymerization may occur. Optionally a polymerase lacks catalytic nucleotide polymerization function, for example, due to a modification such as a mutation or chemical modification. Alternatively, the polymerase may catalyze the polymerization of nucleotides to the 3'-end of a primer bound to its complementary nucleic acid strand. For example, a polymerase catalyzes the addition of a next correct nucleotide to the 3'-oxygen of the primer via a phosphodiester bond, thereby chemically incorporating the nucleotide into the primer. Optionally, the polymerase used in the provided methods is a processive polymerase. Optionally, the polymerase used in the provided methods is a distributive polymerase.

As used herein, "extension" refers to the process after an oligonucleotide primer and a template nucleic acid have annealed to one another, wherein a polymerase enzyme catalyzes addition of one or more nucleotides at the 3'-end of the primer.

As used herein, a "nucleotide" is a molecule that includes a nitrogenous base, a five-carbon sugar (e.g., ribose or deoxyribose), and at least one phosphate group or functional analogs of such a molecule. The functional analogs may have a function of forming a ternary complex with a polymerase and primed template nucleic acid (or blocked primed template nucleic acid) and/or a function of being incorporated into a primed template nucleic acid. The term embraces ribonucleotides, deoxyribonucleotides, nucleotides modified to include exogenous labels or reversible terminators, and nucleotide analogs.

As used herein, a "test nucleotide" is a nucleotide being investigated for its ability to participate in formation of a ternary complex that further includes a primed template nucleic acid (or blocked primed template nucleic acid) and a polymerase.

As used herein, a "native" nucleotide refers to a naturally occurring nucleotide that does not include an exogenous label (e.g., a fluorescent dye, or other label) or chemical modification such as may characterize a nucleotide analog. Examples of native nucleotides useful for carrying out the Sequencing By Binding™ procedures described herein include: dATP (2'-deoxyadenosine-5'-triphosphate); dGTP (2'-deoxyguanosine-5'-triphosphate); dCTP (2'-deoxycytidine-5'-triphosphate); dTTP (2'-deoxythymidine-5'-triphosphate); and dUTP (2'-deoxyuridine-5'-triphosphate).

As used herein, a "nucleotide analog" has one or more modifications, such as chemical moieties, which replace, remove and/or modify any of the components (e.g., nitrogenous base, five-carbon sugar, or phosphate group(s)) of a native nucleotide. Nucleotide analogs may be either incorporable or non-incorporable by a polymerase in a nucleic acid polymerization reaction. Optionally, the 3'-OH group of a nucleotide analog is removed, replaced with a different moiety or modified with a moiety. The moiety may be a 3' reversible or irreversible terminator of polymerase extension. The base of a nucleotide may be any of adenine, cytosine, guanine, thymine, or uracil, or analogs thereof. Optionally, a nucleotide has an inosine, xanthine, hypoxanthine, isocytosine, isoguanine, nitropyrrole (including 3-nitropyrrole) or nitroindole (including 5-nitroindole) base. Nucleotides may include, but are not limited to, ATP, UTP, CTP, GTP, ADP, UDP, CDP, GDP, AMP, UMP, CMP, GMP, dATP, dTTP, dUTP, dCTP, dGTP, dADP, dTDP, dCDP, dGDP, dAMP, dTMP, dCMP, and dGMP. Nucleotides may also contain terminating inhibitors of DNA polymerase, dideoxynucleotides or 2',3' dideoxynucleotides, which are abbreviated as ddNTPs (ddGTP, ddATP, ddTTP, ddUTP and ddCTP).

As used herein, a "blocking moiety," when used in reference to a nucleotide analog, is a part of the nucleotide that inhibits or prevents the 3' oxygen of the nucleotide from forming a covalent linkage to a second nucleotide (e.g., via the 3' oxygen of the nucleotide analog when it is present at the 3' end of a primer) during the incorporation step of a nucleic acid polymerization reaction. The blocking moiety of a "reversible terminator" nucleotide can be removed from the nucleotide analog to allow for nucleotide incorporation. Such a blocking moiety is referred to herein as a "reversible terminator moiety." Exemplary reversible terminator moieties are set forth in U.S. Pat. Nos. 7,427,673; 7,414,116; and 7,057,026 and PCT publications WO 91/06678 and WO 07/123744, each of which is incorporated by reference.

As used herein, "monitoring" (or sometimes "measuring"), when used in reference to a molecular binding event, refers to a process of detecting a measurable interaction or binding between two molecular species. For example, monitoring may involve detecting measurable interactions between a polymerase and primed template nucleic acid (or blocked primed template nucleic acid), typically at various points throughout a procedure. Monitoring can be intermittent (e.g., periodic) or continuous (e.g., without interruption), and can involve acquisition of quantitative results. Monitoring can be carried out by detecting multiple signals over a period of time during a binding event or, alternatively, by detecting signal(s) at a single time point during or after a binding event.

As used herein, "contacting," when used in reference to chemical reagents, refers to the mixing together of reagents (e.g., mixing an immobilized template nucleic acid and either a buffered solution that includes a polymerase, or the combination of a polymerase and a test nucleotide) so that a physical binding reaction or a chemical reaction may take place.

As used herein, "incorporating" or "chemically incorporating," when used in reference to a nucleic acid and nucleotide, refers to the process of joining a cognate nucleotide to the 3'-end of a nucleic acid primer by formation of a phosphodiester bond.

As used herein, a "binary complex" is a complex between a polymerase and a primed template nucleic acid (or blocked primed template nucleic acid), where the complex does not include a nucleotide molecule such as the next correct nucleotide.

As used herein, a "ternary complex" is a complex between a polymerase, a primed template nucleic acid (e.g., blocked primed template nucleic acid), and the next correct nucleotide positioned immediately downstream of the primer and complementary to the template strand of the primed template nucleic acid (e.g., the blocked primed template nucleic acid). The primed template nucleic acid can include, for example, a primer with a free 3'-OH or a blocked primer (e.g., a primer with a chemical modification on the base or the sugar moiety of the 3' terminal nucleotide, where the modification precludes enzymatic phosphodiester bond formation).

As used herein, a "catalytic metal ion" refers to a metal ion that facilitates phosphodiester bond formation between the 3'-OH of a nucleic acid (e.g., a primer) and the phosphate of an incoming nucleotide by a polymerase. A "divalent catalytic metal cation" is a catalytic metal ion having a valence of two. Catalytic metal ions can be present at concentrations necessary to stabilize formation of a complex between a polymerase, a nucleotide, and a primed template nucleic acid, referred to as non-catalytic concentrations of a metal ion. Catalytic concentrations of a metal ion refer to the amount of a metal ion sufficient for polymerases to catalyze the reaction between the 3'-OH group of a nucleic acid (e.g., a primer) and the phosphate group of an incoming nucleotide.

As used herein, a "non-catalytic metal ion" refers to a metal ion that, when in the presence of a polymerase enzyme, does not facilitate phosphodiester bond formation needed for chemical incorporation of a nucleotide into a primer. Typically, the non-catalytic metal ion is a cation. A non-catalytic metal ion may inhibit phosphodiester bond formation by a polymerase, and so may stabilize a ternary complex by preventing nucleotide incorporation. Non-catalytic metal ions may interact with polymerases, for example, via competitive binding compared to catalytic metal ions. A "divalent non-catalytic metal ion" is a non-catalytic metal ion having a valence of two. Examples of divalent non-catalytic metal ions include, but are not limited to, $Ca^{2+}$, $Zn^{2+}$, $Co^{2+}$, and $Sr^{2+}$. The trivalent $Eu^{3+}$ and $Tb^{3+}$ ions are non-catalytic metal ions having a valence of three.

As used herein an "exogenous label" refers to a detectable chemical moiety of a molecule (e.g., a sequencing reagent) that is not present in a natural analog of the molecule (e.g., sequencing reagent), such as a non-naturally occurring label present on a synthetic nucleotide analog or a synthetic polymerase analog (e.g., a DNA polymerase). While a native dNTP may have a characteristic limited fluorescence profile, the native dNTP does not include any added colorimetric or fluorescent moiety. Conversely, a dATP (2'-deoxyadenosine-5'-triphosphate) molecule modified to include a chemical linker and fluorescent moiety attached to the gamma phosphate would be said to include an exogenous label because the attached chemical components are not ordinarily a part of the nucleotide. Of course, chemical modifications to add detectable labels to nucleotide bases also would be considered exogenous labels. Likewise, a DNA polymerase modified to include a fluorescent dye (e.g., by attachment to a cys residue that is part of the primary sequence of the enzyme) also would be said to include an exogenous label because the label is not ordinarily a part of the polymerase.

As used herein, "unlabeled" refers to a molecular species free of added or exogenous label(s) or tag(s). Of course, unlabeled nucleotides will not include either of an exogenous fluorescent label, or an exogenous Raman scattering tag. A native nucleotide is another example of an unlabeled molecular species. An unlabeled molecular species can exclude one or more of the labels set forth herein or otherwise known in the art relevant to nucleic acid sequencing or analytical biochemistry.

As used herein, a "flow cell" is a reaction chamber that includes one or more channels that direct fluid in a predetermined manner to conduct a desired reaction. The flow cell can be coupled to a detector such that a reaction occurring in the reaction chamber can be observed. For example, a flow cell can contain primed template nucleic acid molecules (or blocked primed template nucleic acid molecules), for example, tethered to a solid support, to which nucleotides and ancillary reagents are iteratively applied and washed away. The flow cell can include a transparent material that permits the sample to be imaged after a desired reaction occurs. For example, a flow cell can include a glass slide containing small fluidic channels, through which polymerases, dNTPs and buffers can be pumped. The glass inside the channels can be decorated with one or more primed template nucleic acid molecules to be sequenced. An external imaging system can be positioned to detect the molecules on the surface of the glass. Reagent exchange in a flow cell is accomplished by pumping, drawing, or otherwise "flowing" different liquid reagents through the flow cell. Exemplary flow cells, methods for their manufacture and methods for their use are described in US Pat. App. Publ. Nos. 2010/0111768 A1 or 2012-0270305 A1; or WO 05/065814, each of which is incorporated by reference herein.

As used herein, a "reaction vessel" is a container that isolates one reaction (e.g., a binding reaction; an incorporation reaction; etc.) from another, or that provides a space in which a reaction can take place. Non-limiting examples of reaction vessels useful in connection with the disclosed technique include: flow cells, wells of a multiwell plate; microscope slides; tubes (e.g., capillary tubes); etc. Features to be monitored during binding and/or incorporation reactions can be contained within the reaction vessel.

As used herein, "library" refers to a collection of analytes having different chemical compositions. Typically, the analytes in a library will be different species having a common feature or characteristic. For example, a library can include nucleic acid species that differ in nucleotide sequence, but that are similar with respect to having a sugar-phosphate backbone.

As used herein, a "feature" is a point, area or volume of a material (e.g., a patterned or random array) that can be distinguished from other points or areas according to relative location. An individual feature can include one or more molecules of a particular type. For example, a feature can include a single target nucleic acid molecule having a particular sequence, or a feature can include an ensemble of several nucleic acid molecules having the same sequence and/or complementary sequence thereof. Different molecules that are at different features of a pattern can be distinguished from each other according to the locations of the features in the pattern. Exemplary features include without limitation, wells in a substrate, beads (or other particles) in or on a substrate, projections (e.g., in situ generated nucleic acid amplification products) from a substrate, pads of gel material on a substrate, or channels in a substrate.

As used herein, "population" refers to a collection of things that are processed together. The collection of things can be in some way related to each other (e.g., nucleic acids of the same or different sequences). A "population of nucleic acid features" refers to a collection of nucleic acid features that are processed together (e.g., in a flow cell or in a well of a multiwell plate). Individuals among the collection may be single nucleic acid molecules (e.g., RCA amplification products), or a collection of homogenous nucleic acid molecules. Individual features can be distinguished from each other within or among the population. To determine the identity of a next correct nucleotide for "a population of nucleic acid features" comprising primed template nucleic acid molecules (or blocked primed template nucleic acid molecules) means to establish identity of the next correct nucleotide for the features that make up the population. As examples, populations of target nucleic acids may be represented by a collection of beads or in situ generated nucleic acid amplification products.

As used herein, a "population binding product" refers to the product that results from a binding reaction (e.g., that may or may not result in formation of complexes) that involves a population. Thus, the term can refer to the product (e.g., the aggregated collection of features) that results from contacting a population of features comprising primed template nucleic acid molecules (or blocked primed template nucleic acid molecules) with a polymerase and a test nucleotide, where some features among the population may form ternary complexes, while others may not.

As used herein, a "complex" is a molecular entity formed by non-covalent association involving two or more component molecular entities (e.g., a polymerase and either a primed template nucleic acid molecule or blocked primed template nucleic acid molecule).

As used herein, "imaging" refers to a process for obtaining a representation of a sample or a portion thereof. The process may involve acquisition of optical data, such as the relative location of a feature undergoing analysis, and intensity of an optical signal produced at the position of the feature.

As used herein, "equilibrium" and "dynamic equilibrium" generally refer to a state of balance due to the equal action of opposing forces (e.g., equal, opposite rates). For example, a ternary complex formed between an immobilized primed template nucleic acid, a polymerase, and a cognate nucleotide is in "dynamic equilibrium" with unbound polymerase and cognate nucleotide when the rate of formation of the ternary complex is balanced by the rate of its dissolution. Under this condition, the reversible binding reaction ceases to change its ratio of products/reactants. If the rate of a forward reaction (e.g., ternary complex formation) is balanced by the rate of a reverse reaction (e.g., ternary complex dissociation), then there is no net change.

As used herein, an "intercalating dye" is a chemical compound with high affinity for DNA, where the compound binds or inserts between the planar base pairs of a nucleic acid double helix and changes its spectral properties as a consequence. In the context of the present disclosure, the term further embraces minor groove binding dyes, and major groove binding dyes that change fluorescent properties, for example by increasing fluorescence emission, because of the binding.

As used herein, "energy transfer relationship" refers to a relationship between two labels (e.g., a "donor" and an "acceptor") held sufficiently close that energy emitted by one label can be received or absorbed by the other label. The "donor" is the moiety that initially absorbs the energy, and the "acceptor" is the moiety to which the energy is subsequently transferred. An "energy transfer partner" refers to one member of the pair of interactive labels (i.e., the donor and acceptor), without specifying whether the member functions as the donor or acceptor.

As used herein, "FRET" (i.e., fluorescence resonance energy transfer) refers to the distance-dependent transmission of energy quanta from the site of absorption to the site of its utilization in a molecule or system of molecules by resonance interaction between chromophores.

As used herein, "available for polymerization" refers to a molecular species (e.g., a primed template nucleic acid) that is competent for participating as a substrate in a polymerization reaction. Removing a reversible terminator moiety from the nucleotide at the 3'-end of a blocked primed template nucleic acid molecule (e.g., in a "deblocking" reaction) renders the resulting molecule "available for polymerization" if that molecule can participate in an enzymatic reaction involving phosphodiester bond formation with a cognate nucleotide.

The terms "cycle" or "round," when used in reference to a sequencing procedure, refer to the portion of a sequencing run that is repeated to indicate the presence of a nucleotide. Typically, a cycle or round includes several steps such as steps for delivery of reagents, washing away unreacted reagents and detection of signals indicative of changes occurring in response to added reagents.

As used herein, a "non-transient" record is a record of results or information, where the record persists in time. A non-transient record can be stored and then referenced or retrieved at a later time. Non-limiting examples of non-transient recordings include printed information (e.g., paper records), electronically recorded information disposed on a computer-readable medium or storage device (e.g., a flash drive, disk drive, floppy disk, etc.), or otherwise recorded on a machine-readable form, such as a bar code for storing numerical values.

As used herein, to perform a "reagent exchange" means to substitute or replace one reagent (e.g., a liquid reagent) with something else. For example, a reagent exchange may involve flowing one liquid reagent through a flow cell to replace a different reagent that already is or was present in the flow cell. An optional wash step can occur between the exchange of reagents, but need not occur in all embodiments. Alternatively, a probe (e.g., an optical interferometry probe) derivatized with a nucleic acid undergoing testing can be transferred from a reservoir containing one reagent to a different reservoir containing a different reagent. In yet another example, reagent exchange can be carried out using robotic liquid handling to remove one liquid reagent contained in a well of a multiwell plate, and to replace it with a volume of a different liquid reagent. In all cases, the composition of a reaction mixture will be different before and after the reagent exchange such that the first mixture, existing in a vessel prior to reagent exchange, will be understood to be different from the second mixture that results in the vessel after the reagent exchange.

As used herein, a "ternary complex-stabilizing agent" is any agent that promotes or maintains stability of a ternary complex that includes: either a primed template nucleic acid molecule or a blocked primed template nucleic acid molecule; a polymerase; and a cognate nucleotide (i.e., the next correct nucleotide). Examples include: a non-catalytic metal ion that inhibits polymerization (e.g., $Ca^{2+}$, $Zn^{2+}$, $Co^{2+}$, $Ni^{2+}$, and $Sr^{2+}$), trivalent lanthanide cations (e.g., $Eu^{3+}$ and $Tb^{3+}$); polymerases engineered to have reduced capacity for binary complex formation while exhibiting ternary complex formation capacity; polymerases engineered for complete loss of ability to catalyze phosphodiester bond formation in the presence of $Mg^{2+}$ ion.

As used herein, a "fluid" is a substance, as a liquid or a gas, that is capable of flowing and that changes its shape to fill a vessel. In many conditions, a fluid will change shape at a steady rate when acted upon by a force tending to change its shape.

As used herein, a "stabilizing fluid" is a fluid that can contact a ternary complex without substantially promoting decomposition, dissolution, or loss of polymerase or nucleotide from the complex. Preferred stabilizing fluids are free of nucleotide and/or polymerase component(s) (e.g., labeled nucleotide and/or labeled polymerase) that participate in the formation of ternary complexes. Optionally, neither nucleotides nor polymerases are substantially soluble in the stabilizing fluids so that components (e.g., nucleotide and polymerase) of an immobilized ternary complex do not partition into the bulk phase of the stabilizing fluid. For example, an immobilized ternary complex formed in the presence of a reagent solution that includes a polymerase and cognate nucleotide may not partition into the bulk phase of a stabilizing fluid that replaces the reagent solution (e.g., by fluid flow through a flow cell), or substitutes in its place. Examples of stabilizing fluids include, without limitation: air, gas, silicone oils, mineral oils, alcohols (e.g., ethanol and isopropanol), and alcohol-containing solutions that do not substantially solubilize polymerases or nucleotides. Gases that are inert to reagents and other components used in a reaction of the present disclosure can be particularly useful including, for example, nitrogen, argon, helium or neon.

As used herein, "stable for detection" refers to a condition wherein a ternary complex can be detected because it has not dissociated. Typically, a population of similar or identical ternary complexes will be considered stable for detection when a sufficient number or fraction remain as intact, and a signal indicating the presence of the complexes can be detected. A ternary complex that dissociates into its constituent parts is not stable for detection.

As used herein, a "non-aqueous fluid" is a fluid that is free of water. Examples of non-aqueous fluids would be air and oils (e.g., silicone oil or mineral oil).

As used herein, "miscible" is a term describing two fluids that form a homogeneous mixture or solution when added together.

As used herein, "immiscible" is a term describing two fluids or liquids (including, for example, one fluid that is a liquid and a second that is not) that do not form a homogenous substance when mixed together under particular conditions. One fluid may be soluble in another fluid at low concentrations such that the fluid is immiscible with the other fluid over a solubility limit. For example, air is immiscible with water or other aqueous liquids above a solubility limit defined by Henry's Law. Likewise, silicone oil (e.g., having a polymer backbone of alternating silicon and oxygen atoms) is immiscible with water and aqueous liquids (e.g., liquids containing nucleotides and polymerases) when present in an amount above solubility limits. One useful category of fluids useful for performing washes or flush steps includes "water-immiscible fluids."

As used herein, a "variant" of a polypeptide reference sequence is a form or version of the polypeptide sequence that differs in some respect. Variants can differ in amino acid sequence and can include, for example, amino acid substitutions, additions (e.g., insertions, and extensions of termini), and deletions. A variant of a polypeptide reference sequence can include amino acid substitutions and/or internal additions and/or deletions and/or additional amino acids at one or both termini of the reference sequence.

As used herein, the term "solid support" refers to a rigid substrate that is insoluble in aqueous liquid. The substrate can be non-porous or porous. The substrate can optionally be capable of taking up a liquid (e.g., due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers.

As used herein, the term "diffusional exchange," when used in reference to a member of a binding complex, refers to the ability of the member to move in or through a fluid to associate and dissociate from another member of the complex. Diffusional exchange can occur when there are no barriers that prevent the members from interacting with each other to form a complex. However, diffusional exchange is understood to exist even if diffusion is retarded, reduced or altered so long as access is not absolutely prevented.

As used herein, the term "transport" refers to movement of a molecule through a fluid. The term can include passive transport such as movement of molecules along their concentration gradient (e.g., passive diffusion). The term can also include active transport whereby molecules can move along their concentration gradient or against their concentration gradient. Thus, transport can include applying energy to move one or more molecule in a desired direction or to a desired location such as an amplification site. Transport can occur, for example, within a single fluid phase, between a solid phase and fluid phase, or between a first fluid phase and a second fluid phase.

As used herein, a complex that is "transient" in nature, or that forms "transiently," is a complex in dynamic equilibrium with reagents in its environment so that the complex is in a state of formation and dissociation at the same time. Thus, formation of the complex can be considered "reversible."

As used herein, "reversible association" when used in reference to a multicomponent complex (e.g., a binary complex or a ternary complex) means that the complex is in a state of formation and dissociation. When the quantity of the multicomponent complex is constant, the rate of formation and the rate of dissociation are balanced and the complex is in equilibrium with the chemical components of its surroundings.

As used herein, an "imaging wash" step refers to a process that involves contacting a fluid to a vessel or solid support that has one or more multi-component complexes (e.g., binary or ternary complexes), and imaging the complexes while they are in contact with the fluid or otherwise in the presence of the fluid. The process can take place within a flow cell, within a well of a multiwell plate, or in or on any other vessel appropriate for containing the complexes. In some embodiments, the imaging wash step is conducted using a flow cell. Preferably, the fluid used in the imaging wash step is a stabilizing fluid.

As used herein, the term "replace," when used in reference to two fluids, means removing most or all of a first fluid and adding a second fluid in place of the removed first fluid. For example, at least 75%, 80%, 90%, 95%, 99%, 99.9% or 100% of the first fluid can be removed.

As used herein, a "kit" is a packaged unit containing one or more components that can be used for performing detection and/or sequencing reactions. Typical kits may include packaged combinations, in one or more containers or vials, of reagents to be used in the procedure.

DETAILED DESCRIPTION

Introduction

Described herein is a rapid and efficient procedure permitting identification of cognate nucleotides among members of a population of primed template nucleic acid molecules. As detailed below, this can be accomplished in different ways.

Generally speaking, the disclosed technique can rely on formation of a reversible complex (i.e., a ternary complex) under conditions wherein a polymerase and nucleotide contact a primed template nucleic acid that is blocked from extension at the 3'-end of its primer. The blocked primed template nucleic acid molecule can be immobilized to a solid support to facilitate the workflow. The extent of ternary complex formation reflects an equilibrium binding condition resulting from the presence of the different binding components (i.e., polymerase and cognate nucleotide) at their associated concentrations. Although the net effect of equilibrium is that complexes that form appear to be stable during this binding step, individual complexes actually are in a state of flux. Indeed, components of the complex are continuously associating and dissociating with the blocked primed template nucleic acid molecule. The term "dynamic equilibrium" is used herein to reflect this dynamic process. The optional step of washing ternary complexes using a stabilizing fluid prior to detection changes the chemical environment containing the ternary complexes. This means that the ternary complexes formed under one condition can be detected under a different condition. For example, the stabilizing fluid can slow the dissociation of ternary complexes that otherwise occurs in the absence of one or more binding components (e.g., nucleotide and/or polymerase), thereby allowing detection of the ternary complexes over an extended timeframe.

Optionally, ternary complexes including a primed template nucleic acid molecule, a cognate nucleotide (optionally including a detectable label), and a polymerase (optionally including a detectable label) are detected during a wash step. The wash step can be an imaging wash step employing a stabilizing fluid that slows dissociation of the complexes while permitting removal of labeled components (e.g., labeled nucleotides) from the system, thereby preserving the complexes for detection. Accordingly, ternary complexes formed within a flow cell can be detected while in contact with the stabilizing fluid (sometimes referred to as an "imaging fluid" or "imaging buffer"), and substantially in the absence of non-complexed labeled binding components (i.e., nucleotides and/or polymerase) that would undesirably increase background signals. Thus, detecting ternary complexes during an imaging wash step involves detecting the complexes under changed conditions (e.g., non-equilibrium conditions) because there is substantially no forward reaction leading to ternary complex formation.

Washing ternary complexes by flowing a nucleotide-free and polymerase-free stabilizing fluid through a flow cell can remove non-complexed labeled nucleotide and polymerase and reduce non-specific background signals (e.g., fluorescent background) while still preserving detectability of the pre-formed or existing ternary complexes. For example, ternary complexes contained within a flow cell can remain stable for detection in the stabilizing fluid after a period of contact with the stabilizing fluid of between 1-10 minutes, or between 1-5 minutes, or between 2-5 minutes, or between 3-5 minutes, or even after more than 10 minutes. Notwithstanding these durations of stability, it may be desirable to detect the stabilized ternary complexes after a shorter time period. For example, to increase cycle processing speed it may be desirable to detect ternary complexes after only 10-60 seconds, or after only 30-60 seconds following a period of contact with a stabilizing fluid that is between 1-10 minutes, or between 1-5 minutes, or between 2-5 minutes, or between 3-5 minutes, or even after more than 10 minutes, where the stabilizing fluid renders contacted ternary complexes stable for detection.

Optionally, the technique can be carried out using single-scan detection, where each of a plurality of distinguishably labeled nucleotides is detected in one step. For example, dynamic equilibrium binding of four distinguishable nucleotides (e.g., at least some harboring exogenous labels) can be detected in a single step following co-delivery of: (1) incorporable reversible terminator nucleotides; and (2) labeled nucleotides that are not incorporated. Optionally, the reversible terminator nucleotides of the co-delivered mixture are unlabeled reversible terminators. The labeled nucleotides that are not incorporated optionally are labeled non-incorporable nucleotide analogs. Examples of useful labeled nucleotides include, but are not limited to those shown in FIG. 2 or conforming to a Formula set forth below. The disclosed approach can eliminate the need for separate steps to incorporate reversible terminators and then detect labeled nucleotide interaction using a blocked primed template nucleic acid molecule. In some embodiments, the enzymatic joining of the reversible terminator nucleotide and detection of the noncovalent association or binding of a detectably labeled nucleotide both take place in the same reaction mixture.

The compositions and methods used in several embodiments set forth herein exploit the binding specificity of a ternary complex that includes a polymerase, a primed template nucleic acid molecule blocked from extension of the primer strand, and a cognate nucleotide in the presence of a catalytic metal ion. This specificity can be used to identify the next correct nucleotide for the primed template nucleic acid by identifying the nucleotide present in the ternary complex. By this approach, blocking the primer from extension at its 3'-end, and then detecting formation of a ternary complex containing a labeled nucleotide without phosphodiester bond formation, optionally under equilibrium binding conditions, can occur in the same reaction mixture and without intervening reagent exchange or wash steps. Alternatively, formation of a ternary complex including a blocked primed template nucleic acid molecule and a labeled nucleotide can be detected during an imaging wash step when the supply of free labeled nucleotides has been removed from the system (i.e., when the number of ternary complexes is no longer increasing). The presence of catalytic metal ions during the examination procedure that detects ternary complexes may even mimic a more natural ternary complex condition, and so provides an added benefit over methods that omit or replace catalytic ions. The aggregated result is increased speed of single nucleotide identification, and of extensive sequencing protocols based on repeated cycles of cognate nucleotide identification.

In certain embodiments, nucleotide-containing reagent delivered to a population or ensemble of primed template nucleic acids includes: (a) a polymerase; (b) four types of reversible terminator nucleotides; (c) four types of distinguishably labeled nucleotides; and (d) a catalytic metal ion. The components can be delivered as a single reagent or, alternatively, one or more components can be added sequentially to form the reagent in the presence of the primed template nucleic acid. The primed template nucleic acids undergoing sequence analysis can be features immobilized within a flow cell. Exemplary features include nucleic acid amplification products (which may be generated in situ or ex situ), or beads harboring nucleic acids. As indicated above, the reversible terminator nucleotides can be unlabeled. In other embodiments, the reversible terminator nucleotides include a detectable label, such as a fluorescent label or a Raman label. The distinguishably labeled nucleotides used in the procedure optionally are nucleotide analogs that cannot be acted upon by a polymerase to covalently link to the primed template nucleic acid molecule via a phosphodiester bond (i.e., so-called "non-incorporable" nucleotides). Alternatively, the nucleotides examined in the procedure (i.e., nucleotides that bind in a ternary complex without incorporating) are detectably labeled incorporable nucleotides that are present along with reversible terminator nucleotides in the reaction mixture, but the reversible terminator nucleotides incorporate preferentially. In yet another alternative, the procedure is performed using reversible terminator nucleotides that incorporate, and that also can be detected in a ternary complex without incorporation.

As set forth in further detail below, positioning a label moiety and a reversible terminator moiety on separate nucleotides that are cognate for the same template base, where only the nucleotide carrying the reversible terminator moiety is incorporated into the primed template nucleic acid molecule, and where the detectable label identifies the cognate nucleotide, simplifies chemical reagent processing while allowing multiple different ternary complexes to be evaluated in parallel. For example, a single reaction mixture that includes reversible terminator nucleotides (e.g., unlabeled reversible terminator nucleotides); detectably labeled nucleotides that are not incorporated (e.g., labeled non-incorporable nucleotides); one or more polymerases; and a catalytic metal ion can be used to incorporate the reversible terminators and permit dynamic formation of ternary complexes that include the labeled nucleotide. As well, detecting ternary complexes containing the labeled cognate nucleotide in the same reaction mixture that incorporated reversible terminator nucleotides streamlines workflow not only by eliminating separate enzymatic steps, but also by eliminating the requirement for an intervening wash step. Moreover, specificity of ternary complex formation permits multiple different complexes to be in fluid communication with each other in a reaction vessel, such as a microarray or flow cell, while being analyzed in a detection method such as a fluorescence detection method (e.g., fluorometry).

Certain aspects of the disclosed technique rely on the fact that only one of the two types of nucleotides present in a reaction mixture (i.e., reversible terminator nucleotides, and non-incorporable nucleotides) will be incorporated into an available primed template nucleic acid molecule. This extension reaction increments the primer forward by a single nucleotide, at which point incorporation ceases. Nucleotides remaining in the reaction mixture are free to bind to the reversibly terminated primer in dynamic equilibrium. When the incorporated reversible terminator nucleotide is free of exogenous detectable labels (e.g., added fluorescent moieties, Raman scattering labels, etc.), only non-incorporable, distinguishably labeled nucleotides harbor labels that can be detected (e.g., labeled nucleotides present in ternary complexes). Success of the technique can be achieved via detection of binding of non-incorporable, distinguishably labeled nucleotides when there is competition for binding by reversible terminator nucleotides that were not incorporated. Surprisingly, this is the case. More particularly, reversible binding of labeled nucleotide was easily detected in the presence of the reversible terminator nucleotide, even though both types of nucleotide may have the same cognate nucleotide specificity. Delivery of reversible terminator nucleotides and non-incorporable nucleotides as a single reagent can simplify procedural workflows.

Generally speaking, the disclosed techniques do not share restrictions on detectable labels that characterize certain other techniques used in the DNA sequencing field. For example, there is no requirement for a label (e.g., a FRET partner) to be present on the polymerase or primed template nucleic acid. Indeed, in certain embodiments the polymerase is unlabeled, or does not generate any signal used for identifying cognate or non-cognate nucleotide. The polymerase preferably does not transfer energy to the labeled nucleotide to render it detectable by the detection apparatus used for carrying out the technique. The label or dye of the detectable nucleotides employed in the procedure preferably is not an intercalating dye (e.g., not an intercalating dye disclosed in U.S. Pat. No. 8,399,196), that changes its signal-generating properties (e.g., fluorescent output) upon binding DNA. As well, the label or dye present on the labeled nucleotide need not be a conformationally sensitive dye that changes spectral properties when it is the cognate nucleotide present in a ternary complex.

In some aspects the disclosed technique achieves rapid processing, in part, because extension of the primer and detection of dynamic nucleotide binding that indicates cognate nucleotide identity occur in the same reaction mixture, without intervening washes or reagent exchanges between those steps. As well, the ability to incorporate four types of reversible terminator nucleotides, and to process four distinguishable nucleotides during the examination step (i.e., without incorporation) makes it possible to employ single-scan imaging techniques. Still further, there can be enhancement of reaction efficiency or yield since it is only necessary to chemically cleave one covalent bond during each cycle of nucleotide binding and identification. This is because detectable label associates with the primed template nucleic acid molecule in a ternary complex noncovalently. In some embodiments, the non-incorporated nucleotide of the ternary complex that includes the blocked primer can be removed by a simple wash step that also cleaves the reversible terminator moiety from the blocked primed template nucleic acid molecule.

General features of the Sequencing By Binding™ technique, together with details concerning various aspects of methods employing single-scan imaging are provided below. It will be understood that the apparatus and methods set forth herein need not be limited to nucleic acid sequencing. For example, this disclosure provides methods for interrogating a single nucleotide site in a primed template nucleic acid. Interrogation of a single nucleotide site can be useful for detecting a variant at a single site (e.g., a single nucleotide polymorphism or SNP), for example, in a genotyping method. Typically, a genotyping method is carried out using a template nucleic acid with a known genetic locus, but for which an allelic variation at the locus is to be determined. Alternatively, identification of a single nucleotide site can be useful for evaluating characteristics of a target polymerase, such as specificity of the polymerase for binding to a correct nucleotide. Methods that interrogate only a single nucleotide site can be carried out using a single cycle of a Sequencing By Binding™ method set forth herein. Optionally, a single nucleotide site can be interrogated using methods or reagents (e.g., nucleotides shown in FIG. 2 or conforming to Formulas below) of the present disclosure in combination with methods or reagents set forth in commonly owned U.S. patent application Ser. No. 15/701,373 and U.S. provisional application having Ser. No. 62/448,630, each of which is incorporated herein by reference.

Sequencing By Binding™ Technique: General Aspects

Described herein is a Sequencing By Binding™ technique that, in a single processing step (i.e., a so-called "blocking-and-examination" step), advances a primed template nucleic acid molecule forward by adding a single reversible terminator nucleotide to the 3'-end of a primer, and detects label attached to the cognate nucleotide downstream of that extended and blocked primer. This is accomplished by combining a catalytic metal ion, at least one polymerase, at least one incorporable reversible terminator nucleotide (e.g., unlabeled reversible terminator nucleotides) and at least one detectably labeled nucleotide (e.g., labeled non-incorporable nucleotides) to form ternary complexes that can be detected by virtue of the label attached to the nucleotide. The reversible terminator nucleotides are either incorporated into the primed template nucleic acid molecule in preference to the labeled nucleotides (e.g., when reversible terminator nucleotides are pre-loaded into ternary complexes in the absence of labeled nucleotides), or incorporated exclusively because the labeled nucleotides are structured to prevent incorporation (i.e., they are non-incorporable). Detection of label associated with different nucleic acid features, under dynamic equilibrium conditions, is used for identifying cognate nucleotides.

Also described herein is a Sequencing By Binding™ technique that employs discrete steps for: (1) incorporating a reversible terminator (e.g., an unlabeled reversible terminator) nucleotide to create a blocked primed template nucleic acid; and (2) detecting formation of a ternary complex that includes the blocked primed template nucleic acid, a polymerase, and a labeled nucleotide that is the next correct nucleotide to be incorporated. By this approach, different reaction mixtures are used for the incorporation and examination steps. Accordingly, the examination step that involves detection of ternary complexes stabilized on the blocked primed template nucleic acid can be carried out in the absence of unreacted reversible terminator nucleotides, and in the presence of distinguishably labeled nucleotides. As detailed below, an optional imaging wash step employing a stabilizing fluid can permit removal of extraneous labeled binding components (e.g., labeled nucleotides or labeled polymerases) while preserving integrity of ternary complexes for detection.

Using a single wash reagent to dissociate ternary complexes and remove reversible terminator moieties from blocked primed template nucleic acids is possible when the wash reagent conditions are incompatible with conditions needed for polymerase from the examination step to promote incorporation of labeled nucleotides that are not labeled non-incorporable nucleotides. This may be due to a wash buffer having a low pH (e.g., of about pH 5.0-6.0, or about pH 5.5), divalent catalytic metal ion chelators (e.g., EDTA), etc.

Sequencing By Binding™ procedures are typically carried out as a series of cycles, with each cycle including one or more steps that result in identification of the next correct nucleotide for a particular nucleotide position of a primed template nucleic acid. As such, the sequence of the nucleic acid template is determined from the series of nucleotides identified in the series of cycles. Convenient platforms for the sequencing chemistry can involve flow cells or individual wells of a multiwell plate, where the different nucleic acids may be present as features such as in vitro- or in situ-synthesized clusters of primed template nucleic acids, or such as immobilized microbeads displaying primed template nucleic acid molecules. Cognate nucleotide identification can be made by identifying label associated with the nucleotide analog used in the procedure. This can be carried out using as few as a single imaging step to detect each of four different types of cognate nucleotide (i.e., labeled non-incorporable nucleotide analogs of: dATP, dGTP, dCTP, and dTTP or dUTP).

Generally speaking, the polymerase used in nucleic acid Sequencing By Binding™ reactions undergoes transitions between open and closed conformations during discrete steps of the reaction. In one step, the polymerase binds to a primed template nucleic acid to form a binary complex, also referred to herein as the pre-insertion conformation. In a subsequent step, an incoming nucleotide is bound and the polymerase fingers close, forming a pre-chemistry conformation comprising the polymerase, primed template nucleic acid and nucleotide (i.e., a ternary complex); wherein the bound nucleotide has not been incorporated. The two steps can either use the same polymerase, or different polymerases.

A catalytic metal ion (e.g., $Mg^{2+}$ or $Mn^{2+}$) catalyzing chemical incorporation of the next correct nucleotide (e.g., a cognate incorporable reversible terminator nucleotide) can promote phosphodiester bond formation if the primer strand is free of any reversible terminator moiety. Here, nucleophilic displacement of a pyrophosphate (PPi) by the 3'-hydroxyl of the primer results in phosphodiester bond formation. This is generally referred to as nucleotide "incorporation." The polymerase returns to an open state upon the release of PPi following nucleotide incorporation, and translocation initiates the next round of reaction. Certain details of Sequencing By Binding™ procedures can be found in commonly owned U.S. patent applications identified by Ser. No. 14/805,381 (published as U.S. 2017/0022553 A1) and 62/375,379, the entire disclosures of these documents being incorporated by reference herein for all purposes.

While a ternary complex including a primed template nucleic acid molecule can form in the absence of a divalent catalytic metal ion (e.g., $Mg^{2+}$ or $Mn^{2+}$), chemical addition of nucleotide can proceed in the presence of the divalent metal ions if the primed template nucleic acid molecule is free of any reversible terminator moiety. Low or deficient levels of catalytic metal ions, such as $Mg^{2+}$ tend to lead to non-covalent (physical) sequestration of the next correct nucleotide in a tight ternary complex. Those having an ordinary level of skill in the art will appreciate that non-catalytic metal ions that inhibit incorporation also can be used for stabilizing ternary complexes. Certain procedures detailed below that employ a step for forming ternary complexes containing reversible terminator nucleotides in the absence of labeled nucleotides can use non-catalytic metal ions to stabilize ternary complexes preliminary to carrying out the blocking-and-examination step. Again, incorporation of the reversible terminator and detection of labeled nucleotide interaction with the blocked primer in a ternary complex can take place in the same reaction mixture during this combined blocking-and-examination step.

A blocked primer terminating at its 3'-end with a reversible terminator nucleotide that precludes phosphodiester bond formation also can be used for stabilizing ternary complex formation. The product of a blocking-and-examination step includes blocked primers that stabilize ternary complexes. In any reaction step described above, formation of a stabilized ternary complex containing a detectably labeled nucleotide that is not incorporated may be monitored to identify the next correct base in the nucleic acid sequence. Reaction conditions can be changed to disengage the polymerase and labeled cognate nucleotide from a blocked primed template nucleic acid molecule, and changed again to remove from the local environment any reversible terminator moiety attached to the nucleotide at the 3'-end of the primer strand of the primed template nucleic acid molecule. In some embodiments, both the polymerase and cognate nucleotide of the ternary complex, and the reversible terminator moiety are removed in a single step using a reagent that dissociates ternary complexes and cleaves the reversible terminator moiety from its position at the 3'-end of the blocked primed template nucleic acid molecule.

Figure 2:
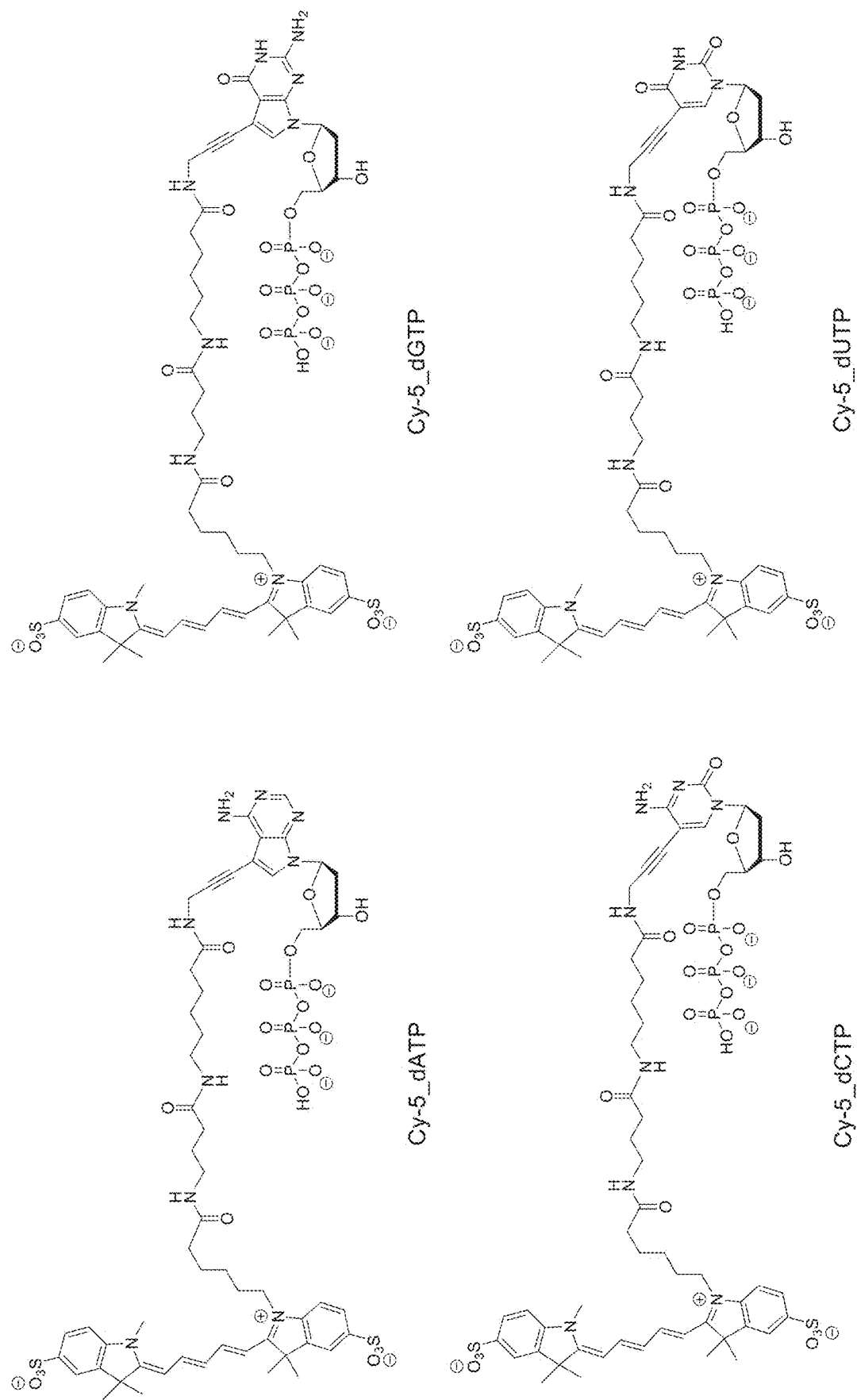
FIG. 2 shows the structural formula for each of four incorporable nucleotide analogs harboring a fluorescent label constructed on a Cy-5 scaffold. Pyrimidine analogs are labeled through position 5 of the nitrogenous base. Purine analogs are labeled through position 7 of the nitrogenous base.

Generally speaking, the disclosed Sequencing By Binding™ procedure includes an "examination" step or sub-step that detects signals useful for identifying the next template base. The detected signals reflect the dynamic equilibrium interaction of detectable label with primed template nucleic acid molecules of a nucleic acid feature. Optionally, the detected label is covalently linked to the cognate nucleotide. Optionally, the linkage joins the label to the base moiety of the nucleotide. Exemplary linkers are shown in FIG. 2 and in the Formulas below. Optionally, the label attached to the base is the only label attached to the nucleotide, meaning that neither the pentose sugar nor any phosphate moiety of the nucleotide is attached to a detectable label (e.g., an exogenous fluorescent label). Identity of the cognate nucleotide downstream of reversibly blocked primer is determined from signals detected without linking the cognate nucleotide to the 3'-end of the primer by a covalent bond.

Different aspects of the disclosed technique stabilize ternary complexes by different mechanisms. In some embodiments of the methods provided herein, particularly related to pre-loading ternary complexes with reversible terminator nucleotides in the absence of incorporable labeled nucleotides, the absence of a catalytic metal ion in the active site of the polymerase prevents the chemical incorporation of the nucleotide into the primer of the primed template nucleic acid. Optionally, the chelation of a catalytic metal ion in the reaction mixtures of the contacting step prevents the chemical incorporation of the nucleotide into the primer of the primed template nucleic acid. Optionally, a non-catalytic metal ion acts as a stabilizer for the ternary complex in the presence of the next correct nucleotide. In other embodiments, a chemical block on the 3' nucleotide of the primer of the primed template nucleic acid molecule (e.g., a reversible terminator moiety on the base or sugar of the nucleotide) prevents the chemical incorporation of the nucleotide into the primer of the primed template nucleic acid and stabilizes ternary complexes containing labeled nucleotides. Optionally, the catalytic metal ion used in these procedures is magnesium. The metal ion mechanisms of polymerases postulate that a low concentration of metal ions may be needed to stabilize the polymerase-nucleotide-DNA binding interaction. See, for instance, Section 27.2.2, Berg J M, Tymoczko J L, Stryer L, *Biochemistry* 5th Edition, WH Freeman Press, 2002.

The examination step or sub-step can involve providing a blocked primed template nucleic acid molecule, and contacting it with a polymerase (e.g., a DNA polymerase) and one or more detectably labeled test nucleotides being investigated as the possible next correct nucleotide, optionally in the presence of a catalytic metal ion. Further, there is a step that involves monitoring or measuring the interaction between the polymerase and the primed template nucleic acid in the presence of the test nucleotides. In some embodiments, the detectably labeled test nucleotide is labeled by attachment of the label or tag to a position on the base of the nucleotide (e.g., as shown in FIG. 2 or in accordance with Formulas below). The label or tag (e.g., a fluorescent dye) preferably is not an intercalating dye that that changes fluorescent properties upon binding to DNA. Optionally, the detecting or monitoring takes place in the presence of non-complexed labeled nucleotide (i.e., free in solution and not sequestered in a ternary complex).

Monitoring of this interaction can take place when the primer of the primed template nucleic acid molecule includes a blocking group that precludes enzymatic incorporation of an incoming nucleotide into the primer. Again, the examination step collects signal(s) that identify or determine the identity of the next correct nucleotide without requiring incorporation of that nucleotide.

Embodiments employing more than one polymerase offer another opportunity for differential control over incorporation of reversible terminator nucleotides, and examination of labeled nucleotides binding in ternary complexes to the blocked primed template nucleic acid. For example, different metal ions can be employed that are catalytic for the polymerase of one reaction mixture, but non-catalytic for a different polymerase used in the same reaction mixture, or in a different reaction mixture. In another example, certain polymerases (e.g., polβ) will not bind or accept reversible terminator nucleotides at low concentrations (i.e., the reversible terminator nucleotide has low affinity for the enzyme), but a different enzyme (e.g., Therminator™) will do so. Still further, two different polymerases can be included in the same reaction mixture at different concentrations to promote improved detection of labeled nucleotide participating in formation of ternary complexes.

Referring to concentrations of labeled nucleotides that can be used for performing the described techniques, in some embodiments it is preferred for the concentration of individual labeled nucleotides to be below 200 nM. When this is the case, ternary complexes including the labeled nucleotide can be more clearly imaged without requiring a wash step to remove non-complexed labeled nucleotides remaining free in solution. Preferred concentration ranges for individual labeled nucleotides are from 10 nM to 200 nM, more preferably from 10 nM to 150 nM, still more preferably in the range of from 25 nM to 150 nM, yet still more preferably from 50 nM to 150 nM. Alternatively, preferred concentration ranges for individual labeled nucleotides are from 10 nM to 100 nM, more preferably from 10 nM to 50 nM, or from 25 nM to 50 nM. Each of these ranges can be used for labeled nucleotides in the disclosed technique. Indeed, ternary complex formation using fluorescent, base-labeled nucleotide (e.g., Cy-5_dATP) has been easily detected using the procedure of Example 2, with labeled incorporable nucleotides at 10 nM, 25 nM, 50 nM and 100 nM concentrations. Optionally, each of four different distinguishably labeled nucleotides used in the same reaction mixture has a concentration falling in the range of from 50 nM to 150 nM. Although counterintuitive, perhaps because these concentration values fall below $K_m$ values for incorporation of labeled incorporable nucleotide analogs, or below $K_i$ values for ternary complex formation of labeled non-incorporable nucleotide analogs, excellent results have been achieved by this approach. Thus, concentrations of labeled nucleotides used in these procedures can be well below levels needed to saturate blocked primed template nucleic acid molecules with labeled nucleotide, while still providing outstanding results.

Whereas methods involving a single template nucleic acid molecule may be described for convenience, these methods are exemplary. The sequencing methods provided herein readily encompass a plurality of template nucleic acids, wherein the plurality of nucleic acids may be clonally amplified copies of a single nucleic acid, or disparate nucleic acids, including combinations, such as populations of disparate nucleic acids that are clonally amplified.

The Blocking-and-Examination Step

A combined "blocking-and-examination" step includes the following sub-steps: (1) providing an unblocked primed template nucleic acid (i.e., a template nucleic acid molecule hybridized with a primer having an extendable 3'-end); (2) contacting the primed template nucleic acid molecule with a liquid reagent that includes at least one polymerase, a plurality of incorporable reversible terminator nucleotides, a plurality of distinguishably labeled nucleotides, and a catalytic metal ion to permit incorporation of one reversible terminator nucleotide for each different primed template nucleic acid molecule; and (3) detecting the dynamic equilibrium binding of the labeled nucleotide with the extended and blocked primed template nucleic acid molecule (e.g., in a ternary complex that includes polymerase) that resulted from incorporation of the reversible terminator nucleotide.

Since only the reversible terminator nucleotides can be incorporated by particular embodiments of the methods described herein, primers are extended by only a single nucleotide in those embodiments. Non-incorporable, labeled nucleotides present in the reaction mixture can bind to appropriate members of the population or ensemble of primed template nucleic acid molecules (e.g., immobilized to a solid support in a spaced-apart configuration that is either random or spatially defined) in a cognate nucleotide-specific manner. Label associated with the non-incorporable nucleotides can be detected, whereby a cognate nucleotide is identified for each different feature of the immobilized population of nucleic acids. Non-bound materials can be flushed from the system, and the reversible terminator moiety cleaved from the primers to reveal substrates for the next round of reversible terminator incorporation and examination (again following a single reagent delivery step).

Optionally, the blocking-and-examination step can be followed by the step of determining or identifying the cognate nucleotide using results from the detecting step. It will be understood that a determination or identification step can occur on a timeframe separate from fluidic contacting and detecting steps of that cycle. For example, the determination or identification of a cognate nucleotide can occur after a delay that covers one or more subsequent cycles in a Sequencing By Binding™ procedure. In some cases, the determination or identification of the next correct nucleotide for each cycle can occur after multiple cycles of a Sequencing By Binding™ procedure have been completed. Thus, signal data from the examination step of each cycle can be stored in a way that it is indexed to the respective cycle to allow later analysis on a cycle-by-cycle basis. For example, the signal data can be stored electronically for processing at a time convenient for the workflow.

Template nucleic acid molecules may be sequenced under conditions that do not require attachment of template nucleic acid or polymerase to a solid support. However, in certain preferred embodiments, primed template nucleic acids to be sequenced are attached to a solid support, such as an interior surface of a flow cell or well of a multiwell plate. The compositions, methods and systems described herein provide numerous advantages over previous systems, such as controlled reaction conditions, unambiguous determination of sequence, longer read lengths, low overall cost of reagents, and low instrument cost.

Optionally, the provided method further includes a wash step. Optionally, the wash step is performed directly after detecting a dynamic equilibrium binding signal following a combined blocking-and-examination step. Alternatively, the wash step is performed after contacting the primed template nucleic acid molecules (e.g., a plurality of nucleic acid features) with the polymerase(s), plurality of reversible terminator nucleotides, plurality of detectably labeled nucleotides, and catalytic metal ion; but prior to the detecting step that collects data necessary for the step of identifying cognate nucleotide. In yet another alternative, the wash step occurs after binding polymerase and reversible terminator nucleotides to the primed template nucleic acid molecules in the absence of detectably labeled nucleotides under conditions that stabilize ternary complexes. Optionally, the stabilizing conditions include a stabilizing agent. Optionally, the stabilizing agent is a non-catalytic metal ion (e.g., a divalent non-catalytic metal ion) that inhibits nucleotide incorporation or polymerization. Non-catalytic metal ions include, but are not limited to, calcium, strontium, scandium, titanium, vanadium, chromium, iron, cobalt, nickel, copper, zinc, gallium, germanium, arsenic, selenium, rhodium, europium, and terbium ions. In particular embodiments, the non-catalytic metal ions are in a divalent state, for example, being supplied to a polymerase in the presence of appropriate counterions, or under other known conditions, for stabilizing the divalent state. In still yet another alternative, the wash step is carried out using a stabilizing fluid to remove non-complexed labeled binding components (e.g., nucleotides or polymerases) from contact with ternary complexes, and signal indicating the presence of ternary complexes is detected during the wash step. This signal can then be used for identifying cognate nucleotide. Optionally, the ternary complex has a half-life and the wash step is performed for a duration shorter than the half-life of the ternary complex formed when a nucleotide molecule provides a base that is complementary to the next base of the primed template nucleic acid molecule.

The examination step or sub-step can involve binding a polymerase to the polymerization initiation site of a primed template nucleic acid molecule in a reaction mixture comprising a catalytic metal ion, and one or more detectably labeled nucleotides, and then monitoring localization of the detectable label to the feature including the primed template nucleic acid molecule. Optionally, a nucleotide is sequestered within the polymerase-primed template nucleic acid complex to form a ternary complex, under conditions in which incorporation of the enclosed nucleotide by the polymerase is inhibited or precluded. Optionally, the ternary complex is stabilized by the presence of a blocking moiety (e.g., a reversible terminator moiety) on the 3' terminal nucleotide of the primer. Optionally a stabilizer is added to stabilize the ternary complex in the presence of the next correct nucleotide. This ternary complex is in a stabilized or polymerase-trapped pre-chemistry conformation. Optionally, the detectably labeled nucleotides are detectably labeled non-incorporable nucleotides (e.g., a label can be attached via a linker shown in FIG. 2 or in a Formula below).

The provided method may further include preparing the blocked primed template nucleic acid molecule for a next round of reversible terminator incorporation and labeled nucleotide (e.g., labeled non-incorporable nucleotide) binding. Optionally, the preparing includes subjecting the primed template nucleic acid or the ternary complex to one or more wash steps; a temperature change; a mechanical vibration; a pH change; a chemical treatment to remove reversible terminator moieties; or an optical stimulation. Optionally, the wash step comprises contacting the blocked primed template nucleic acid molecule or the ternary complex that includes the blocked primed template nucleic acid molecule with one of more buffers, detergents, protein denaturants, proteases, oxidizing agents, reducing agents, or other agents capable of releasing internal crosslinks within a polymerase or crosslinks between a polymerase and nucleic acid. Removal of a reversible terminator moiety from the blocked primed template nucleic acid molecule (e.g., "deblocking") can be effected using any approach known to one of ordinary skill in the art.

The blocking-and-examination step of the described procedure may be repeated 1, 2, 3, 4 or more times with steps for removal of ternary complexes and reversible terminator moieties from the primed template nucleic acid molecules. The examination and incorporation steps may be repeated for a predefined number of cycles, until the desired sequence of the template nucleic acid is obtained or until certain reaction criteria are reached such as a minimum signal intensity or signal to noise ratio.

In some embodiments, rather than being carried out in a single combined step, primer blocking (by incorporation of a reversible terminator nucleotide) and examination to detect formation of a ternary complex that includes a cognate nucleotide (e.g., a labeled cognate nucleotide analog) are carried out in separate steps. In these cases, the reversible terminator incorporation reaction can be carried out in the absence of labeled nucleotides that do not include any reversible terminator moiety.

The Contacting Step

Some embodiments of the disclosed technique involve contacting a reversibly blocked primed template nucleic acid molecule with particular types of detectably labeled nucleotides that include a label or tag attached to the nucleotide base. This can be done in the absence of unreacted or "free" (i.e., non-complexed) reversible terminator nucleotides. A label can be attached to a nucleotide via a linker shown in FIG. 2 or in a Formula below. Optionally, ternary complex formation using labeled nucleotides is assessed in the presence of a catalytic metal ion that was included in a reagent provided in the contacting step. According to one embodiment, ternary complex formation is detected or assessed during an imaging wash step. Preferably, signal indicating the presence of the ternary complex can be detected (i.e., remains detectable) in a stabilizing fluid over the course of at least 10 seconds, at least 30 seconds, five minutes, or even 10 minutes. Here the composition of the reaction mixture used to form ternary complexes in a contacting step is different from the composition of the reaction mixture in which ternary complexes are detected. According to another embodiment, the detectably labeled nucleotides have affinity for polymerase that permits use of relatively reduced concentrations of labeled nucleotides in the non-incorporating binding reactions. Advantageously, dynamic equilibrium binding of the high affinity nucleotides at low nucleotide concentration permits detection or monitoring of the nucleotide binding without removing non-bound nucleotides from the binding reaction mixture, for example by a wash step. Here, a reversible terminator nucleotide may have been added in a reaction mixture different from the reaction mixture used to measure, monitor or assess dynamic equilibrium binding of the labeled nucleotide(s).

Some embodiments of the disclosed technique employ a "pre-load" of incorporable reversible terminator nucleotides in the absence of labeled nucleotides. Optionally, the reaction mixture of the contacting step used in the pre-load step, wherein reversible terminator nucleotides are sequestered in ternary complexes without incorporation, includes a stabilizing agent. Optionally, the stabilizing agent is a non-catalytic metal ion (e.g., a divalent or trivalent non-catalytic metal ion). Non-catalytic metal ions useful in this context include, but are not limited to ions of: calcium, strontium, scandium, titanium, vanadium, chromium, iron, cobalt, nickel, copper, zinc, gallium, germanium, arsenic, selenium, rhodium, europium, and terbium. For example, the non-catalytic metal ions can be in a divalent state. Here, pre-loading of a non-catalytic ternary complex is achieved during exposure of nucleic acid features to a first solution, while incorporation and detection are performed during exposure to a second solution.

Some embodiments of the disclosed technique involve contacting a primed template nucleic acid having an extendable 3'-end with a reaction mixture that includes: one or more polymerases, one or more incorporable reversible terminator nucleotides (e.g., unlabeled reversible terminator nucleotides), one or more labeled non-incorporable nucleotides, and a catalytic metal ion. For example, four reversible terminator nucleotides, four labeled non-incorporable nucleotides, and a catalytic metal ion can be used in the reaction mixture of the contacting step. Here, contact with a single reaction mixture allows incorporation and detection without the requirement for a pre-loading step. To be clear, labeled non-incorporable nucleotides used in this case harbor a chemical linkage or moiety that precludes participation in a polymerase-dependent incorporation reaction involving formation of a phosphodiester bond.

Optionally, the contacting step is facilitated by the use of a flow cell or chamber, multiwell plate, etc. Flowing liquid reagents through the flow cell, which contains an interior solid support surface (e.g., a planar surface), conveniently permits reagent exchange or replacement. Immobilized to the interior surface of the flow cell is one or more primed template nucleic acids to be sequenced or interrogated using the procedures described herein. Typical flow cells will include microfluidic valving that permits delivery of liquid reagents (e.g., components of the "reaction mixtures" discussed herein) to an entry port. Liquid reagents can be removed from the flow cell by exiting through an exit port. Optionally, liquid reagents can be moved back and forth within the flow cell, for example to effect mixing.

The Detecting Step

Detecting (e.g., via monitoring or measuring) the reversible interaction of a blocked primed template nucleic acid molecule with a polymerase and detectably labeled cognate nucleotide (e.g., a non-incorporable nucleotide) in the presence of catalytic metal ion may be accomplished in different ways. For example, monitoring can include measuring association kinetics for the interaction. Monitoring the interaction can include measuring equilibrium binding signals or equilibrium binding constants. Thus, for example, the monitoring may include measuring equilibrium binding signals, or the equilibrium binding constant in the presence of one or more of the labeled nucleotides. Monitoring the interaction can include, for example, measuring dissociation kinetics of the nucleotide from the blocked primed template nucleic acid in the presence of any one of the four nucleotides. Optionally, monitoring the interaction of the polymerase with the primed template nucleic acid molecule in the presence of a nucleotide molecule includes measuring the kinetics of the dissociation of the closed-complex (i.e., dissociation of the primed template nucleic acid, the polymerase, and any one of the four nucleotide molecules). Association, equilibrium and dissociation kinetics are known and can be readily determined by one in the art. See, for example, Markiewicz et al., *Nucleic Acids Research* 40(16):7975-84 (2012); Xia et al., *J. Am. Chem. Soc.* 135 (1):193-202 (2013); Brown et al., *J. Nucleic Acids, Article ID* 871939, 11 pages (2010); Washington, et al., *Mol. Cell. Biol.* 24(2):936-43 (2004); Walsh and Beuning, *J. Nucleic Acids*, Article ID 530963, 17 pages (2012); and Roettger, et al., *Biochemistry* 47(37):9718-9727 (2008), which are incorporated by reference herein in their entireties. It will be understood that a detection technique can accumulate signal over a relatively brief duration as is typically understood to be a single timepoint acquisition. Alternatively, signal can be continuously monitored over time as is typical of a time-based acquisition. It is also possible to acquire a series of timepoints in a periodic fashion to obtain a time-based acquisition.

Preferably, the examination steps or sub-steps in accordance with the disclosed technique involve formation of a ternary complex that includes a polymerase, a blocked primed template nucleic acid, and a labeled nucleotide without incorporation of that nucleotide. Optionally, the ternary complex is formed and detected in the presence of a catalytic metal ion. Optionally, the ternary complex is formed and detected in the presence of a catalytic metal ion and in the absence of a non-catalytic metal ion that inhibits incorporation. Characteristics of the formation and/or release of the ternary complex can be detected to identify the enclosed nucleotide and therefore the next base in the template nucleic acid. Ternary complex characteristics can be dependent on the sequencing reaction components (e.g., polymerase, primer, template nucleic acid, nucleotide) and/or reaction mixture components and/or conditions. Detection of the label of the labeled nucleotide is used to identify the nucleotide present in the ternary complex.

Detection of ternary complexes can take place in different types of reaction mixtures. Optionally, the examination step or sub-step involves detecting the interaction of a polymerase with a blocked primed template nucleic acid in the presence of a labeled nucleotide and a catalytic metal ion. Optionally, the examination step or sub-step involves detecting a labeled nucleotide in a ternary complex after non-bound nucleotides (i.e., nucleotides remaining free in the solution phase) have been removed from contact with the ternary complex. The formation of a ternary complex may be detected or monitored by detecting or monitoring the label attached to the nucleotide. Optionally, the absence of formation of ternary complex is detected or monitored. Optionally, the dissociation of a ternary complex is monitored. Optionally, the incorporation step involves detecting or monitoring incorporation of a nucleotide, such as a reversible terminator nucleotide.

At least one nucleotide employed in the procedure can have a detectable label or tag (e.g., a fluorescent label or a Raman scattering tag). Optionally, the detectable label or tag on the nucleotide is removable. As discussed elsewhere herein, when using single-scan imaging to detect multiple labels for identifying all four cognate nucleotides, as few as two labeled nucleotides among the plurality of different nucleotides will harbor detectable labels. This can provide information about four different nucleotides based on monitoring ternary complex formation. Of course, a single nucleotide label can be used when multiple scans (e.g., four independent scans) are performed.

Once the detecting step necessary to establish identity of the next correct nucleotide has been completed, ternary complexes and any reversible terminator moiety attached to the primer strand of the primed template nucleic acid molecule can be dissociated or removed. The blocking-and-examination step, or alternatively a simple blocking step preliminary to an examination step, can then be repeated to extend the primer strand by a single nucleotide. Label associated with the next correct nucleotide can then be detected. This procedure can ensure that only one nucleotide is incorporated per sequencing cycle. Optionally, the reversible terminator nucleotides are not labeled with fluorescent or other detectable labels. Optionally, there is a step to preload the reversible terminator into ternary complexes in the absence of labeled nucleotide (e.g., labeled non-incorporable nucleotide) preliminary to conducting the second blocking-and-examination step.

Optionally, the step for detecting ternary complexes (e.g., containing detectably labeled nucleotides, or detectably labeled polymerases) takes place during a wash step carried out using a stabilizing fluid. Optionally, the stabilizing fluid is held static (i.e., not moving or flowing) during the detection step. Advantageously, detection of ternary complexes during an imaging wash step can reduce background signal associated with non-bound nucleotides or polymerases that may harbor detectable labels. Again, by this approach ternary complex detection can take place in a reaction mixture different from the reaction mixture that provided the labeled nucleotide(s) to the primed template nucleic acid molecule, which optionally can be blocked at its 3'-end with a reversible terminator moiety.

The Identifying Step

A step for identifying a cognate nucleotide using signal data acquired for ternary complex formation, without incorporation, naturally follows the step for detecting the interaction. For example, detecting a fluorescent signal indicating the presence of a distinguishable label in a ternary complex yields information that can be stored electronically (or in another non-transient format) and processed to make the cognate nucleotide identification at a later time (e.g., after multiple rounds of reversible terminator incorporation and labeled nucleotide interaction with a blocked primed template nucleic acid in the presence of a polymerase have been performed). Thus, it is unnecessary to make the cognate nucleotide identification from one round or cycle of reversible terminator incorporation and labeled nucleotide examination before the next cycle is performed.

In certain embodiments, a ternary complex that includes a blocked primed template nucleic acid molecule is formed in the presence of one or more polymerases and a plurality of detectably labeled nucleotides. Optionally, a catalytic metal ion is also included to permit incorporation of a reversible terminator nucleotide if the primed template nucleic acid is not already blocked from extension. Optionally, the detectably labeled nucleotide is a detectably labeled non-incorporable nucleotide (e.g., a label can be attached via a linker shown in FIG. 2 or in a Formula below). Optionally, cognate nucleotide participating in the ternary complex is identified by observing destabilization of the complex that occurs when the cognate nucleotide is absent from the reaction mixture. This is conveniently carried out, for example, by exchanging one reaction mixture for another. Here, loss of the complex is an indicator of cognate nucleotide identity. Loss of binding signal (e.g., a fluorescent binding signal associated with a particular locus on a solid support) can occur when the primed template nucleic acid is exposed to a reaction mixture that does not include the cognate nucleotide. Optionally, maintenance of a ternary complex in the presence of a single nucleotide in a reaction mixture also can indicate identity of the cognate nucleotide. When reversible terminator nucleotides are employed in combination with distinguishably labeled non-incorporable nucleotides, removal of excess nucleotides is optional, and not required because only a single reversible terminator nucleotide can be incorporated before the reversible terminator moiety is removed. Preferably, the label attached to the detectably labeled nucleotide does not substantially change its signal generating properties upon interaction with DNA (e.g., the label is not an intercalating dye), or upon inclusion in a ternary complex (e.g., the label is not a conformationally sensitive dye).

Reaction Mixtures

Nucleic acid sequencing reaction mixtures, or simply "reaction mixtures," can include one or more reagents that are commonly present in polymerase-based nucleic acid synthesis reactions. Reaction mixture reagents include, but are not limited to, enzymes (e.g., polymerase(s)), dNTPs (or analogs thereof), reversible terminator nucleotides, template nucleic acids, primer nucleic acids (e.g., including 3' blocked primers), salts, buffers, small molecules, agents that remove reversible terminator moieties from reversible terminator nucleotides, co-factors, metals, and ions. The ions may be catalytic ions, divalent catalytic ions, non-catalytic ions that inhibit polymerization, or a combination thereof. The reaction mixture can include salts, such as NaCl, KCl, potassium acetate, ammonium acetate, potassium glutamate, $NH_4Cl$, or $(NH_4HSO_4)$, that ionize in aqueous solution to yield monovalent cations. The reaction mixture can include a source of ions, such as $Mg^{2+}$ or $Mn^{2+}$, $Co^{2+}$, $Cd^{2+}$ or $Ba^{2+}$ ions. The reaction mixture can include tin, $Ca^{2+}$, $Zn^{2+}$, $Cu^{2+}$, $Co^{2+}$, $Fe^{2+}$ (e.g., $Fe(II)SO_4$), or $Ni^{2+}$, or other divalent or trivalent non-catalytic metal cations that stabilize ternary complexes by inhibiting formation of phosphodiester bonds between the primed template nucleic acid molecule and the cognate nucleotide. The buffer can include Tris, Tricine, HEPES, MOPS, ACES, IVIES, phosphate-based buffers, and/or acetate-based buffers. The reaction mixture can include chelating agents such as EDTA, EGTA, DTPA, NTA, and the like. Also provided herein are reaction mixtures that can be used during the blocking-and-examination step, as well as reaction mixtures used during removal of ternary complexes and reversible terminator moieties from blocked primers can include one or more of the aforementioned agents. For example, a wash buffer for removing polymerase bound to blocked primed template nucleic acid molecules can include EDTA. A reversible terminator moiety present on 3'-$ONH_2$ blocked primed template nucleic acid molecules can be removed using a cleavage or deblocking solution including sodium acetate buffer and $NaNO_2$. Optionally, a single reagent solution is used for both of these purposes.

Optionally, the reaction mixture of a blocking-and-examination step includes a high concentration of salt (e.g., >200 mM); a high pH (e.g., >pH 8.0); 1, 2, 3, 4, or more types of nucleotides; potassium glutamate; a chelating agent; a polymerase inhibitor; a catalytic metal ion; a non-catalytic metal ion; or any combination thereof. The first reaction mixture can include 10 mM to 1.6 M of potassium glutamate (including any amount between 10 mM and 1.6 M). Optionally, the incorporation reaction mixture includes a catalytic metal ion; 1, 2, 3, 4, or more types of nucleotides; potassium chloride; or any combination thereof. In addition to potassium salts, there also can be other salts that provide sources of monovalent cations. Likewise, other glutamate salts also may be useful.

Provided herein are methods for forming and/or stabilizing a ternary complex that includes a polymerase, a blocked primed template nucleic acid, and a labeled nucleotide (e.g., a labeled non-incorporable nucleotide). For the examination step or sub-step of the provided method, the ternary complex that includes detectably labeled nucleotide (e.g., the labeled non-incorporable nucleotide) is stabilized during the examination step by use of the blocked primed template nucleic acid molecule. Examples of useful labeled nucleotides include, but are not limited to those shown in FIG. 2 or conforming to a Formula set forth below.

Optionally, the examination reaction condition comprises a plurality of blocked primed template nucleic acids, polymerases, labeled nucleotides, or any combination thereof. Optionally, the plurality of labeled nucleotides comprises at least 1, 2, 3, 4, or more types of different non-incorporable nucleotides (e.g., labeled non-incorporable analogs of dATP, dGTP, dCTP, and dTTP or dUTP). Alternatively or additionally, the plurality of nucleotides comprises at most 1, 2, 3, 4, or more types of different non-incorporable nucleotides (e.g., labeled non-incorporable analogs of dATP, dGTP, dCTP, and dTTP or dUTP). Optionally, the plurality of nucleotides includes one or more types of nucleotides that, individually or collectively, complement at least 1, 2, 3 or 4 types of nucleotides in a template (e.g., having the binding specificity of dATP, dGTP, dCTP, and dTTP or dUTP). Optionally, the plurality of template nucleic acids is a clonal population of template nucleic acids.

Optionally, the examination reaction mixture includes one or more reagents or biomolecules generally present in a nucleic acid polymerization reaction. Reaction components used in addition to those set forth herein, may include, but are not limited to, salts, buffers, small molecules, detergents, crowding agents, metals, and ions. Optionally, properties of the reaction mixture may be manipulated, for example, electrically, magnetically, and/or with vibration.

Illustrative Reaction Mixtures

Certain reaction mixtures that can be used with the disclosed technique include each of: a primed template nucleic acid molecule having a 3'-end available for polymerization; one or more polymerases; one or more incorporable reversible terminator nucleotides; one or more distinguishably labeled nucleotide analogs; and a catalytic metal ion.

According to one generally preferred embodiment, the one or more incorporable reversible terminator nucleotides include four incorporable reversible terminator nucleotides.

According to another generally preferred embodiment, the one or more distinguishably labeled nucleotide analogs include four distinguishably labeled nucleotide analogs.

According to another generally preferred embodiment, the one or more incorporable reversible terminator nucleotides include four incorporable reversible terminator nucleotides, and the one or more distinguishably labeled nucleotide analogs include four distinguishably labeled nucleotide analogs.

According to another generally preferred embodiment, the one or more incorporable reversible terminator nucleotides are not distinguishably labeled.

According to another generally preferred embodiment, the one or more incorporable reversible terminator nucleotides are distinguishably labeled.

According to another generally preferred embodiment, each of the distinguishably labeled nucleotide analogs is a distinguishably labeled non-incorporable nucleotide analog that includes a chemical moiety or linkage that precludes phosphodiester bond formation.

According to another generally preferred embodiment, each of the distinguishably labeled nucleotide analogs is a distinguishably labeled incorporable nucleotide analog.

According to another generally preferred embodiment, the one or more incorporable reversible terminator nucleotides include four incorporable reversible terminator nucleotides, the one or more distinguishably labeled nucleotide analogs include four distinguishably labeled nucleotide analogs, and the four incorporable reversible terminator nucleotides are not distinguishably labeled.

According to another generally preferred embodiment, the one or more incorporable reversible terminator nucleotides include four incorporable reversible terminator nucleotides, the one or more distinguishably labeled nucleotide analogs include four distinguishably labeled nucleotide analogs, and the four incorporable reversible terminator nucleotides are distinguishably labeled.

According to another generally preferred embodiment, the one or more incorporable reversible terminator nucleotides include four incorporable reversible terminator nucleotides, the one or more distinguishably labeled nucleotide analogs include four distinguishably labeled nucleotide analogs, and each of the distinguishably labeled nucleotide analogs is a distinguishably labeled non-incorporable nucleotide analog.

According to another generally preferred embodiment, the one or more incorporable reversible terminator nucleotides include four incorporable reversible terminator nucleotides, the one or more distinguishably labeled nucleotide analogs include four distinguishably labeled nucleotide analogs, and each of the distinguishably labeled nucleotide analogs is a distinguishably labeled incorporable nucleotide analog.

According to another generally preferred embodiment, the one or more incorporable reversible terminator nucleotides include four incorporable reversible terminator nucleotides, the one or more distinguishably labeled nucleotide analogs include four distinguishably labeled nucleotide analogs, each of the distinguishably labeled nucleotide analogs is a distinguishably labeled non-incorporable nucleotide analog, and the four incorporable reversible terminator nucleotides are not distinguishably labeled.

According to another generally preferred embodiment, the one or more incorporable reversible terminator nucleotides include four incorporable reversible terminator nucleotides, the one or more distinguishably labeled nucleotide analogs include four distinguishably labeled nucleotide analogs, each of the distinguishably labeled nucleotide analogs is a distinguishably labeled incorporable nucleotide analog, and the four incorporable reversible terminator nucleotides are distinguishably labeled.

According to another generally preferred embodiment, the one or more incorporable reversible terminator nucleotides include four incorporable reversible terminator nucleotides, the one or more distinguishably labeled nucleotide analogs include four distinguishably labeled nucleotide analogs, each of the distinguishably labeled nucleotide analogs is a distinguishably labeled non-incorporable nucleotide analog, the four incorporable reversible terminator nucleotides are not distinguishably labeled, each of the distinguishably labeled non-incorporable nucleotide analogs includes a different fluorescent label, and each of the different fluorescent labels is covalently attached to one of the distinguishably labeled non-incorporable nucleotide analogs at a position on its base moiety.

More preferably, none of the different fluorescent labels is an intercalating dye that changes fluorescence after contacting DNA.

According to another generally preferred embodiment, each of the distinguishably labeled nucleotide analogs includes a distinguishable fluorescent label, and none of the distinguishable fluorescent labels is an intercalating dye that changes fluorescence after contacting DNA.

According to another generally preferred embodiment, the one or more incorporable reversible terminator nucleotides include four incorporable reversible terminator nucleotides, the one or more distinguishably labeled nucleotide analogs include four distinguishably labeled nucleotide analogs, and each of the four distinguishably labeled non-incorporable nucleotide analogs comprises a triphosphate group with a modified linkage between alpha and beta phosphorus atoms.

According to another generally preferred embodiment, the catalytic metal ion is either $Mg^{2+}$ ion, or $Mn^{2+}$ ion.

According to another generally preferred embodiment, each of the incorporable reversible terminator nucleotides includes a 3'-OH modification.

Useful Nucleotides and Nucleotide Analogs

Different aspects of the disclosed technique employ incorporable reversible terminator nucleotide analogs, detectably labeled non-incorporable nucleotide analogs, or detectably labeled incorporable nucleotide analogs. Optionally, a nucleotide analog includes a nitrogenous base, five-carbon sugar, and at least one phosphate group; wherein any moiety of the nucleotide may be modified, removed and/or replaced.

There is flexibility in the nature of the reversible terminator nucleotide used in the incorporation step. For example, the reversible terminator nucleotide can include a 3'-hydroxyl group, which can be, for example, a free 3'-hydroxyl group. Optionally, the reversible terminator nucleotide includes a 3'-$ONH_2$ moiety attached at the 3' position of the sugar moiety. Optionally, the reversible terminator of the at least one nucleotide molecule is replaced or removed after any examination step (e.g., a blocking-and-examination step) to detect any ternary complex formation. Further examples of useful reversible terminator moieties are described, for example, in Bentley et al., *Nature* 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

Nucleotide analogs include, but are not limited to, alpha-phosphate modified nucleotides, alpha-beta modified nucleotide analogs, beta-phosphate modified nucleotides, beta-gamma modified nucleotide analogs, gamma-phosphate modified nucleotides, caged nucleotides, etc.

Examples of nucleotide analogs are described in U.S. Pat. No. 8,071,755, which is incorporated by reference herein in its entirety.

Nucleotide analogs can include terminators that reversibly prevent nucleotide incorporation at the 3'-end of the primer. One type of reversible terminator is a 3'-O-blocked reversible terminator. Here the terminator moiety is linked to the oxygen atom of the 3'-OH end of the 5-carbon sugar of a nucleotide. For example, U.S. Pat. Nos. 7,544,794 and 8,034,923 (the disclosures of these patents are incorporated by reference) describe reversible terminator dNTPs having the 3'-OH group replaced by a 3'-$ONH_2$ group. This type of reversible terminator moiety conveniently can be removed (e.g., in a "deblocking" step) using an acetate-buffered solution containing $NaNO_2$. Another type of reversible terminator nucleotide is the 2'-modified reversible terminator described in EP 1 974 057. Yet another type of reversible terminator is a 3'-unblocked reversible terminator, wherein the terminator moiety is linked to the nitrogenous base of a nucleotide. For example, U.S. Pat. No. 8,808,989 (the disclosure of which is incorporated by reference) discloses particular examples of base-modified reversible terminator nucleotides that may be used in connection with the methods described herein. Other reversible terminators that similarly can be used in connection with the methods described herein include those described in U.S. Pat. Nos. 7,956,171, 8,071,755, and 9,399,798 (the disclosures of these U.S. patents are incorporated by reference). For reviews of nucleotide analogs having terminators see e.g., Mu, R., et al., "The History and Advances of Reversible Terminators Used in New Generations of Sequencing Technology," Genomics, Proteomics & Bioinformatics 11(1):34-40 (2013). Optionally, one or more native nucleotides employed during the examination step is replaced by a second type of nucleotide that is incorporated during the incorporation step. For example, nucleotides present in the reaction mixture used during an examination step may be replaced by nucleotide analogs that include reversible terminator moieties (e.g., positioned on the base or sugar of the nucleotide molecule).

Optionally, nucleotide analogs have terminator moieties that irreversibly prevent nucleotide incorporation at the 3'-end of the primer. Irreversible nucleotide analogs include 2',3'-dideoxynucleotides, ddNTPs (ddGTP, ddATP, ddTTP, ddCTP). Dideoxynucleotides lack the 3'-OH group of dNTPs that is essential for polymerase-mediated synthesis.

Optionally, non-incorporable nucleotides comprise a blocking moiety that inhibits or prevents the nucleotide from forming a covalent linkage to a second nucleotide (3'-OH of a primer) during the incorporation step of a nucleic acid polymerization reaction. In certain embodiments, the blocking moiety can be removed from the nucleotide, allowing for nucleotide incorporation.

Optionally, a nucleotide analog has a different binding affinity for a polymerase than a native nucleotide. Optionally, a nucleotide analog has a different interaction with a next base than a native nucleotide. Nucleotide analogs and/or non-incorporable nucleotides may base-pair with a complementary base of a template nucleic acid.

FIG. 2 presents structural diagrams for fluorescently labeled analogs of each of dATP, dCTP, dGTP, and dUTP, where the label was attached through nitrogenous base position 5 for pyrimidines or position 7 for purines. Each nucleotide included a fluorescent moiety constructed on a Cy-5 scaffold. Notably, each of these base-labeled analogs compared favorably with the corresponding native nucleotide in an incorporation assay using the Therminator™ DNA polymerase. In the case of the labeled dUTP analog, the comparison was against dTTP. The following tabulated results (averaged from three trials) compare Km values determined in the incorporation assay.

| Tested Nucleotide | Km (µM) |
|---|---|
| dATP | 0.05 |
| Cy-5_dATP analog | 0.23 |
| dGPT | 0.23 |
| Cy-5_dGTP analog | 0.34 |
| dCTP | 0.82 |
| Cy-5_dCTP analog | 0.95 |
| dTTP | 0.92 |
| Cy-5_dUTP analog | 0.16 |

In particular embodiments, a nucleotide analog can have a structure similar to those shown in FIG. 2, but with the Cy-5 moiety replaced with any of a variety of other label moieties. Accordingly, a particularly useful nucleotide analog can have a structure according to Formula (1a), (1b), (1c) or (1d):

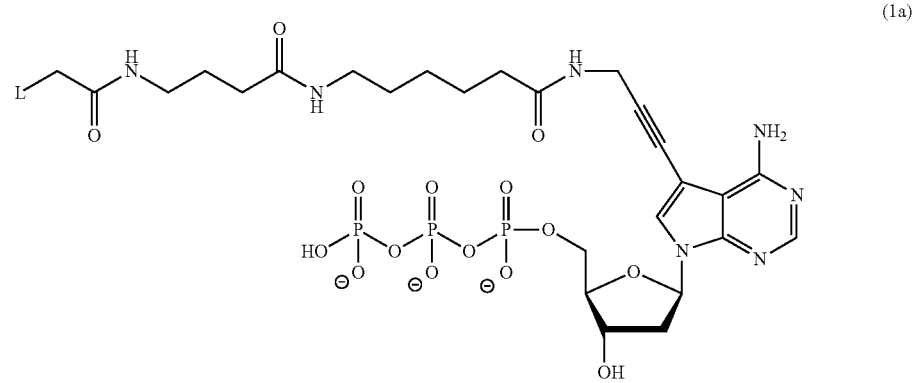

(1a)

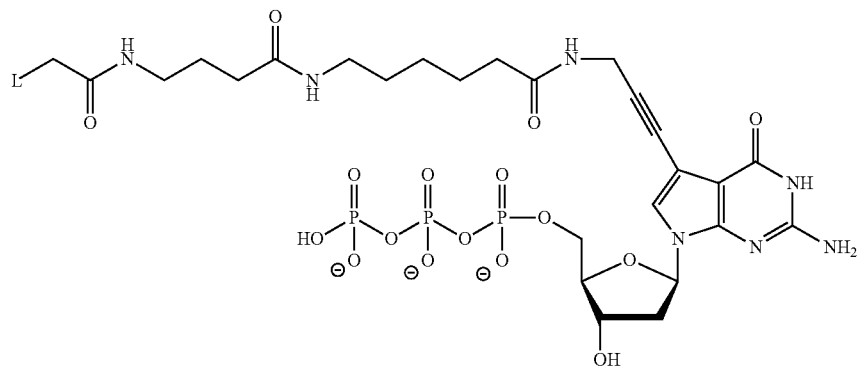

(1b)

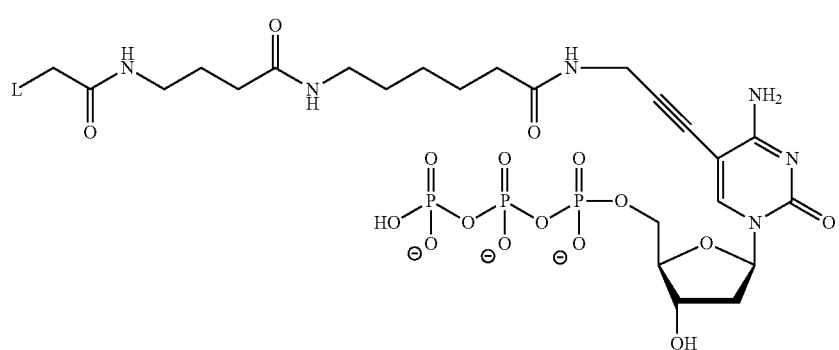

(1c)

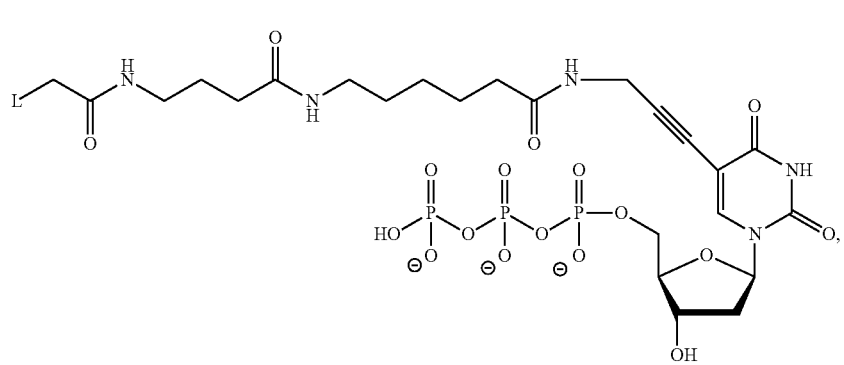

(1d)

wherein L is a label moiety. The label moiety can be, for example, a fluorescent label, a Raman scattering tag, a chemiluminescent tag, a plasmonic nanoparticle tag, another moiety set forth herein (e.g., in the context of labeling a nucleotide or polymerase) or another moiety known in the art for labeling molecules.

The linkers shown in FIG. 2 and in Formulas (1a), (1b), (1c) and (1d) have 18 atoms between the nitrogenous base and label moiety. A useful feature of these nucleotide analogs is the presence of a relatively planar and extended region at the end of the linker that attaches to the nitrogenous base. Specifically, a propargylamide moiety attaches the linker to the nitrogenous base in each of the nucleotide analogs. Moreover, the amide moieties in the linker form trigonal planar structures that are relatively extended. Linkers having extended structures can be advantageous when binding nucleotide analogs to a polymerase or other macromolecule. Although not wishing to be limited by theory, a planar and extended linkage is believed to efficiently position a label outside of the nucleotide binding pocket of a polymerase when the nucleotide participates in a ternary complex.

A further example of a linker having a propargylamide linkage to the nitrogenous base, amide moieties, and 18 atoms between the nitrogenous base and label is present in each of Formulas (2a), (2b), (2c) and (2d):

(2a)
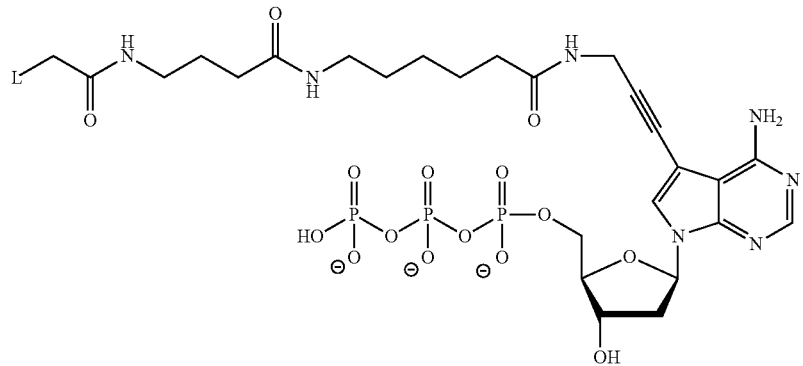
(2b)
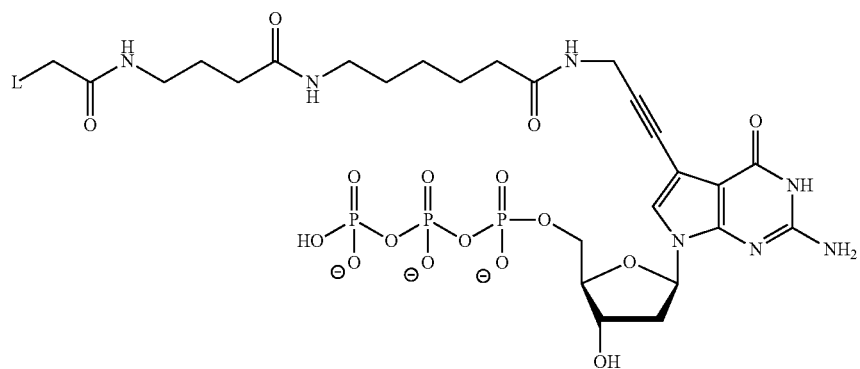
(2c)
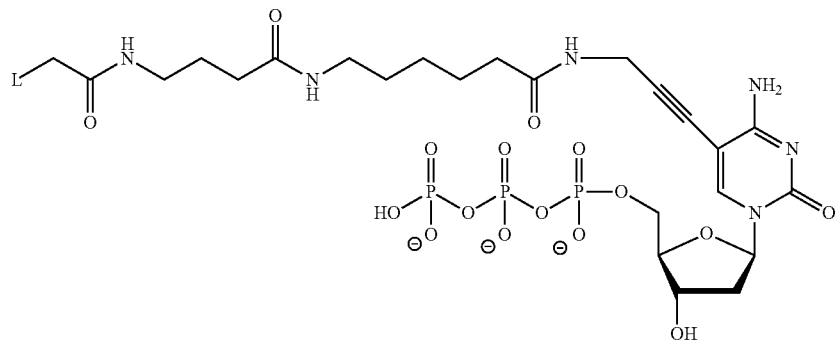
(2d)
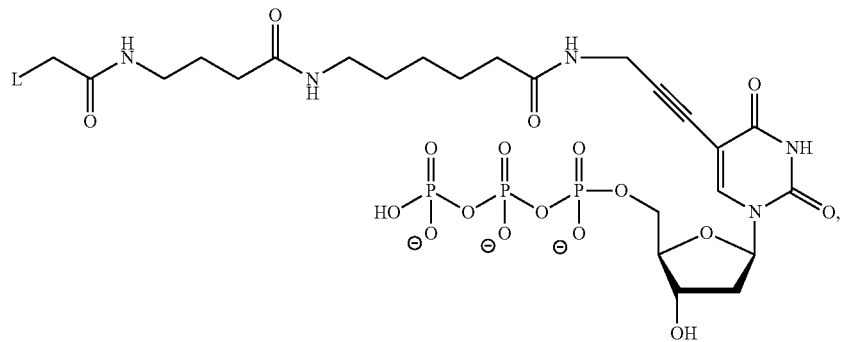

wherein L is a label moiety. Accordingly, the relative positions of amide moieties in a linker can be variable. Furthermore, the number of amide units and the number of carbons between amide units can vary, for example, as shown in Formulas (3a), (3b), (3c) and (3d):

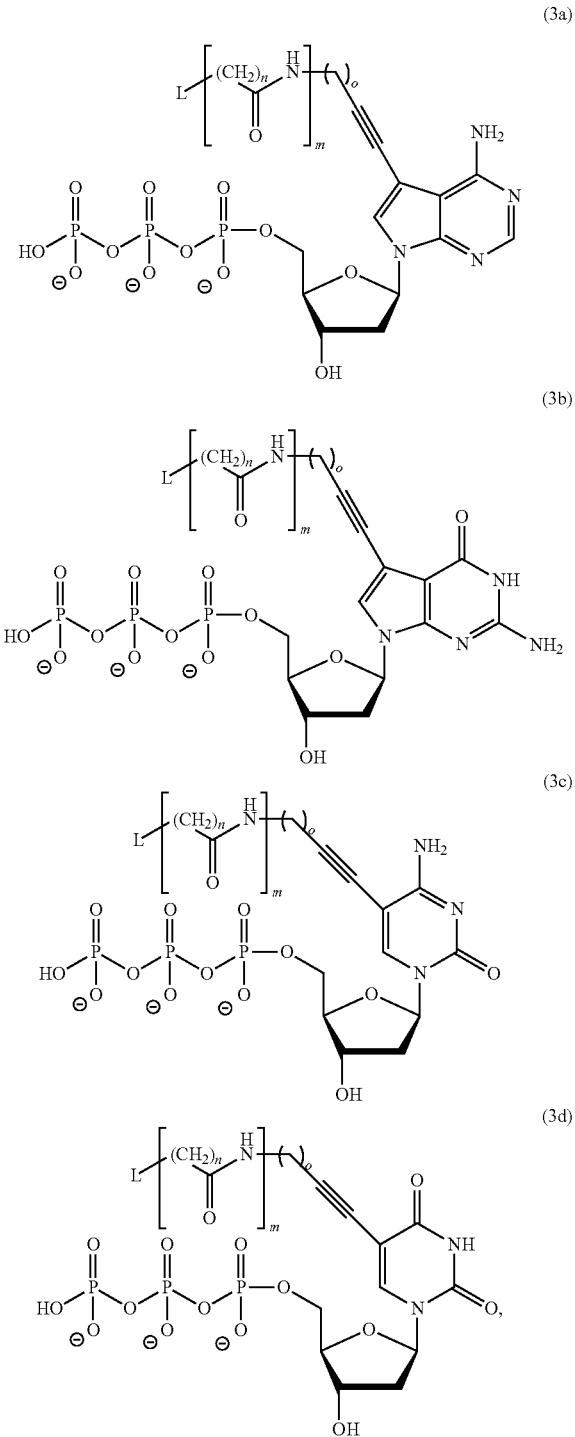

wherein L is a label moiety, n is any integer from 1 to 10, m is any integer from 1 to 5, and o is any integer from 1 to 10. As exemplified above, the integer n can differ between two or more $CH_2$—CO—NH units of Formula (3a), (3b), (3c) or (3d). In particular embodiments, n is at least 2, 3, 4, 5, 6, 8 or 10. Alternatively or additionally, m can be at least 2, 3, 4 or 5. As a further option, o can be at least 2, 3, 4, 5, 6, 8 or 10.

The linkers of FIG. 2 and the Formulas herein are exemplary. Other linkers can be used instead. For example, a linker can include a polyethylene glycol moiety and/or amino acid moiety. More specifically a linker can include a propargylamide linkage between a nitrogenous base and a polyethylene glycol moiety (e.g., $PEG_2$, $PEG_6$, $PEG_8$, or $PEG_{12}$) or a linker can include a propargylamide linkage between a nitrogenous base and a polyalanine or polyglycine moiety. Moreover, the propargylamide attachment between the nitrogenous bases and linkers of FIG. 2 and the Formulas herein is exemplary. A linker can attach to the nitrogenous base of a nucleotide in any of a variety of ways. Exemplary attachments include, but are not limited to, alkynyl, propargyl, propargylethoxyamido, vinyl, or allyl moiety attachments. The point at which the linker attaches to the nitrogenous base can be at an available carbon, for example, at position 2 of adenosine, position 8 of adenosine or guanine, deaza positions such as position 7 of 7-deazaguanine or 7-deazaadenine, position 5 of cytosine or uracil, or position 6 of thymine, uracil or cytosine. A linker can also be attached via exocyclic amines of adenosine, cytosine or guanine.

A linker that is present in a nucleotide analog of the present disclosure can have a length of at least 10, 11, 12, 13, 14, 15, 16, 18, 20, 22, 24, 26, 28, 30 or more atoms between the nitrogenous base and label moiety. Alternatively or additionally, the linker can have a length of at most 30, 28, 26, 24, 22, 20, 18, 16, 15, 12 or fewer atoms between the nitrogenous base and label moiety. It will be understood, that in some cases a label moiety may include atoms that act as an additional linker. For example, the Cy-5 label moieties in FIG. 2 include a chain of 5 carbons between the amide moiety of the linker and the quarternary amine of the fluorophore's conjugated system. The additional linker can include a chain having a length of at least 1, 2, 5 or 10 atoms. Alternatively or additionally, the additional linker can have a chain having a length of no more than 10, 8, 5, 4, 3, 2 or 1 atom.

As exemplified by the nucleotide analogs in FIG. 2 and in the above Formulas, a linker that is present in a nucleotide analog need not be cleavable. For example, the linker can be stable to conditions used in methods set forth herein such that the covalent structure of the linker is not changed during any particular step, or throughout all steps, of a method set forth herein. A linker that is present in a nucleotide analog can be at least as chemically stable as one or more other moieties in the analog. For example, the linker can be as chemically stable as the nitrogenous base, sugar and/or phosphate moiety during any particular step, or throughout all steps, of a method set forth herein.

It will be understood that the nucleotide analogs shown in FIG. 2 and in the above Formulas can include other modifications. For example, the nucleotide analogs can have fewer than three phosphates (e.g., a monophosphate or diphosphate), more than three phosphates, or modified phosphates such as those that render the nucleotide analog non-incorporable via polymerase catalysis at the 3' end of a primer. Furthermore, the sugar moiety can be a deoxyribose as shown, ribose (having oxygen atoms at both the 3' and 2' positions) or dideoxy-ribose (lacking oxygen atoms at both the 3' and 2' positions). Optionally, a blocking moiety can be present at the 2' or 3' position of the ribose. In some cases, the nucleotide can be incorporated into a nucleic acid (i.e., attached to a nucleic acid via the 5' position and/or 3' position of the nucleotide). As a further option, the ribose moiety can be replaced with other sugar analogs. Accordingly, a nucleotide can have a base moiety (B) attached to a linker as follows:

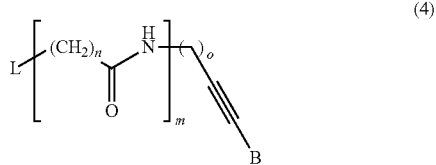

(4)

wherein L is a label moiety, n is any integer from 1 to 10, m is any integer from 1 to 5, and o is any integer from 1 to 10. The base B can be a pyrimidine or purine. In particular embodiments, B is attached to the linker via an available carbon, for example, at position 2 of adenosine, position 8 of adenosine or guanine, deaza positions such as position 7 of 7-deazaguanine or 7-deazaadenine, position 5 of cytosine or uracil, or position 6 of thymine, uracil or cytosine. A linker can also be attached to B via exocyclic amines of adenosine, cytosine or guanine.

The present disclosure provides a ternary complex, the ternary complex including a primed nucleic acid, polymerase, and nucleotide having a structure conforming to Formula (3a), (3b), (3c) or (3d). Optionally, the ternary complex can be stabilized using conditions or reagents set forth herein. For example, the primer can be a blocked primer. As such, the nucleotide that has the structure conforming to Formula (3a), (3b), (3c) or (3d) can be the next correct nucleotide. Any of a variety of polymerases, for example, one set forth herein, can be present in the ternary complex. Optionally, the nucleotide can have a structure conforming to Formula (1a), (1b), (1c), (1d), (2a), (2b), (2c) or (2d). Optionally, the nucleotide can have a structure shown in FIG. 2.

As indicated elsewhere herein, non-incorporable counterparts of base-labeled nucleotide analogs may include modifications to the phosphate moiety.

Useful Polymerases

Polymerases useful for carrying out the disclosed techniques include naturally occurring polymerases and modified variations thereof, including, but not limited to, mutants, recombinants, fusions, genetic modifications, chemical modifications, synthetics, and analogs. Naturally occurring polymerases and modified variations thereof are not limited to polymerases that retain the ability to catalyze a polymerization reaction. Optionally, the naturally occurring and/or modified variations thereof retain the ability to catalyze a polymerization reaction. Optionally, the naturally-occurring and/or modified variations have special properties that enhance their ability to sequence DNA, including enhanced binding affinity to nucleic acids, reduced binding affinity to nucleic acids, enhanced binding affinity to nucleotides, reduced binding affinity to nucleotides, enhanced specificity for next correct nucleotides, reduced specificity for next correct nucleotides, enhanced catalysis rates, reduced catalysis rates, catalytic inactivity etc. Mutant polymerases include polymerases wherein one or more amino acids are replaced with other amino acids, and insertions or deletions of one or more amino acids.

The term polymerase and its variants, as used herein, also refers to fusion proteins comprising at least two portions linked to each other, for example, where one portion comprises a peptide that can catalyze the polymerization of nucleotides into a nucleic acid strand is linked to another portion that comprises a second moiety, such as, a reporter enzyme or a processivity-modifying domain. For example, T7 DNA polymerase comprises a nucleic acid polymerizing domain and a thioredoxin binding domain, wherein thioredoxin binding enhances the processivity of the polymerase. Absent the thioredoxin binding, T7 DNA polymerase is a distributive polymerase with processivity of only one to a few bases. Although DNA polymerases differ in detail, they have a similar overall shape of a hand with specific regions referred to as the fingers, the palm, and the thumb; and a similar overall structural transition, comprising the movement of the thumb and/or finger domains, during the synthesis of nucleic acids.

DNA polymerases include, but are not limited to, bacterial DNA polymerases, eukaryotic DNA polymerases, archaeal DNA polymerases, viral DNA polymerases and phage DNA polymerases. Bacterial DNA polymerases include *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include DNA polymerases $\alpha$, $\beta$, $\gamma$, $\delta$, $\epsilon$, $\eta$, $\zeta$, $\lambda$, $\sigma$, $\mu$, and k, as well as the Revl polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cpl DNA polymerase, Cp7 DNA polymerase, T7 DNA polymerase, and T4 polymerase. Other DNA polymerases include thermostable and/or thermophilic DNA polymerases such as DNA polymerases isolated from *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavusu* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. go N-7 DNA polymerase; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; and the heterodimeric DNA polymerase DP1/DP2. Engineered and modified polymerases also are useful in connection with the disclosed techniques. For example, modified versions of the extremely thermophilic marine archaea *Thermococcus* species 9° N (e.g., Therminator DNA polymerase from New England BioLabs Inc.; Ipswich, MA) can be used. Still other useful DNA polymerases, including the 3PDX polymerase are disclosed in U.S. Pat. No. 8,703, 461, the disclosure of which is incorporated by reference in its entirety.

RNA polymerases include, but are not limited to, viral RNA polymerases such as T7 RNA polymerase, T3 polymerase, SP6 polymerase, and Kll polymerase; Eukaryotic RNA polymerases such as RNA polymerase I, RNA polymerase II, RNA polymerase III, RNA polymerase IV, and RNA polymerase V; and Archaea RNA polymerase.

Reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, and Telomerase reverse transcriptase that maintains the telomeres of eukaryotic chromosomes.

Modified polymerases include polymerases that contain an external tag (e.g., an exogenous detectable label), which can be used to monitor the presence and interactions of the polymerase. Optionally, the polymerase employed during the examination step includes at least one exogenous detectable label (e.g., a fluorescent label, a Raman scattering tag, a chemiluminescent tag, a plasmonic nanoparticle tag, etc.) chemically linked to the structure of the polymerase by a covalent bond. Optionally, the label(s) can be attached after the polymerase has been at least partially purified using protein isolation techniques. For example, the exogenous detectable label can be chemically linked to the polymerase using a free sulfhydryl or a free amine moiety of the polymerase. This can involve chemical linkage to the polymerase through the side chain of a cysteine residue, through the free amino group of the N-terminus (or cleaved N-terminus for native chemical ligation). An exogenous label can also be attached to a polymerase via protein fusion. Exemplary fluorescent labels that can be attached via protein fusion include, for example, Green Fluorescent Protein (and wavelength shifted variants thereof) and phycobiliproteins (e.g., phycocyanin, phycoerythrin and variants thereof). In certain preferred embodiments, a fluorescent label attached to the polymerase is useful for locating the polymerase, as may be important for determining whether or not the polymerase has localized to a feature or spot on an array corresponding to immobilized primed template nucleic acid. The fluorescent signal need not, and preferably does not change absorption or emission characteristics as the result of binding any nucleotide. Stated differently, the signal emitted by the labeled polymerase can be maintained substantially uniformly in the presence and absence of any nucleotide being investigated as a possible next correct nucleotide. In certain other preferred embodiments, the fluorescent signal emitted by the labeled polymerase is differentially affected by inclusion of the polymerase in binary and ternary complexes. Labels useful in this regard are known to those having an ordinary level of skill in the art.

Optionally, a conformationally sensitive dye may be attached close to the active site of the polymerase without affecting the polymerization ability or fidelity of the polymerase; wherein a change in conformation, or a change in polar environment due to the formation of a ternary complex is reflected as a change in fluorescence or absorbance properties of the dye. Common fluorophores such as Cy3 and fluorescein are known to have strong solvatochromatic response to polymerase binding and ternary complex formation, to the extent that the formation of ternary complex can be distinguished clearly from the binary polymerase-nucleic acid complex. Optionally, the ternary complex can be distinguished from binary complexes based on differences in fluorescence or absorbance signals from a conformationally sensitive dye. Optionally, a solvatochromatic dye may be employed to monitor conformational transitions; wherein the change in local polar environment induced by the conformational change can be used as the reporter signal. Solvatochromatic dyes include, but are not limited to, Reichart's dye, IR44, merocyanine dyes (e.g., merocyanine 540), 4-[2-N-substituted-1,4-hydropyridin-4-ylidine)ethylidene] cyclohexa-2,5-dien-1-one, red pyrazolone dyes, azomethine dyes, indoaniline dyes, diazamerocyanine dyes, indigoid dyes, as exemplified by indigo, and others as well as mixtures thereof. Methods to introduce dyes or fluorophores to specific sites of a polymerase are well known in the art. As a non-limiting example, a procedure for site specific labeling of a T7 DNA polymerase with a dye is provided in *Analytical Biochemistry* 384:136-44 (2009), which is incorporated by reference in its entirety.

Optionally, the polymerase used in the procedures described herein is engineered to possess certain functional properties. For example, the polymerase can be engineered to have lost the ability to catalyze phosphodiester bonds while retaining the ability to form a ternary complex with a primed template nucleic acid molecule and a cognate nucleotide (e.g., a non-incorporable nucleotide that includes a detectable label). Alternatively, the polymerase can be engineered to exhibit reduced propensity to form binary complexes that include non-cognate nucleotides, while retaining the ability to form a ternary complex with a primed template nucleic acid molecule and a cognate nucleotide (e.g., a non-incorporable nucleotide that includes a detectable label). According to yet another alternative, the polymerase has been engineered to include neighboring cysteine residues that interact when a ternary complex is formed.

Optionally, cysteine residues are positioned so that when a ternary complex is formed, the cysteines are near enough to form at least one disulfide bond to trap the polymerase in the closed conformation. Optionally, the finger and the thumb domain of the polymerase are engineered to contain one or more cysteines each, such that in the closed-complex, the cysteines on the opposing fingers interact, forming a disulfide bond and trapping the polymerase in its closed conformation. Introducing cysteines to suitable positions on the polymerase so as to induce disulfide bond formation can be accomplished using methods known to those in the art of protein engineering. A reducing agent such as 2-mercaptoethanol (BME), cysteine-HCl, dithiothreitol (DTT), Tris (2-carboxyethyl) phosphine (TCEP), or any combination thereof may be used to reduce the disulfide bond and release the polymerase.

Optionally, a cysteine-modified polymerase binds to a template nucleic acid without incorporating a correct nucleotide while forming a ternary complex. While in the ternary complex, the cysteines of the polymerase are close enough in space to form at least one disulfide bond, thereby stabilizing the ternary complex. In this example, the polymerase is trapped and prevented from nucleotide incorporation.

Labeled, Non-Incorporable Nucleotides

In some embodiments, cognate nucleotides are identified using different reaction mixtures to incorporate a reversible terminator nucleotide, and to assess dynamic equilibrium binding of a distinguishably labeled nucleotide analog. Here, for example, formation of ternary complexes including a labeled cognate nucleotide can be measured or assessed in the substantial absence of free (non-incorporated) reversible terminator nucleotides. Incorporation of a reversible terminator nucleotide to create a blocked primed template nucleic acid incapable of participating in a polymerization reaction is a standard procedure that will be familiar to those having an ordinary level of skill in the art. In a separate step, the blocked primed template nucleic acid can be contacted with a polymerase and at least one distinguishably labeled nucleotide (e.g., a labeled non-incorporable nucleotide), optionally in the presence of a catalytic metal ion (e.g., $Mg^{2+}$ or $Mn^{2+}$). If a cognate nucleotide is included in the reaction mixture, there is formed a stabilized ternary complex that includes the blocked primed template nucleic acid, the polymerase, and the cognate nucleotide. Following detection of the nucleotide in the complex, it may be desirable to remove the ternary complex and reversible terminator moiety from the blocked primed template nucleic acid, so the next round of reversible terminator incorporation and labeled nucleotide examination can take place. This can be accomplished in a single step using a deblocking wash buffer if the labeled nucleotides are labeled non-incorporable nucleotides (i.e., that do not become incorporable following removal of reversible terminator moieties from the blocked primed template nucleic acid). The presence of a catalytic metal ion, a polymerase, and non-incorporated reversible terminator nucleotides in the presence of the deblocking agent also would permit undesirable incorporation of deblocked reversible terminator nucleotides. This ability to carry out a single deblocking and wash step illustrates an advantage of using separate steps for incorporating reversible terminator nucleotides, and for examining ternary complex formation using labeled non-incorporable nucleotides.

The disclosed approach permits cognate nucleotide identification using a single reaction mixture that includes the combination of a polymerase, a plurality of incorporable reversible terminator nucleotides (i.e., nucleotides that are incorporated), and a plurality of detectably labeled nucleotides that are not incorporated (e.g., nucleotides that are non-incorporable). While a single type of polymerase may be used for the reaction mixture, combinations of two different polymerases alternatively can be used in the reaction mixture composition. By this approach, one type of polymerase may participate in the incorporation of the reversible terminator into the primer strand of the primed template nucleic acid molecule, and a different type of polymerase may participate in the examination procedure whereby cognate nucleotide is identified without incorporation. The primer strand of a primed template nucleic acid molecule undergoing examination without incorporation is chemically unchanged by the polymerase or any other enzyme during the procedure that identifies the cognate nucleotide based on detection of a labeled nucleotide. This is to say that the primer is neither extended by formation of a new phosphodiester bond, nor shortened by nucleolytic degradation during the examination step to identify the next correct nucleotide. In certain preferred embodiments, reaction mixtures include four incorporable reversible terminator nucleotides and four distinguishably labeled nucleotides that are non-incorporable.

Optionally, labeled nucleotides (e.g., non-incorporable nucleotides) that may be used for carrying out the disclosed technique can harbor detectable labels on any of the nucleotide base, sugar, or phosphate group(s). Exemplary fluorescent moieties that may be used include: rhodols; resorufins; coumarins; xanthenes; acridines; fluoresceins; rhodamines; erythrins; cyanins; phthalaldehydes; naphthylamines; fluorescamines; benzoxadiazoles; stilbenes; pyrenes; indoles; borapolyazaindacenes; quinazolinones; eosin; erythrosin; Malachite green; CY dyes (GE Biosciences), including Cy3 (and its derivatives) and Cy5 (and its derivatives); DYOMICS and DYLIGHT dyes (Dyomics) including DY-547, DY-630, DY-631, DY-632, DY-633, DY-634, DY-635, DY-647, DY-649, DY-652, DY-678, DY-680, DY-682, DY-701, DY-734, DY-752, DY-777 and DY-782; Lucifer Yellow; CASCADE BLUE; TEXAS RED; BODIPY (borondipyrromethene) (Molecular Probes) dyes including BODIPY 630/650 and BODIPY 650/670; ATTO dyes (Atto-Tec) including ATTO 390, ATTO 425, ATTO 465, ATTO 610 611X, ATTO 610 (N-succinimidyl ester), ATTO 635 (NHS ester); ALEXA FLUORS including ALEXA FLUOR 633, ALEXA FLUOR 647, ALEXA FLUOR 660, ALEXA FLUOR 700, ALEXA FLUOR 750, and ALEXA FLUOR 680 (Molecular Probes); DDAO (7-hydroxy-9H-(1,3-dichloro-9,9-dimethylacridin-2-one or any derivatives thereof) (Molecular Probes); QUASAR dyes (Biosearch); IRDYES dyes (LiCor) including IRDYE 700DX (NETS ester), IRDYE 80016 (NETS ester) and IRDYE 800CW (NETS ester); EVOBLUE dyes (Evotech Biosystems); JODA 4 dyes (Applied Biosystems); HILYTE dyes (AnaSpec); MR121 and MR200 dyes (Roche); Hoechst dyes 33258 and 33242 (Invitrogen); FAIR OAKS RED (Molecular Devices); SUNNYVALE RED (Molecular Devices); LIGHT CYCLER RED (Roche); EPOCH (Glen Research) dyes including EPOCH REDMOND RED (phosphoramidate), EPOCH YAKIMA YELLOW (phosphoramidate), EPOCH GIG HARBOR GREEN (phosphoramidate); Tokyo green (M. Kamiya, et al., 2005 Angew. Chem. Int. Ed. 44:5439-5441); and CF dyes including CF 647 and CF555 (Biotium). Optionally, the detectable label is attached to the non-incorporable nucleotide via a linker shown in FIG. 2 or in accordance with a Formula set forth herein.

It is to be understood that a composition comprising four distinguishably labeled nucleotides (e.g., non-incorporable nucleotides) does not necessarily require use of four different labels. For example, two labels ("A" and "B") can be used in combination with three different nucleotides to yield three different detectably labeled combinations ("A" and "B" and "AB"). An unlabeled nucleotide can be used in combination with these three distinguishable nucleotides to yield a fourth combination (i.e., a "dark" combination). In some embodiments, use of an unlabeled nucleotide and the fourth "dark" combination can be avoided altogether, deducing by the absence of a signal indicating the cognate nucleotide is any of the first three nucleotides that the cognate must be, by default, the fourth nucleotide. By this approach, all four different cognate nucleotides can be identified using fewer than four different labels. Optionally, one, two or three non-incorporable nucleotides among the plurality of non-incorporable nucleotides in the reaction mixture can harbor distinguishable labels. Optionally, four different non-incorporable nucleotides that are used in combination with each other are labeled with four different detectable moieties (e.g., fluorescent moieties or Raman labels).

To further clarify this point, reaction mixtures that can be used with the disclosed technique can include a plurality of distinguishable nucleotides. For example, when four distinguishable nucleotides (e.g., non-incorporable nucleotides) are being tested to identify a next correct nucleotide, there can be four non-incorporable nucleotides, each harboring a different detectable label. Alternatively, there can be three labeled nucleotides, each harboring a different detectable label, where the three nucleotides are combined with a single unlabeled nucleotide. Here, the three distinguishably labeled nucleotides can be used for identifying three different cognate nucleotides, with a fourth cognate nucleotide being identified as the one that did not participate in formation of a ternary complex that included one of the other labeled polymerases. As discussed immediately above, it is even possible to use only two different labels to prepare the three labeled nucleotides (e.g., non-incorporable nucleotides), which can be combined with a fourth unlabeled nucleotide (e.g., a non-incorporable nucleotide).

In certain embodiments, the nucleotide (e.g., a non-incorporable nucleotide) is labeled with a fluorescent detectable label, where the detectable label shows substantially no change in its fluorescent properties (excitation and emission) as the result of interaction with any polymerase, or with any double stranded nucleic acid. Preferably, the detectable label of a distinguishably labeled nucleotide is a fluorescent label, but the fluorescent label is not an intercalating dye that changes properties upon binding a primed template nucleic acid molecule. Preferably, the fluorescent label is not a dye that binds either the minor groove or major groove of double stranded DNA. Preferably, the fluorescent label is not a conformationally sensitive dye. Preferably, the fluorescent label is not an energy transfer partner in energy transfer relationship with a chemical moiety attached to the polymerase or to the blocked primed template nucleic acid.

Non-incorporable nucleotides harboring detectable label moieties can be synthesized using any number of different chemical scaffolds that will be familiar to those having an ordinary level of skill in the art. For example, U.S. Pat. No. 8,399,196, the disclosure of which is incorporated by reference herein, teaches non-incorporable nucleotide, nucleoside, and base analogs, including: H2-HPUra, H2-HPIso or by 4-Hydroxy-17-methylincisterol, aphidicolin, 2',2'-difluorodeoxycytidine (gemcitabine), triphosphates of acyclovir (ACV), 1-(2'-deoxy-2'-fluoro-beta-D-arabinofuranosyl)-5-iodocytosine (FIAC) and E-5-(2-bromovinyl)-2'-deoxyuridine (BVdU), 2'-Fluoro-2'-deoxycytidine triphosphate, 3'-ethynylcytidine (ECyd), 1-beta-D-arabinofuranosylthymine 5'-triphosphate and 1-beta-D-arabinofuranosylcytosine 5'-triphosphate, 3'-amino-3'-deoxythymidine, 5'-triphosphates of (E)-5-(2-bromovinyl)-2'-deoxyuridine and (E)-5-(2-bromovinyl)-1-beta-D-arabinofuranosyluracil, 3'-azido-2',3'-dideoxy-E-5-styrylUTP (6) and 2',3'-dideoxy-E-5-styrylUTP, 1-(2-Deoxy-2-fluoro-beta-L-arabinofuranosyl) pyrimidine, E-5-(2-bromovinyl)-1-beta-D-arabinofuranosyluracil, thymidine 5'-[alpha,beta-imido] triphosphate, 4'-azidothymidine triphosphate, 5-(2-chloroethyl)-2'-deoxyuridine, R- and S-enantiomers of 9-(3, 4-dihydroxybutyl)guanine [(R)- and (S)-DHBG], 9-(4-hydroxybutyl)guanine (HBG), and 9-(2-hydroxyethoxymethyl)guanine (ACV), 3-(substituted-butyl)-6-(3-ethyl-4-methylanilino)uracils, N2-(p-n-butylphenyl)dGTP (BuPdGTP) and 2-(p-n-butyl-anilino) dATP (BuAdATP), triphosphate derivatives of oxetanocin (1, carbocyclic analogue of 2'-deoxyguanosine, ganciclovir, pyridoxal, pyridoxal-5 mono-, di- and triphosphate, (S)-9-(3-hydroxy-2-phosphonylmethoxypropyl)adenine, 3'-O-methyl-ATP or nucleotide triphosphates which are made non-incorporable by alpha to beta phosphate methylene derivatization. Optionally, distinguishably labeled non-incorporable nucleotides include a chemical modification that can be any of: a modified 5'-triphosphate with a methylene ($CH_2$) group between the alpha and beta phosphorus atoms, a modified 5'-triphosphate with a difluoromethylene ($CF_2$) group between the alpha and beta phosphorus atoms, a modified 5'-triphosphate with a fluoromethylene (CHF) group between the alpha and beta phosphorus atoms, a modified 5'-triphosphate with an imido (NH) group between the alpha and beta phosphorus atoms, or a modified 5'-triphosphate with an azidomethylene ($CHN_3$) group between the alpha and beta phosphorus atoms.

Use of a Stabilizing Fluid Flush after Ternary Complex Formation

High concentrations of detectably labeled components can sometimes be used to drive formation of transient or reversible ternary complexes that are to be detected. Unfortunately, non-complexed reagents harboring detectable labels and remaining in the presence of the specific complexes can generate signals that confound or mask the desired detection. This is especially problematic when the signal generated by the detectable label is substantially similar irrespective of whether the labeled component (e.g., polymerase or nucleotide) is free in solution or included in a complex (e.g., a ternary complex).

The fact that nucleotide concentrations typically far exceed polymerase concentrations in binding reaction mixtures of Sequencing By Binding™ assays means that procedures employing labeled nucleotide can be particularly susceptible to high backgrounds that obscure ternary complex detection. Moreover, the dynamic nature of the ternary complex (e.g., where ternary complexes are in a state of flux, forming and dissociating, and exchanging with components in their chemical environments) often complicates the situation when conventional aqueous wash steps are performed to remove non-complexed reagents from the system. This is because the reversible complex that is to be detected can be unstable, and so dissociates over time (e.g., over the course of the monitoring or detection period). When the rate of loss is significant, the complex can dissociate before it can be detected.

Two technical issues impact detection of multicomponent complexes when using components that include detectable labels. First, signals originating from the labeled component can undesirably obscure detection of specific complexes due to high backgrounds. Second, conventional washing to remove one or more components from the system can promote dissociation of the reversible complexes that are to be detected. Each of these can be a liability when gathering sequencing data.

The importance of maintaining steady binding signals can be appreciated in the context of flow cell applications, where multiple images are typically gathered. For example, a flow cell can include a surface area greater than a single field of view for an optical imaging system. As a consequence, an optical system may have to gather images of different parts of the flow cell by moving an optical package (e.g., lenses, cameras, illuminating apparatus, etc.) from one part to another, pausing to stabilize the system, gather an image, and repeat the process. This extends processing time. If transient complexes to be monitored are unstable, then it is possible that only low-quality data—if any—will be acquired for the later images acquired in an optical scanning step. As set forth herein, this problem can be overcome by stabilizing complexes under a condition that permits acquisition of data with high signal-to-background ratios.

As detailed below, simultaneously stabilizing ternary complexes while removing non-complexed components (e.g., excess labeled polymerase, or labeled nucleotide remaining in solution) from the binding reaction mixture can be used to overcome this problem. This can involve, for example, immobilizing the ternary complex to a solid support, and then flushing or washing the system using a fluid in which the labeled reagent(s) are substantially insoluble. By this approach, components of preformed multicomponent complexes cannot substantially partition into the stabilizing fluid used in the imaging wash, or flush step, and so association of the different components or constituents of the complex is maintained. While not wishing to be limited by any particular theory of operation, it is possible that some multicomponent complexes can be precipitated or encapsulated in place to maintain integrity of the complex. Whether or not structural interaction between components of the ternary complex remain in native or precipitated form following contact with the stabilizing fluid, both the polymerase and the nucleotide remain localized with the immobilized primed template nucleic acid. For simplicity, this aggregation of the immobilized primed template nucleic acid molecule, the polymerase and the cognate nucleotide can be referred to using the term, "ternary complex."

Advantageously, signals associated with immobilized complexes can be highly stable when using the disclosed technique. By this it is meant that complexes in contact with a stabilizing fluid can remain detectable over the course of from between 1-10 minutes, or between 1-5 minutes, or between 2-5 minutes, or between 3-5 minutes, or even more than 10 minutes. Of course, it may be desirable to detect ternary complexes after a shorter period of time (e.g., after 10-60 seconds, or after 30-60 seconds) following initial contact with the stabilizing fluid. In some particular embodiments, detecting a ternary complex is performed between 10 seconds and 10 minutes following contact with the stabilizing fluid. In some embodiments, the ternary complex is detectable after 5 minutes in the stabilizing fluid.

These stability ranges can easily exceed the time needed to make a measurement that would identify the labeled component of the complex. For example, this extent of stabilization is sufficient to permit imaging of multiple different parts or sections of a flow cell using a "tiling" approach, where an aggregated collection of imaged sections represents the flow cell surface.

Use of Stabilizing Fluids to Reduce Background Signal

Reducing the solution-phase concentration of one or more of the constituents of a reversible or transient complex that is in dynamic equilibrium with its chemical environment can lead to dissociation and loss of the complex. For example, washing immobilized ternary complexes with nucleotide-free and polymerase-free aqueous examination buffer to deplete non-complexed labeled reagents from the surrounding solution desirably can reduce background signal to permit detection of specific complexes, but undesirably may impose limits or requirements on the timing of the detection, or may require undesirably complicated data processing to identify a cognate ligand. Commonly assigned U.S. patent application Ser. No. 15/581,828, published as U.S. 2017/0314064 A1 (the entire disclosure of which is incorporated by reference herein), details this phenomenon and describes how destabilization of the ternary complex can be used to make cognate nucleotide identification. It would be desirable to further improve reliability of detection assays for receptor-ligand interactions, particularly those employing detectably labeled (e.g., fluorescently labeled) components of the complex, by enhancing signal-to-background ratios in a manner that facilitates detection of the complexes over an extended period. Stabilizing fluids in accordance with the disclosure can be used for this purpose. As confirmed by the working Examples herein, stabilizing fluids in accordance with the disclosure can be used with Sequencing By Binding™ procedures employing either labeled nucleotides or labeled polymerases.

Stabilizing fluids useful for simultaneously removing soluble components of a complex from the vicinity of an immobilized complex, and for stabilizing the complex against dissociation can be defined by certain chemical features or characteristics. Certain preferred stabilizing fluids exhibit either substantially no capacity, or only a sparing capacity to solubilize the detectably labeled constituent (e.g., labeled nucleotide or labeled polymerase) of the complex that is to be detected. Thus, if a ternary complex that is to be detected includes an immobilized primed template nucleic acid molecule, then the labeled nucleotide can be insoluble, or only sparingly soluble (i.e., "substantially insoluble") in the stabilizing fluid. When this is the case, the stabilizing fluid can at least partially displace or replace solution-phase nucleotide and polymerase in contact with an immobilized ternary complex without promoting dissociation of that complex. Preferably, this displacement or replacement (whether partial or complete) occurs within a flow cell, and is effected by flowing the stabilizing fluid into and through a flow cell containing the immobilized ternary complex to be detected. Generally speaking, any volume of the stabilizing fluid will be unavailable for partitioning of the labeled constituent(s) of the immobilized ternary complex. This effectively stabilizes the complex by inhibiting or preventing its dissociation. At the same time, non-complexed polymerase and nucleotide remaining free in solution can be removed from contact with the complex by displacement with the stabilizing fluid.

Examples of stabilizing fluids in which nucleotides (e.g., labeled nucleotides) and polymerases (e.g., labeled polymerases) are substantially insoluble include, without limitation: mineral oils or paraffin oils (e.g., mixtures of higher alkanes having 9 or more carbons); purified higher alkanes (e.g., decane); silicone oil (e.g., 100% silicone oil); perfluorocarbons (e.g., Fluorinert™ available from the 3M Company, MN); ethanol (e.g., 100% or about 70% ethanol); isopropanol (e.g., 100%, or 80% isopropanol in a buffered aqueous solution); 2-butanol (soluble in 12 parts water); and even a gas or air.

Stabilizing fluids can be either water-miscible (e.g., ethanol, isopropanol, etc.) or water-immiscible (e.g., mineral oil, silicone oil, air, etc.) fluids, as long as the detectably labeled constituent of the ternary complex does not substantially partition or distribute from the immobilized complex into the stabilizing fluid used in the imaging wash step. In some embodiments, a stabilizing fluid may have low solubility in an aqueous fluid but the amount of stabilizing fluid used is oversaturating such that a substantial volume of the stabilizing fluid does not dissolve in the aqueous fluid. References herein to use of a stabilizing fluid that is immiscible in water or an aqueous fluid will be understood to include, for example, the use of an amount of stabilizing fluid that yields a volume of stabilizing fluid that is immiscible in water or in the aqueous fluid. As such, a stabilizing fluid and an aqueous fluid can form separate fluid phases within a vessel such as a flow cell.

In accordance with embodiments of the imaging wash techniques set forth herein, the labeled constituent (e.g., labeled nucleotides or labeled polymerases) or the complex to be detected preferably is either insoluble or only sparingly soluble (i.e., substantially insoluble) in the stabilizing fluid. This is the case for water-miscible and water-immiscible stabilizing fluids. For example, the polymerase and cognate nucleotide that form a ternary complex at a feature that includes an immobilized primed template nucleic acid molecule are preferably soluble in the stabilizing fluid at a level that is less than 0.01, more preferably less than 0.001, and yet still more preferably less than 0.0001 of the solubility in an examination buffer used for providing the polymerase and nucleotide to the immobilized primed template nucleic acid molecule to assemble the ternary complex.

To maintain stability of complexes (e.g., ternary complexes) which are in dynamic equilibrium with an aqueous environment within a flow cell, the stabilizing fluid can be substantially free of polymerase and/or nucleotide. This can avoid exchange of the labeled components of ternary complexes that are to be detected. This follows from the dynamic nature of ternary complexes that are detected using the Sequencing By Binding™ platform.

Imaging Wash to Reduce Nonspecific Background while Maintaining Signal Strength for Ternary Complexes in Model Sequencing by Binding™ Systems Procedures employing either detectably labeled polymerases or detectably labeled nucleotides can benefit from techniques that enhance signal-to-background ratios when detection of the label indicates the presence or identity of the nucleotide. This is especially the case for Sequencing By Binding™ procedures employing labeled nucleotides (e.g., fluorescently labeled nucleotide analogs) because nucleotide concentrations typically are higher than polymerase concentrations. Large excesses of a signal-producing component (i.e., labeled nucleotide) can confound detection of signal arising from ternary complexes as the result of high background signals. High background signals can result from either non-complexed fluorescent nucleotides or fluorescent polymerase that remain in the solution phase at the time the fluorescent signal is detected or measured.

As discussed elsewhere herein, aqueous wash steps can sometimes undesirably promote dissociation of ternary complexes that are desired to be detected. While this phenomenon can be exploited for identifying cognate nucleotides by monitoring ternary complex destabilization, there also can be problems with signal loss due to the dynamic nature of the complex being detected. It was discovered that transient binding assays employing labeled nucleotides or labeled polymerases could experience compromised signal-to-background readings as the result of high non-specific signals (e.g., fluorescent signals); and that removing non-complexed labeled reagents using a standard wash step could promote signal loss due to the dynamic nature of the ternary complex.

This heretofore unappreciated combination of issues was addressed using a "flush" or "wash" step to remove non-complexed labeled reagents from the feature or site monitored for ternary complex formation (e.g., within a flow cell or other reaction chamber or vessel), where the step employed a stabilizing fluid reagent. In some applications, the stabilizing fluid was immiscible with the fluid reagent containing the nucleotide, polymerase, and immobilized primed template nucleic acid molecule that combined to form the ternary complex.

Use of an imaging wash in the flush step can advantageously reduce the magnitude of optical signals arising from labeled components (e.g., fluorescent nucleotides or fluorescent polymerases) remaining free in the solution phase (i.e., non-complexed labeled nucleotide). For example, excess cognate nucleotide harboring a fluorescent label and remaining in the bulk solution phase within a flow cell can generate an optical signal that obscures the fluorescent signal arising from cognate nucleotide present in ternary complexes immobilized to a surface. Because ternary complexes that form without chemical incorporation in the Sequencing By Binding™ workflow are in a dynamic equilibrium (i.e., where rates of formation and dissociation are balanced), flushing or washing the flow cell with an aqueous solution devoid of polymerase and/or cognate nucleotide to remove non-complexed nucleotide can sometimes promote rapid signal decay of ternary complexes containing labeled nucleotide. This led to a search for methods that could reduce signal arising from non-complexed fluorescent nucleotides while substantially maintaining the integrity of ternary complexes.

In certain preferred approaches, a stabilizing fluid can be immiscible with the aqueous examination solution that includes polymerase and labeled nucleotide. The immiscible fluid can be an organic reagent (e.g., an oil, such as a paraffin oil), inorganic reagent (e.g., silicone oil), or a gas (e.g., argon, nitrogen, or even air). Each of these categories of reagent has been used with good results.

Advantageously, and surprisingly, ternary complexes that included the polymerase and labeled cognate nucleotide complexed with immobilized primed template nucleic acid remained highly stable in the presence of the stabilizing fluid (e.g., a non-aqueous stabilizing fluid). Working Examples presented below illustrate how ternary complexes remained substantially intact and were not substantially destabilized during a non-aqueous flush step. This permitted detection of ternary complexes during the imaging wash step, when signal-to-background ratios were favorable for cognate nucleotide identification.

In other embodiments, aqueous fluids that maintain ternary complexes in the absence of non-bound labeled nucleotides, or non-bound labeled polymerase, also can be used during the imaging wash step. For example, ternary complexes can be maintained under these conditions by slowing the rate of complex dissociation.

Certain Illustrative Workflows

The cognate nucleotide identification workflow can be optimized by incorporating a reversible terminator nucleotide into a primed template nucleic acid, and then examining ternary complex formation with the product of the incorporation reaction in the same reaction mixture (i.e., in a single step, and without intervening removal of reversible terminator nucleotides). The procedure becomes even more rapid when four distinguishably labeled nucleotides are processed in the reaction, and ternary complexes detected using single-scan imaging (i.e., where complexes including any of the labeled nucleotides can be detected and distinguished from each other).

In accordance with a different approach, the workflow is streamlined in an alternative way. Here, a reversible terminator nucleotide is incorporated in a first reaction mixture, and dynamic equilibrium binding of labeled nucleotide in a ternary complex is detected in a second reaction mixture. When the labeled nucleotides are non-incorporable nucleotides, a single step can be used for dissociating and removing ternary complexes, and for simultaneously cleaving and removing reversible terminator moieties to relieve the block to primer extension.

Generally speaking, the cognate nucleotide identification method can be applied either to an individual nucleic acid feature or to a population of features that may differ in sequence relative to one another. For example, the method may be applied to identification of cognate nucleotides for a population of different spaced-apart nucleic acid features immobilized to a surface or solid support (e.g., within a flow cell, or sell of a multiwell plate). As discussed above, exemplary nucleic acid features include in situ- or ex situ-generated nucleic acid amplification products, possibly disposed on beads.

Combined Blocking-and-Examination Step (Alternative 1)

In one aspect, the workflow procedure concerns a method of identifying cognate nucleotides. The process can begin with the step of (a) contacting nucleic acid features with a first reagent solution that includes various components to result in a reaction mixture competent for blocking-and-examining the primed template nucleic acid undergoing analysis. For example, the reagent typically includes a plurality of reversible terminator nucleotides, a plurality of distinguishably labeled non-incorporable nucleotide analogs, at least one polymerase, and a catalytic metal ion. This can be accomplished by flowing the first reagent solution through a flow cell. As a result of this contact, one of the reversible terminator nucleotides incorporates into the primed template nucleic acid to result in a blocked primed template nucleic acid that is precluded from participating in subsequent polymerization reactions. The presence of a reversible terminator moiety on the 3' nucleotide of the primer strand renders the primer strand incapable of participating in enzymatic formation of a phosphodiester bond. This limits the incorporation reaction to adding only a single reversible terminator nucleotide for each contacting cycle. However, the presence of distinguishably labeled nucleotide in the same reaction permits assembly or formation of a stabilized ternary complex, which can be detected simply by detecting localization of labeled nucleotide to the position of the nucleic acid feature. It should be clear that detection of the cognate nucleotide results from detection of the distinguishable label associated with that localizing nucleotide. More particularly, the distinguishable label identifies the nucleotide base participating in the ternary complex (i.e., the distinguishable label can be said to be "base-specific"). The detecting procedure can involve the step of: (b) detecting in the reaction mixture from step (a), ternary complexes that include the blocked primed template nucleic acid, one of the polymerases, and one of the distinguishably labeled non-incorporable nucleotide analogs, again by detecting the label attached to the nucleotide analog. For example, if the distinguishably labeled non-incorporable nucleotide analog includes a fluorescent moiety, then the detecting step will involve detecting that fluorescent moiety. Next, there is the step of: (c) identifying cognate nucleotides for the different immobilized primed template nucleic acid molecules by identifying the distinguishably labeled non-incorporable nucleotide analogs of the ternary complexes that were detected. Again, the base-specificity of the different distinguishable labels (e.g., dATP being associated with a label distinguishable from the labels associated with dGTP, dCTP, and dTTP) means that detecting the distinguishable label is sufficient to identify the cognate nucleotide.

According to one generally preferred embodiment, the plurality of reversible terminator nucleotides includes four reversible terminator nucleotides, and the plurality of distinguishably labeled non-incorporable nucleotides includes four distinguishably labeled non-incorporable nucleotide analogs.

More preferably, at least one of the four distinguishably labeled non-incorporable nucleotide analogs includes a fluorescent label, and none of the four distinguishably labeled non-incorporable nucleotide analogs includes an intercalating dye that changes fluorescence after contacting DNA.

Alternatively, when the plurality of reversible terminator nucleotides includes four reversible terminator nucleotides, and when the plurality of distinguishably labeled non-incorporable nucleotides includes four distinguishably labeled non-incorporable nucleotide analogs, each of the four distinguishably labeled non-incorporable nucleotide analogs can include a different detectable label.

More preferably, step (b) involves detecting the different detectable labels of the four distinguishably labeled non-incorporable nucleotide analogs.

In another preferred embodiment, when each of the four distinguishably labeled non-incorporable nucleotide analogs includes a different detectable label, each of the different detectable labels can includes a different fluorescent label.

Alternatively, when the plurality of reversible terminator nucleotides includes four reversible terminator nucleotides, and when the plurality of distinguishably labeled non-incorporable nucleotides includes four distinguishably labeled non-incorporable nucleotide analogs, each of the four reversible terminator nucleotides can include a reversible terminator moiety, and each of the four distinguishably labeled non-incorporable nucleotide analogs can include a different fluorescent label.

Alternatively, when the plurality of reversible terminator nucleotides includes four reversible terminator nucleotides, and when the plurality of distinguishably labeled non-incorporable nucleotides includes four distinguishably labeled non-incorporable nucleotide analogs, each of the four reversible terminator nucleotides can include a reversible terminator moiety, and each of the four distinguishably labeled non-incorporable nucleotide analogs can include a different detectable label. Here none of the different detectable labels is an intercalating dye that changes fluorescence after contacting DNA.

According to one preferred embodiment, when the plurality of reversible terminator nucleotides includes four reversible terminator nucleotides, when the plurality of distinguishably labeled non-incorporable nucleotides includes four distinguishably labeled non-incorporable nucleotide analogs, when each of the four reversible terminator nucleotides can include a reversible terminator moiety, and when each of the four distinguishably labeled non-incorporable nucleotide analogs includes a different fluorescent label, each of the different fluorescent labels is covalently attached to one of the four distinguishably labeled non-incorporable nucleotide analogs at a position on its base moiety.

According to a different preferred embodiment, when the plurality of reversible terminator nucleotides includes four reversible terminator nucleotides, when the plurality of distinguishably labeled non-incorporable nucleotides includes four distinguishably labeled non-incorporable nucleotide analogs, when each of the four reversible terminator nucleotides includes a reversible terminator moiety, and when each of the four distinguishably labeled non-incorporable nucleotide analogs can include a different fluorescent label, each of the four distinguishably labeled non-incorporable nucleotide analogs includes a triphosphate group with a modified linkage between alpha and beta phosphorus atoms.

More preferably, each of the different fluorescent labels is covalently attached to one of the four distinguishably labeled non-incorporable nucleotide analogs at a position on its base moiety.

Optionally, one or more labeled non-incorporable nucleotide analogs have a linkage to the label as shown in Formula (1a), (1b), (1c), (1d), (2a), (2b), (2c), (2d), (3a), (3b), (3c) or (3d). Optionally, one or more labeled non-incorporable nucleotide analogs have a linkage to the label as shown in FIG. 2.

Alternatively, when plurality of reversible terminator nucleotides includes four reversible terminator nucleotides, and when the plurality of distinguishably labeled non-incorporable nucleotides includes four distinguishably labeled non-incorporable nucleotide analogs, each of the four distinguishably labeled non-incorporable nucleotide analogs includes a different fluorescent label, and the four reversible terminator nucleotides do not include distinguishable fluorescent labels.

Alternatively, when the plurality of reversible terminator nucleotides includes four reversible terminator nucleotides, and when the plurality of distinguishably labeled non-incorporable nucleotides includes four distinguishably labeled non-incorporable nucleotide analogs, each of the four reversible terminator nucleotides includes a 3'-OH modification.

For example, the 3'-OH modification may involve a 3'-ONH$_2$ moiety.

Alternatively, when the plurality of reversible terminator nucleotides includes four reversible terminator nucleotides, and when the plurality of distinguishably labeled non-incorporable nucleotides includes four distinguishably labeled non-incorporable nucleotide analogs, there can be the further steps of: (d) replacing the first reagent with a second reagent that destabilizes ternary complexes; and (e) replacing the second reagent with a third reagent that removes a reversible terminator moiety from each of the blocked primed template nucleic acid molecules.

In certain instances, step (d) takes place before step (c), and step (c) is performed using results from step (b) that have been stored electronically.

Alternatively, when the plurality of reversible terminator nucleotides includes four reversible terminator nucleotides, and when the plurality of distinguishably labeled non-incorporable nucleotides includes four distinguishably labeled non-incorporable nucleotide analogs, the catalytic metal ion of the first reagent can be Mg$^{2+}$ ion, or Mn$^{2+}$ ion.

In another preferred embodiment, when the plurality of reversible terminator nucleotides includes four reversible terminator nucleotides, when the plurality of distinguishably labeled non-incorporable nucleotides includes four distinguishably labeled non-incorporable nucleotide analogs, and when there are the further steps of: (d) replacing the first reagent with a second reagent that destabilizes ternary complexes, and (e) replacing the second reagent with a third reagent that removes a reversible terminator moiety from each of the blocked primed template nucleic acid molecules, steps (a)-(e) can be repeated to identify successive cognate nucleotides for each of the different primed template nucleic acid molecules undergoing processing.

In a different preferred embodiment, when at least one of the four distinguishably labeled non-incorporable nucleotide analogs includes a fluorescent label, and none of the four distinguishably labeled non-incorporable nucleotide analogs includes an intercalating dye that changes fluorescence after contacting DNA, the one of the polymerases in step (b) does not include an exogenous label that is in energy transfer relationship with the fluorescent label of any of the distinguishably labeled non-incorporable nucleotide analogs, and the catalytic metal ion of the first reagent is either Mg$^{2+}$ ion, or Mn$^{2+}$ ion.

According to another generally preferred embodiment, at least one of the distinguishably labeled non-incorporable nucleotide analogs includes a fluorescent label, and none of the distinguishably labeled non-incorporable nucleotide analogs includes an intercalating dye that changes fluorescence after contacting DNA.

According to another generally preferred embodiment, each of the plurality of distinguishably labeled non-incorporable nucleotide analogs includes a different detectable label.

More preferably, step (b) involves detecting the different detectable labels of the plurality of distinguishably labeled non-incorporable nucleotide analogs.

Alternatively, when each of the plurality of distinguishably labeled non-incorporable nucleotide analogs includes a different detectable label, each of the different detectable labels can include a different fluorescent label.

According to another generally preferred embodiment, each of the plurality of reversible terminator nucleotides includes a reversible terminator moiety, and each of the plurality of distinguishably labeled non-incorporable nucleotide analogs includes a different fluorescent label.

According to another generally preferred embodiment, each of the plurality of reversible terminator nucleotides includes a reversible terminator moiety, each of the plurality of distinguishably labeled non-incorporable nucleotide analogs includes a different detectable label, and none of the different detectable labels is an intercalating dye that changes fluorescence after contacting DNA.

Alternatively, when each of the plurality of reversible terminator nucleotides includes a reversible terminator moiety, and when each of the plurality of distinguishably labeled non-incorporable nucleotide analogs includes a different fluorescent label, each of the different fluorescent labels can be covalently attached to one of the plurality of distinguishably labeled non-incorporable nucleotide analogs at a position on its base moiety.

Alternatively, when each of the plurality of reversible terminator nucleotides includes a reversible terminator moiety, and when each of the plurality of distinguishably labeled non-incorporable nucleotide analogs includes a different fluorescent label, each of the plurality of distinguishably labeled non-incorporable nucleotide analogs includes a triphosphate group with a modified linkage between alpha and beta phosphorus atoms.

More preferably, each of the different fluorescent labels is covalently attached to one of the plurality of distinguishably labeled non-incorporable nucleotide analogs at a position on its base moiety.

According to another generally preferred embodiment, each of the plurality of distinguishably labeled non-incorporable nucleotide analogs includes a different fluorescent label, and the plurality of reversible terminator nucleotides do not include distinguishable fluorescent labels.

According to another generally preferred embodiment, each of the plurality of reversible terminator nucleotides includes a 3'-OH modification.

More preferably, the 3'-OH modification involves a 3'-ONH$_2$ moiety.

According to another generally preferred embodiment, there are the further steps of: (d) replacing the first reagent with a second reagent that destabilizes ternary complexes; and (e) replacing the second reagent with a third reagent that removes a reversible terminator moiety from each of the blocked primed template nucleic acid molecules.

In one version, step (d) takes place before step (c), and step (c) is performed using results from step (b) that have been stored electronically.

According to another generally preferred embodiment, the catalytic metal ion of the first reagent is either Mg$^{2+}$ ion, or Mn$^{2+}$ ion.

According to another generally preferred embodiment, when there are the further steps of: (d) replacing the first reagent with a second reagent that destabilizes ternary complexes; and (e) replacing the second reagent with a third reagent that removes a reversible terminator moiety from each of the blocked primed template nucleic acid molecules; steps (a)-(d) can be repeated to identify successive cognate nucleotides for each of the different primed template nucleic acid molecules.

According to another generally preferred embodiment, at least one of the distinguishably labeled non-incorporable nucleotide analogs includes a fluorescent label, and none of the distinguishably labeled non-incorporable nucleotide analogs includes an intercalating dye that changes fluorescence after contacting DNA; and the one of the polymerases in step (b) does not include an exogenous label in energy transfer relationship with the fluorescent label of any of the distinguishably labeled non-incorporable nucleotide analogs, and the catalytic metal ion of the first reagent is either $Mg^{2+}$ ion, or $Mn^{2+}$ ion.

Combined Blocking-and-Examination Step (Alternative 2)

In another aspect, the workflow procedure concerns a method of identifying a cognate nucleotide within the sequence of a primed template nucleic acid molecule. The process can begin with the step of: (a) contacting the primed template nucleic acid molecule with a first reagent to create a first reaction mixture. The first reagent used in the procedure includes at least one polymerase, a catalytic metal ion, one or more nucleotide analogs that include a reversible terminator moiety, and one or more labeled nucleotide analogs. Each labeled nucleotide analog includes a nucleotide base-specific label. As a consequence of this contact, a single nucleotide analog that includes the reversible terminator moiety incorporates into the primed template nucleic acid molecule at the N+1 position thereof to produce a reversibly blocked primed template nucleic acid molecule. There also is the step of: (b) detecting, in the first reaction mixture, formation of a stabilized ternary complex that includes the reversibly blocked primed template nucleic acid molecule, one of the polymerases, and one of the labeled nucleotide analogs. Next, there is the step of: (c) identifying the cognate nucleotide for the N+2 position of the primed template nucleic acid molecule by identifying the nucleotide base-specific label present in the stabilized ternary complex.

According to one generally preferred embodiment, each nucleotide base-specific label includes a fluorescent moiety indicating nucleotide base identity.

According to another generally preferred embodiment, each nucleotide base-specific label includes a base-specific fluorescent moiety that does not substantially change fluorescence after binding to DNA. Thus, the base-specific fluorescent moiety is not an intercalating dye.

Optionally, one or more labeled nucleotide analogs are attached to a label via a linker shown in Formula (1a), (1b), (1c), (1d), (2a), (2b), (2c), (2d), (3a), (3b), (3c) or (3d). Optionally, one or more labeled nucleotide analogs are attached to a label via a linker shown in FIG. 2.

According to another generally preferred embodiment, each nucleotide base-specific label includes a base-specific fluorescent moiety, and neither the nucleotide analog that includes the reversible terminator moiety nor the at least one polymerase harbors or includes an energy transfer partner that is required for detecting formation of the stabilized ternary complex in step (b). Thus, detection does not require any FRET relationship.

According to another generally preferred embodiment, the nucleotide analog that includes the reversible terminator moiety is an unlabeled nucleotide analog that does not also include a fluorescent moiety.

According to another generally preferred embodiment, each labeled nucleotide analog is a non-incorporable nucleotide analog.

According to another generally preferred embodiment, there is the additional step of: (d) contacting the reversibly blocked primed template nucleic acid molecule with a second reagent that destabilizes ternary complexes; and (e) contacting the reversibly blocked primed template nucleic acid molecule with a third reagent that removes the reversible terminator moiety from the reversibly blocked primed template nucleic acid molecule.

More preferably, there also can be the additional step of: (f) repeating steps (a)-(e) to determine the next cognate nucleotide within the sequence of the primed template nucleic acid molecule.

According to another generally preferred embodiment, when each nucleotide base-specific label includes a base-specific fluorescent moiety that does not substantially change fluorescence after binding to DNA, neither the nucleotide analog that includes the reversible terminator moiety nor the at least one polymerase harbors or includes an energy transfer partner required for detecting formation of the stabilized ternary complex in step (b). Thus, detection does not require any FRET relationship.

More preferably, the nucleotide analog that includes the reversible terminator moiety is an unlabeled nucleotide analog that does not also include a fluorescent moiety.

Still more preferably, each labeled nucleotide analog is a non-incorporable nucleotide analog.

Yet still more preferably, there is the further step of: (d) contacting the reversibly blocked primed template nucleic acid molecule with a second reagent that destabilizes ternary complexes; and (e) contacting the reversibly blocked primed template nucleic acid molecule with a third reagent that removes the reversible terminator moiety from the reversibly blocked primed template nucleic acid molecule.

Even more preferably, the method further involves the step of: (f) repeating steps (a)-(e) to determine the next cognate nucleotide within the sequence of the primed template nucleic acid molecule.

According to another generally preferred embodiment, the nucleotide analogs are distinguishably labeled reversible terminator nucleotides.

Combined Blocking-and-Examination Step (Alternative 3)

In another aspect, the workflow procedure concerns a method of identifying a cognate nucleotide within the sequence of a primed template nucleic acid molecule. The process can begin with the step of: (a) contacting the primed template nucleic acid molecule with a first reagent to create a first reaction mixture. The first reagent includes at least one polymerase, a catalytic metal ion, and four reversible terminator nucleotide analogs. Each of the reversible terminator nucleotide analogs includes a different base and a distinguishable base-specific label. As a consequence of this contacting, one of the reversible terminator nucleotide analogs incorporates into the primed template nucleic acid molecule at the N+1 position thereof to produce a reversibly blocked primed template nucleic acid molecule. There also is the step of: (b) detecting, in the first reaction mixture, formation of a stabilized ternary complex that includes the reversibly blocked primed template nucleic acid molecule, one of the polymerases, and one of the reversible terminator nucleotide analogs. There also can be the step of: (c) identifying the cognate nucleotide for the N+2 position of the primed template nucleic acid molecule by identifying the distinguishable base-specific label present in the stabilized ternary complex.

According to one generally preferred embodiment, each of the distinguishable base-specific labels is covalently linked to a moiety that is removed from the reversible terminator nucleotide analog upon incorporation into the primed template nucleic acid molecule.

More preferably, each of the distinguishable base-specific labels is covalently linked to a phosphate moiety.

According to another generally preferred embodiment, each of the reversible terminator nucleotide analogs is linked to a reversible terminator moiety at the 3' position of the sugar moiety.

According to another generally preferred embodiment, there are the additional steps of: (d) contacting the reversibly blocked primed template nucleic acid molecule with a second reagent that destabilizes ternary complexes; and (e) contacting the reversibly blocked primed template nucleic acid molecule with a third reagent that removes the reversible terminator moiety from the reversibly blocked primed template nucleic acid molecule.

More preferably, there is the additional step of: (f) repeating steps (a)-(e) to determine the next cognate nucleotide within the sequence of the primed template nucleic acid molecule.

According to another generally preferred embodiment, the primed template nucleic acid molecule is contained within a flow cell, and step (a) involves flowing the first reagent through the flow cell.

According to another generally preferred embodiment, each nucleotide base-specific label includes a fluorescent moiety indicating nucleotide base identity.

According to another generally preferred embodiment, each nucleotide base-specific label includes a base-specific fluorescent label that does not substantially change fluorescence after binding to DNA.

Optionally, one or more reversible terminator nucleotide analogs are attached to a label via a linker shown in Formula (1a), (1b), (1c), (1d), (2a), (2b), (2c), (2d), (3a), (3b), (3c) or (3d). Optionally, one or more reversible nucleotide analogs are attached to a label via a linker shown in FIG. 2.

According to another generally preferred embodiment, each nucleotide base-specific label includes a base-specific fluorescent label, and neither the nucleotide analog that includes the reversible terminator moiety, nor the at least one polymerase that includes an energy transfer partner required for detecting formation of the stabilized ternary complex in step (b).

According to another generally preferred embodiment, the nucleotide analog that includes the reversible terminator moiety is an unlabeled nucleotide analog that does not also include a fluorescent label.

Combined Blocking-and-Examination Step (Alternative 4)

In another aspect, the workflow procedure concerns a method of identifying cognate nucleotides for each of a plurality of nucleic acid features, where each feature includes a primed template nucleic acid molecule. The process can begin with the step of: (a) preparing first stabilized ternary complexes at each of the plurality of nucleic acid features, each stabilized ternary complex including the primed template nucleic acid molecule at its respective nucleic acid feature, a reversible terminator nucleotide, and a polymerase. Next, there is the step of: (b) contacting the first stabilized ternary complexes from step (a) with a reagent that includes a catalytic metal ion, at least one distinguishably labeled incorporable nucleotide, and a polymerase, to produce a reaction mixture. As a consequence of this contacting, the reversible terminator nucleotide incorporates into the primed template nucleic acid molecule to produce a blocked primed template nucleic acid molecule at each of the plurality of nucleic acid features. As well, there forms at each of the plurality of nucleic acid features a second stabilized ternary complex that includes the blocked primed template nucleic acid molecule and one of the distinguishably labeled incorporable nucleotides. Next, there is the step of: (c) identifying cognate nucleotides for the primed template nucleic acid molecules at each of the plurality of nucleic acid features by detecting, in the reaction mixture, a label joined to the distinguishably labeled incorporable nucleotide of the second stabilized ternary complex.

According to one generally preferred embodiment, step (a) includes preparing, in a first reaction mixture, the first stabilized ternary complexes; and step (b) includes contacting in a second reaction mixture, that is different from the first reaction mixture, the first stabilized ternary complexes.

According to another generally preferred embodiment, the reversible terminator nucleotide is unlabeled, and includes a reversible terminator moiety.

According to another generally preferred embodiment, the polymerases in the first and second reaction mixtures are identical.

According to another generally preferred embodiment, each of the plurality of nucleic acid features is contained in a flow cell.

According to another generally preferred embodiment, the catalytic metal ion in the second reaction mixture is either $Mg^{2+}$ ion, or $Mn^{2+}$ ion.

According to another generally preferred embodiment, none of at least one distinguishably labeled incorporable nucleotide includes a reversible terminator moiety.

According to another generally preferred embodiment, each of the at least one distinguishably labeled incorporable nucleotide includes a distinguishable fluorescent label, and wherein the label detected in the second reaction mixture is one of the distinguishable fluorescent labels.

According to another generally preferred embodiment, the at least one distinguishably labeled incorporable nucleotide of the second reaction mixture includes four distinguishably labeled incorporable nucleotides.

Optionally, one or more distinguishably labeled incorporable nucleotides are attached to a label via a linker shown in Formula (1a), (1b), (1c), (1d), (2a), (2b), (2c), (2d), (3a), (3b), (3c) or (3d). Optionally, one or more distinguishably labeled incorporable nucleotides are attached to a label via a linker shown in FIG. 2.

According to another generally preferred embodiment, the method further includes the step of: (d) preparing a third reaction mixture by contacting the second stabilized ternary complex with one or more wash reagents that destabilize ternary complexes and remove a reversible terminator moiety of each of the reversible terminator nucleotide. As a consequence, 3'-ends of each of the primed template nucleic acid molecules are made available for polymerization.

More preferably, the method further involves repeating steps (a)-(d).

In a particular example of the generalized approach, there is a method of identifying cognate nucleotides for each of a plurality of nucleic acid features, where each feature includes a primed template nucleic acid molecule. The method can begin with the step of: (a) contacting the plurality of nucleic acid features with a first reagent to produce a first reaction mixture, where the first reagent includes a first polymerase, four reversible terminator nucleotides, and a non-catalytic metal ion that inhibits incorporation and stabilizes ternary complex formation. As a consequence of the contact, there forms, without incorporation, a plurality of first stabilized complexes. Each of the plurality of first stabilized complexes includes one of the primed template nucleic acid molecules, the first polymerase, and one of the reversible terminator nucleotides. Next, there is the step of: (b) contacting the plurality of first stabilized complexes with a second reagent to produce a second reaction mixture. The second reagent includes a second polymerase, four distinguishably labeled nucleotides, and a catalytic metal ion. As a consequence, the reversible terminator nucleotide of each of the plurality of first stabilized complexes incorporates into primers of the primed template nucleic acid molecules to produce a blocked primed template nucleic acid molecule at each of the plurality of nucleic acid features. There forms at each of the plurality of nucleic acid features, as a result, a second stabilized complex that includes the blocked primed template nucleic acid molecule, the second polymerase, and one of the distinguishably labeled nucleotides. Next, there is the step of: (c) identifying cognate nucleotides for the primed template nucleic acid molecules at the plurality of nucleic acid features by detecting, in the second reaction mixture, a label joined to the distinguishably labeled nucleotide of the second stabilized complex.

Procedure Optionally Employing Combined Deblock and Wash Step

In one aspect, the workflow procedure concerns a method of identifying a next correct nucleotide within the sequence of a primed template nucleic acid molecule. The process can begin with the step of: (a) incorporating a reversible terminator nucleotide into the primed template nucleic acid molecule to produce a blocked primed template nucleic acid molecule. Next, there is the step of: (b) contacting the blocked primed template nucleic acid molecule with a first reagent that includes: (i) a polymerase, and (ii) at least one labeled nucleotide analog. Each labeled nucleotide analog includes a distinguishable label specific for the base of that nucleotide analog. As a consequence of the contacting, there forms a stabilized ternary complex that includes each of: the blocked primed template nucleic acid molecule, the polymerase, and the labeled nucleotide analog that is the next correct nucleotide. Next, there is the step of: (c) detecting the distinguishable label of the labeled nucleotide analog of the stabilized ternary complex, thereby identifying the next correct nucleotide within the primed template nucleic acid molecule.

According to one generally preferred embodiment, the reversible terminator nucleotide is an unlabeled reversible terminator nucleotide.

According to another generally preferred embodiment, each of the at least one labeled nucleotide analog in step (b) is at least one labeled non-incorporable nucleotide analog, and step (c) involves detecting the distinguishable label of the labeled non-incorporable nucleotide analog of the stabilized ternary complex, thereby identifying the next correct nucleotide within the primed template nucleic acid molecule.

More preferably, the distinguishable label of the labeled non-incorporable nucleotide analog present in the stabilized ternary complex includes a fluorescent label, and the fluorescent label is not an intercalating dye that changes fluorescence after contacting DNA.

More preferably, neither the reversible terminator nucleotide nor the at least one polymerase includes an energy transfer partner required for detecting the fluorescent label in step (c).

Alternatively, when each of the at least one labeled nucleotide analog in step (b) is at least one labeled non-incorporable nucleotide analog; when step (c) involves detecting the distinguishable label of the labeled non-incorporable nucleotide analog of the stabilized ternary complex, thereby identifying the next correct nucleotide within the primed template nucleic acid molecule; the first reagent further can include a divalent catalytic metal ion.

More preferably, there is the further step of: (d) contacting the blocked primed template nucleic acid molecule, after step (c), with a second reagent that destabilizes ternary complexes and removes the reversible terminator moiety, whereby the blocked primed template nucleic acid molecule is deblocked and made available for polymerization.

More preferably, there is the further step of: (e) repeating steps (a)-(c) using the deblocked product of step (d) as the primed template nucleic acid molecule to determine a next correct nucleotide within the sequence of the primed template nucleic acid molecule.

According to another generally preferred embodiment, each of the at least one labeled nucleotide analog in step (b) is at least one labeled non-incorporable nucleotide analog; step (c) involves detecting the distinguishable label of the labeled non-incorporable nucleotide analog of the stabilized ternary complex, thereby identifying the next correct nucleotide within the primed template nucleic acid molecule; the first reagent further includes a divalent catalytic metal ion; and the distinguishable label of each of the at least one labeled non-incorporable nucleotide analogs includes a distinguishable fluorescent label that is not an intercalating dye that changes fluorescence after contacting DNA.

More preferably, neither the reversible terminator nucleotide nor the at least one polymerase includes an energy transfer partner required for detecting the distinguishable fluorescent label in step (c).

More preferably, the at least one labeled non-incorporable nucleotide analog includes four labeled non-incorporable nucleotide analogs.

According to another generally preferred embodiment, each of the at least one labeled nucleotide analog in step (b) is at least one labeled non-incorporable nucleotide analog; step (c) involves detecting the distinguishable label of the labeled non-incorporable nucleotide analog of the stabilized ternary complex, thereby identifying the next correct nucleotide within the primed template nucleic acid molecule; the first reagent further includes a divalent catalytic metal ion; and the at least one labeled non-incorporable nucleotide analog includes four labeled non-incorporable nucleotide analogs.

More preferably, the distinguishable label of each of the four labeled non-incorporable nucleotide analogs includes a distinguishable fluorescent moiety.

More preferably, each of the four labeled non-incorporable nucleotide analogs is present at a concentration in the range of from 10 nM to 200 nM.

Alternatively, when each of the at least one labeled nucleotide analog in step (b) is at least one labeled non-incorporable nucleotide analog; when step (c) involves detecting the distinguishable label of the labeled non-incorporable nucleotide analog of the stabilized ternary complex, thereby identifying the next correct nucleotide within the primed template nucleic acid molecule; when the first reagent further includes a divalent catalytic metal ion; when the at least one labeled non-incorporable nucleotide analog includes four labeled non-incorporable nucleotide analogs; and when the distinguishable label of each of the four labeled non-incorporable nucleotide analogs includes a distinguishable fluorescent moiety; each of the distinguishable fluorescent moieties can be covalently attached by a linker at position 5 of the nitrogenous base for pyrimidine nucleotide analogs, or at position 7 of the nitrogenous base for purine nucleotide analogs.

More preferably, each of the four labeled non-incorporable nucleotide analogs is present at a concentration in the range of from 10 nM to 200 nM.

Alternatively, when each of the at least one labeled nucleotide analogs in step (b) is at least one labeled non-incorporable nucleotide analog, and when step (c) involves detecting the distinguishable label of the labeled non-incorporable nucleotide analog of the stabilized ternary complex, thereby identifying the next correct nucleotide within the primed template nucleic acid molecule, the at least one labeled non-incorporable nucleotide analog can include four labeled non-incorporable nucleotide analogs.

According to another generally preferred embodiment, each distinguishable label includes a base-specific fluorescent moiety, and neither the reversible terminator nucleotide nor the at least one polymerase includes an energy transfer partner required for detecting the base-specific fluorescent moiety of the distinguishable label in step (c).

More preferably, the base-specific fluorescent moiety does not include an intercalating dye that changes fluorescence after contacting DNA.

According to another generally preferred embodiment, the distinguishable label of the labeled nucleotide analog present in the stabilized ternary complex includes a fluorescent label, and the fluorescent label is not an intercalating dye that changes fluorescence after contacting DNA.

More preferably, the fluorescent label is covalently attached to labeled nucleotide analog by a linker at a position on the nitrogenous base. Optionally, one or more labeled nucleotide analogs are attached to a label via a linker shown in Formula (1a), (1b), (1c), (1d), (2a), (2b), (2c), (2d), (3a), (3b), (3c) or (3d). Optionally, one or more labeled nucleotide analogs are attached to a label via a linker shown in FIG. 2.

More preferably, the linker is attached at position 5 of the nitrogenous base for pyrimidines, or at position 7 of the nitrogenous base for purines.

According to another generally preferred embodiment, the at least one labeled nucleotide analog includes four labeled nucleotide analogs.

According to another generally preferred embodiment, the first reagent further includes a divalent catalytic metal ion.

More preferably, the first reagent does not include a non-catalytic metal ion that inhibits polymerization.

More preferably, the at least one labeled nucleotide analog includes four labeled nucleotide analogs.

More preferably, the distinguishable label of each of the four labeled nucleotide analogs includes a distinguishable fluorescent moiety covalently attached at a position on the nitrogenous base by a linker.

More preferably, the linker is attached at position 5 of the nitrogenous base for pyrimidines, or at position 7 of the nitrogenous base for purines.

More preferably, each of the four labeled nucleotide analogs is present at a concentration in the range of from 10 nM to 200 nM.

According to another generally preferred embodiment, the first reagent further includes a divalent catalytic metal ion; the first reagent does not include a non-catalytic metal ion that inhibits polymerization; the at least one labeled nucleotide analog includes four labeled nucleotide analogs; the distinguishable label of each of the four labeled nucleotide analogs includes a distinguishable fluorescent moiety covalently attached at a position on the nitrogenous base by a linker; and each of the four labeled nucleotide analogs is present at a concentration in the range of from 10 nM to 200 nM.

According to another generally preferred embodiment, wherein the first reagent does not include a non-catalytic metal ion that inhibits polymerization.

According to another generally preferred embodiment, wherein each of the at least one labeled nucleotide analogs of the first reagent is present at a concentration in the range of from 10 nM to 200 nM.

According to another generally preferred embodiment, wherein neither the reversible terminator nucleotide nor the polymerase includes an energy transfer partner required for detecting the distinguishable label in step (c).

EXAMPLES

Those having an ordinary level of skill in the art, after considering and understanding the present disclosure, will appreciate that there are many ways in which the disclosed technique can be practiced. For example, the types of detectable labels used on the nucleotides (e.g., non-incorporable nucleotides) can be varied with good results. Alternative detectable labels include, but are not limited to: fluorescent labels, gold particles, Raman labels, etc. The nature of the non-incorporable nucleotide and reversible terminator nucleotide can be varied with good results. Reversible terminator nucleotides may harbor reversible terminator moieties on any of: the base; the sugar; or the phosphate components of the nucleotides.

The following Example demonstrated how a combined blocking-and-examination step can be used. Here a single reversible terminator nucleotide incorporated into the primer strand of a primed template nucleic acid, and dynamic formation of a ternary complex that included a polymerase, a detectably labeled nucleotide, and the blocked primed template nucleic acid molecule was detected. Only cognate nucleotide participated in ternary complex formation. Accordingly, detecting and identifying the labeled nucleotide within the ternary complex indicated identity of the cognate nucleotide. Thus, a primed template nucleic acid immobilized within a flow cell or other solid support can be contacted with a reagent including a polymerase, reversible terminator nucleotides, and one or more distinguishably labeled nucleotides (e.g., the base of each different nucleotide being associated with a corresponding distinguishable label) to carry out incorporation of a reversible terminator, and examination at the N+2 position of the primer without an intervening wash step. While the procedure illustrated below was carried out using an incorporable labeled nucleotide analog, similar results can be achieved using labeled non-incorporable nucleotides. Still further, the procedure may be simplified by using only four reversibly terminated nucleotides (e.g., where the label is optionally either omitted from, or included in the blocked primed template nucleic acid reaction product).

Example 1 illustrates incorporation of a reversible terminator nucleotide, and detection of a labeled nucleotide dynamically bound to the resulting blocked primed template nucleic acid (i.e., as a component of a ternary complex) in the same reaction mixture. In this procedure, the reversible terminator moiety and the detectable label moiety were located on different nucleotide molecules. In an alternative procedure, the two moieties are on the same nucleotide analog.

Example 1

Incorporation of a Reversible Terminator Nucleotide and Detection of Labeled Nucleotide Associating with a Blocked Primed Template Nucleic Acid Molecule in the Same Reaction Mixture Synthetic template and 5'-biotinylated primer strands were synthesized according to standard procedures, and hybridized to create a primed template nucleic acid molecule having a 3'-end available for polymerization. The next three template-specific bases to be incorporated into the primer strand (i.e., positions N+1, N+2, and N+3) were ATC. Streptavidin-coated magnetic beads were functionalized with 1 mM NHS-PEG4-TCO in phosphate buffered saline (PBS) that had been made 10% DMSO at room temperature for 45 minutes. Processed beads were then decorated with the biotinylated primed template nucleic acid molecule. The beads were next flowed over an aminosilane flow cell surface that had been functionalized with tetrazine. The reaction mixture was incubated for one hour to covalently attach the decorated beads to the surface within the flow cell.

Incorporation of reversible terminator nucleotide (at the N+1 primer position) and examination for labeled nucleotide binding (at the N+2 primer position) were carried out using three reagent solutions. The "regeneration solution" was a pH-buffered mixture that included 50 mM KCl, 10 mM $(NH_4)_2SO_4$, and 0.1% Triton X-100. The "examination/incorporation solution" was a pH-buffered mixture that included 50 mM KCl, 10 mM $(NH_4)_2SO_4$, 0.1% Triton X-100, 2 mM $MgCl_2$, 200 nM of an unlabeled reversibly terminated nucleotide analog of dATP, 100 nM of Cy-5-labeled nucleotide (i.e., a nucleotide analog of either dATP, dGTP, dCTP, or dTTP), and 10 U/ml Therminator polymerase. The reversible terminator nucleotide used in this illustrative procedure included a 3'-$ONH_2$ reversible terminator moiety that was removable by contact with an acetate-buffered solution containing $NaNO_2$. A description of this reversible terminator nucleotide can be found in U.S. Pat. No. 7,544,794, the disclosure of which is incorporated by reference. The "stripping solution" was a pH-buffered mixture that included 1 M NaCl, 0.1% Tween-20, 0.02% SDS, 2 mM EDTA, and 2 mM NTA. The following volumes of the preceding solutions were flowed over the flow cell in a cycling manner at 45° C.: 200 µl stripping solution; 200 µl regeneration solution; and 100 µl of examination/incorporation solution. Fluorescence emission from the Cy-5 moiety was monitored as an indicator of cognate nucleotide participating in formation of ternary complexes. Independent control reactions were performed by examining binding of the fluorescently labeled nucleotides (e.g., in ternary complexes), one at a time in the presence of unlabeled reversible terminator nucleotide, to: (a) confirm incorporation of the reversible terminator nucleotide to create the blocked primed template nucleic acid molecule; and (b) verify specificity of the dynamic binding to that blocked primed template nucleic acid. Here, washes with the stripping and regeneration solutions preceded each binding-and-examination reaction to eliminate possible cross-labeling. Three representative beads were processed to measure signal intensities through the reagent cycling program.

Results from the procedure indicated that, in a single reaction mixture, a reversible terminator nucleotide incorporated at the N+1 position (i.e., the first nucleotide position downstream of the starting 3'-end of the primer), and that a reversible binding interaction of the labeled cognate nucleotide was detected at the N+2 position (i.e., the second nucleotide position downstream of the starting 3'-end of the primer). FIG. 1 shows measured fluorescent signals specific for different nucleotides labeled with Cy-5. As expected, the reversibly terminated dATP nucleotide analog incorporated to create a blocked primed template nucleic acid molecule, and a strong binding signal was detected for the labeled dTTP nucleotide (i.e., the cognate nucleotide for the N+2 position). Binding of the labeled nucleotide was non-covalent, because the fluorescent signal was removed by washing with stripping and regeneration solutions. Control binding reactions carried out using labeled nucleotide analogs of dCTP, dATP, and dGTP all yielded low signals that did not indicate specific binding. This demonstrated that labeled non-cognate nucleotides did not substantially interact with polymerase and the blocked primed template nucleic acid, also as expected. Thus, the procedure employing a single step for incorporating reversible terminator nucleotide and detecting a non-incorporating complex containing labeled nucleotide clearly identified the cognate nucleotide for a position within the primed template nucleic acid molecule. Treating the blocked primed template nucleic acid molecule to remove the attached reversible terminator moiety leaves a 3'-end available for subsequent polymerization, so that the blocking-and-examination step can be repeated to identify the cognate nucleotide for the N+3 and downstream positions.

Following is another illustration of cognate nucleotide detection using nucleotide analogs, rather than polymerization-inhibitory metal ions, to stabilize ternary complexes. Optionally, one or more catalytic metal ions (e.g., $Mg^{2+}$, $Mn^{2+}$, etc.) can be included in the reaction mixture of the examination step used for detecting signals indicating ternary complex formation. Unlike procedures requiring intercalating dye-labeled nucleotides to indicate formation of ternary complexes, the technique described below preferably does not employ intercalating dyes or labels. Instead, non-intercalating fluorescent moieties that do not bind to DNA can be employed, and are preferred. Optionally, the label is covalently attached to the base moiety of the labeled nucleotide. Of course, when four distinguishably labeled nucleotides are used together in a single reaction mixture, different labels (e.g., 2, 3, or 4 different labels) can be attached to the base moieties of the different nucleotides (i.e., nucleotide analogs). In this way, the distinguishable label indicates identity of the base moiety in the cognate nucleotide.

As is the case with the embodiments described above, stabilization of ternary complexes including the labeled nucleotide that indicated cognate nucleotide identity resulted from a reversible terminator nucleotide at the 3' end of a primer, and need not involve other mechanisms. For example, it is unnecessary to further employ non-catalytic metal ions at a concentration sufficiently high that polymerase activity is inhibited. Likewise, it is unnecessary to further rely on concentrations of catalytic metal ions that inhibit polymerase activity. It is unnecessary to employ any modified polymerase having reduced ability to promote incorporation of cognate nucleotide into a primer strand by phosphodiester bond formation. While certain other embodiments described herein benefited from the use of labeled non-incorporable nucleotides, the use of these nucleotides is optional in the procedure of the following Example. Indeed, the labeled nucleotides employed below were incorporable nucleotides. Thus, the ternary complex stabilization mechanism can be quite simple while still supporting successful nucleotide identification.

The following procedure demonstrated the use of distinguishably labeled incorporable nucleotides in a Sequencing By Binding™ protocol. Labeled nucleotides harbored fluorescent moieties covalently attached at base position 5 for pyrimidine analogs, or at base position 7 for purine analogs (see FIG. 2). While this illustration employed single nucleotides in the processing steps, alternative use of four different nucleotide analogs, each with a distinguishable label, permits simultaneous examination of four nucleotide analogs. As well, while the procedure is presented with reference to one type of polymerase (i.e., Therminator™ DNA polymerase from New England BioLabs), excellent results also have been achieved using Polλ, truncated Polλ, and Phi29 polymerases. None of the polymerases required an exogenous label for cognate nucleotide detection, and no FRET relationship with the fluorescent label of the nucleotide was needed to identify cognate nucleotides.

Example 2 illustrates detection of cognate nucleotides using labeled incorporable nucleotide analogs. Ternary complexes were stabilized by the use of reversible terminator nucleotides that precluded incorporation. In this instance, blocked primed template nucleic acids prepared in a first reaction mixture were contacted with labeled nucleotides in a second reaction mixture. Detection of ternary complex formation took place in the second reaction mixture. The procedure was performed in the presence of catalytic metal ions.

Example 2

Method of Identifying Cognate Nucleotide in a Stabilized Ternary Complex Formed in the Presence of a Catalytic Metal Ion A flow cell containing nucleic acid features was prepared according to standard methods. Streptavidin-coated microbeads were contacted with a solution that included primed template nucleic acid, where the template strand was biotinylated at its 5'-end. Beads having immobilized primed template nucleic acid subsequently were affixed to the interior surface of a flow cell by standard chemistry that will be familiar to those having an ordinary level of skill in the art. Two different populations of beads were used in the procedure to demonstrate multiplex processing. The next correct nucleotide to be incorporated for the first bead type ("Bead 1") was dTTP (or dUTP), and the next correct nucleotide to be incorporated for the second bead type ("Bead 2") was dGTP. Reference images were taken in the 647 nm channel to enable background fluorescence subtraction from signal observed upon later ternary complex formation. The result was a population of unlabeled beads ready for incorporating reversible terminator nucleotides.

Blocked primed template nucleic acids were prepared on the immobilized beads as follows. The flow cell was first flushed with a pre-incorporation solution containing 20 mM AMPSO buffer (pH 9.5), 50 mM KCl, 10 mM $(NH_4)_2SO_4$, and 0.1% TritonX-100. Next, an incorporation solution was flowed through the flow cell to incorporate a single reversible terminator nucleotide into each primer strand. The incorporation solution included 20 mM AMPSO buffer (pH 9.5), 50 mM KCl, 10 mM $(NH_4)_2SO_4$, 0.1% TritonX-100, 10 U/ml Therminator™ DNA polymerase (New England BioLabs; MA), 5 mM $MgCl_2$, and 25 µM of each of four dNTP analogs included an aminooxy (3'-$ONH_2$) reversible terminator moiety. The flow cell was then washed with the pre-incorporation buffer to prepare the beads for examination. At this point the different features respectively included different blocked primed template nucleic acids.

Immobilized features having blocked primed template nucleic acids were next contacted with reagent solutions to investigate reversible formation (i.e., dynamic equilibrium, without incorporation) of ternary complexes containing different labeled nucleotides. Reagent solutions that were used each included: a polymerase; one of four fluorescently labeled nucleotide analogs that were incorporable and not reversibly terminated (see FIG. 2); and a catalytic metal ion. Despite the structure of the labeled nucleotides, there was no incorporation due to the presence of the reversible terminator moiety on the blocked primer. This was confirmed by the ability to remove substantially all fluorescent signal from ternary complexes using a stripping wash solution, as indicated below. Labeled nucleotides contacted the blocked primed template nucleic acid one at a time. Reagent solutions used for detection of ternary complex formation included 30 mM HEPES (pH 7.5), 100 mM NaCl, 20 mM $MgCl_2$, 100 µg/mL BSA, 0.01% Tween-20, 1% Tween-80, 10% DMSO, 1 mM TCEP, 100 nM Therminator™ DNA polymerase, and 100 nM of one of the four different Cy-5 labeled dNTP analogs. In these procedures, the dUTP analog was used as an alternative to the dTTP analog, since nucleotide binding specificities were substantially equivalent. At the end of each labeled nucleotide examination cycle, the flow cell was washed to strip away polymerase and labeled nucleotide from ternary complexes before initiating the next round of labeled nucleotide examination. The stripping wash buffer was the same as the reagent solutions used for detection, but included 5% Tween-80, 500 mM NaCl, and 2 mM EDTA, and did not include $Mg^{2+}$ ion, DNA polymerase, or any labeled dNTPs. Fluorescence measurements of the dynamic equilibrium association of labeled nucleotide with the beads were detected and recorded using standard fluorometry procedures that will be familiar to those having an ordinary level of skill in the art. Fluorescence data for images of representative features was processed to determine the extent of interaction of different labeled nucleotides with the different bead types. This procedure was repeated to detect formation of ternary complexes containing labeled dGTP.

Figure 3:
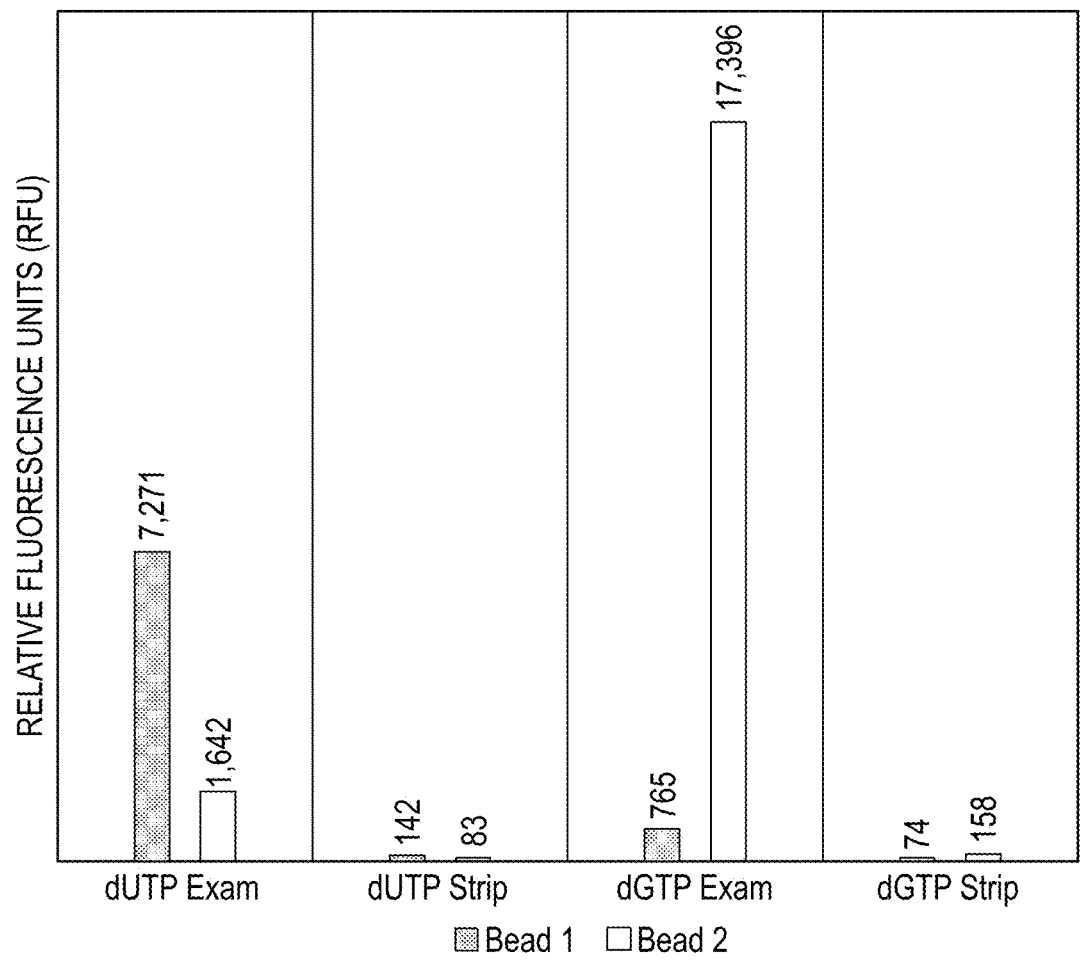
FIG. 3 is a bar graph showing results for detection of ternary complexes containing base-labeled nucleotide analogs. Magnitudes of fluorescent signals (vertical axis) for each of two different bead types (i.e., 1 and 2) are shown for different examination conditions. Results obtained for Bead 1 are indicated using stippled bars. Results obtained for Bead 2 are indicated using open bars. Numbers above each bar indicate relative fluorescence units.

The results presented in FIG. 3 confirmed that cognate nucleotides were detected for each of the two bead types with very good signal-to-noise ratios. As indicated, the dUTP analog gave a strong signal for Bead 1, and a weak signal for Bead 2, as expected. Substantially all the fluorescent label was removed from the beads by washing with the stripping buffer, indicating that the label was non-covalently associated with both features. Contacting the beads with the labeled dGTP analog gave a strong signal for Bead 2, and a weak signal for Bead 1, again as expected. Again, substantially all the fluorescent label was removed from the beads by washing with the stripping buffer. Notably, all fluorescence readings were made in the presence of labeled nucleotide analog that was free in solution (i.e., non-complexed). Stated differently, the same reaction mixture used for contacting labeled nucleotide and blocked primed template nucleic acid also was used for detecting the dynamic interaction, without any intervening wash step. It was not necessary to remove non-complexed labeled nucleotide from the flow cell system to obtain good results. This aspect of the disclosed method can be exploited for rapid Sequencing By Binding™ procedure in a cyclical fashion.

The following Examples illustrate the simultaneous reduction of undesirable background signal (e.g., fluorescent background signal) and stabilization of ternary complexes immobilized to a solid support in a Sequencing By Binding™ workflow. The technique was shown to improve results obtained in Sequencing By Binding™ assays employing either detectably labeled nucleotides or detectably labeled polymerases. More generally, the method can be used to enhance detection of specific interactions between different components of a multi-component complex, with application to systems employing one or more detectably labeled components. Use of the technique obviates potential problems arising from reduced signal-to-background ratios due to high levels of non-complexed reagents remaining in the solution phase, where the reduced ratios can mask proper cognate nucleotide identification.

It was discovered during development of the present technique that the benefit of using high concentrations of detectably labeled components to drive formation of specific complexes was offset by high background signals resulting from non-complexed labeled reagents remaining in solution. The fact that nucleotide concentrations typically far exceed polymerase concentrations in Sequencing By Binding™ assays makes certain procedures employing labeled nucleotides particularly susceptible to this issue. Moreover, the dynamic nature of the ternary complex (e.g., where the complex is in a reversible state of formation and dissociation) complicates the situation when conventional reagent wash steps are performed to remove non-complexed reagents from the system. This is because reversible complexes can dissociate when components needed for maintenance (e.g., nucleotide and/or polymerase) are removed from the system. When the rate of dissociation is significant, the complex can be dissociated completely before it can be detected.

Accordingly, two technical issues impact clear detection of multi-component complexes when using components that include detectable labels. First, signals originating from the labeled component can obscure detection of specific complexes due to high background signals (e.g., fluorescent signals arising from non-complexed fluorescent nucleotides or fluorescent polymerases). Second, washing to remove one or more of the labeled components from the system can promote dissolution of complexes that are to be detected. Both issues were addressed by simultaneously stabilizing ternary complexes and removing non-complexed reagents (e.g., excess labeled polymerase or nucleotide remaining in solution) from the binding reaction mixture. Optionally, this can be accomplished by immobilizing the ternary complex to a solid support, and then flushing the system using a stabilizing fluid in which the labeled reagent(s) are substantially insoluble. Complex-specific signals can then be detected, monitored, and/or quantified during this imaging wash step before any other fluorescent reagent is introduced into the system (e.g., by flowing through a flow cell). By this approach, components of preformed ternary complexes cannot substantially partition into the stabilizing fluid used in the flush step, and so association of the different components can be maintained. While not wishing to be limited by any particular theory of operation, one possibility is that ternary complexes can be precipitated in place with the same result as though integrity of the complex was maintained. Indeed, signal associated with immobilized complexes can be highly stable and can remain detectable over the course of 10 seconds, 30 seconds, and even at least 10 minutes. These stability ranges can easily exceed the time needed to make a measurement that would detect and/or identify the labeled component of the complex.

The following Examples show how an imaging wash with a stabilizing fluid could be used to remove non-complexed constituents of ternary complexes, while simultaneously stabilizing immobilized ternary complexes. Detectability of the complexes over extended periods was improved as a consequence of implementing the imaging wash. Moreover, better-quality sequencing results were obtained in Sequencing By Binding™ procedures when an imaging wash employing a stabilizing fluid was included in the workflow.

Example 3 illustrates the use of an imaging wash with a stabilizing fluid after a ternary complex formation step that employed fluorescently labeled nucleotides. Labeled nucleotide analogs and unlabeled polymerase were used to form ternary complexes with primed template nucleic acids immobilized to beads in a flow cell. Nucleotide analogs included a fluorescent moiety that did not substantially change optical properties (e.g., excitation or emission) in the presence of polymerase and/or primed template nucleic acid. Results confirmed that, unlike an aqueous wash step that did not stabilize complexes, the stabilizing fluid substantially preserved integrity of ternary complexes over extended periods. The stabilizing fluid in this illustration was a non-aqueous alkane hydrocarbon that was not miscible with water. Labeled ternary complexes were detected during the imaging wash step.

Example 3

Imaging Wash Reduces Background Signal and Stabilizes Ternary Complexes: Labeled Nucleotide Platform Flow cells containing immobilized microbeads harboring single-stranded template nucleic acids hybridized to sequencing primers were obtained by conventional laboratory procedures familiar to those having an ordinary level of skill in the art. Four populations of beads were included in the procedure, with each bead type harboring a different primed template nucleic acid. The flow cell was first equilibrated with a pre-incorporation solution that included AMPSO buffer (about pH 9.0), 50 mM KCl, 10 mM $(NH_4)_2SO_4$, 0.1% Triton X-100 (trademark of Dow Chemical Company) nonionic detergent, and 0.1% hydroxylamine to maintain integrity of reversible terminator nucleotides used in a subsequent step. Next, the flow cell was equilibrated with a solution that included four reversible terminator nucleotides, and that consisted of the pre-incorporation solution supplemented with 10 U/ml Therminator DNA polymerase (New England BioLabs), aminoxy (i.e., 3'-$ONH_2$) reversible terminator nucleotides (dATP, dGTP, dCTP and dTTP), and 5 mM $MgCl_2$ to incorporate a single reversible terminator nucleotide at the 3'-end of each different primed template nucleic acid. This blocked the primers with a reversible terminator nucleotide that precluded subsequent nucleotide incorporation. The flow cell was then equilibrated with the pre-incorporation solution to remove residual components of the incorporation reaction. Next, an examination solution that included a fluorescent dGTP nucleotide analog was flowed into the flow cell and allowed to stand for a period of 30 seconds, during which time ternary complexes formed on appropriate beads (i.e., the beads for which dGTP was the next correct nucleotide). The examination solution consisted of the pre-incorporation solution supplemented with 400 nM Cy5 base-labeled dGTP nucleotide analog, 10 U/ml Therminator polymerase, and an optional source of catalytic metal ion (i.e., 10 mM $MgCl_2$). Despite the presence of the catalytic metal ion, the nucleotide analog could not incorporate into the 3'-blocked primer. Examination solution containing the polymerase and labeled nucleotide was next replaced by flowing into the flow cell imaging wash reagents that were either: (a) the pre-incorporation solution that did not contain either the polymerase or nucleotide; or (b) 100% decane. Here the pre-incorporation solution represented an aqueous solution in which polymerase and nucleotide were soluble, while decane represented a non-aqueous reagent in which polymerase and nucleotide were not soluble. Once flowed into the flow cell, the wash reagents remained in contact with the immobilized beads without further flow. Imaging of beads under each condition was performed every second for a period of one minute, where exposures were one second each. Three regions of interest corresponding to different beads were selected, and quantified images of the beads as a function of time were background subtracted (i.e., signal from beads that remained non-fluorescent were used for the subtraction). Notably, because the light source used for exciting the nucleotide-linked fluorophore was continuously on during the procedure, photobleaching (i.e., emission signal decreases with increasing time of exposure to the excitation wavelength) of the fluorescent dye moiety was to be expected.

Figure 4:
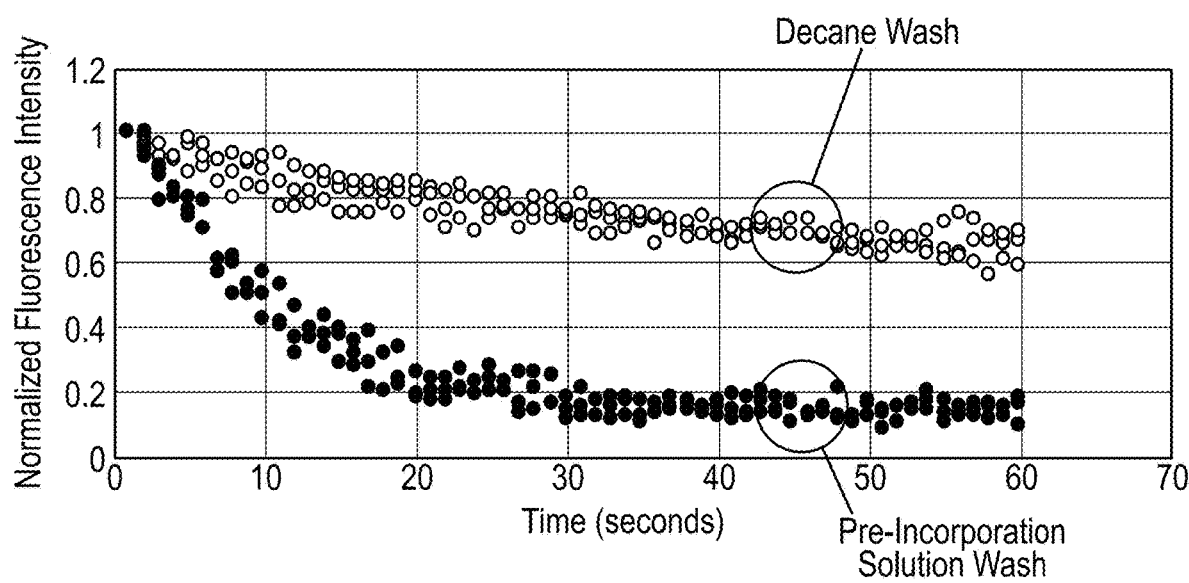
FIG. 4 is a scatter plot showing time (in seconds) on the horizontal axis and normalized fluorescent signal intensities on the vertical axis for two wash conditions following formation of ternary complexes. Trials were conducted in replicates of three for each wash condition.

Results presented in FIG. 4 illustrated dramatic differences in the stabilities of ternary complexes incubated in the different imaging wash reagents. Data plotted in the figure was normalized to the first image in each series. Decane-stabilized ternary complexes exhibited about 20% reduced signal after 20 seconds. In comparison, ternary complexes incubated in the pre-incorporation solution lost about 80% of the fluorescent signal after the same period. Significantly, signal loss in the trial carried out using decane as the imaging wash reagent was predominantly an artifact of photobleaching the Cy5 fluorophore rather than decomposition of the ternary complex. Extended photoirradiation was only used in the procedure to capture the time course data, and alternatively imaging the decane trial only at the start and finish of the one-minute incubation period would show substantially less signal loss. Conversely, the rapid signal loss observed for the trial employing the aqueous buffer in which polymerase and nucleotide were soluble was due to instability and dissociation or decomposition of ternary complexes.

Example 4 illustrates how the model stabilizing fluid described in Example 3 could be used to improve detection of binding interactions. The system used in this demonstration employed a Sequencing By Binding™ protocol to generate nucleic acid sequencing data. The stabilizing fluid simultaneously reduced background fluorescence attributed to non-complexed fluorescent nucleotide analogs, and stabilized ternary complexes that included a primed template nucleic acid, a polymerase, and a fluorescently labeled cognate nucleotide analog. Non-specific fluorescent background signal was reduced by removing non-complexed labeled binding components from a flow cell system. The procedure employed fluorescently labeled nucleotide analogs and unlabeled polymerase to form ternary complexes with primed template nucleic acids immobilized to beads contained within a flow cell. Components of the ternary complexes interacted in a reversible fashion to form ternary complexes, where the complexes were in dynamic equilibrium with their chemical environments. The detectable label attached to the nucleotide analogs included a fluorescent moiety that did not substantially change optical properties (e.g., excitation or emission) in the presence of polymerase and/or primed template nucleic acid. Energy transfer to or from another chemical moiety was not required for success of the procedure. Results presented below confirmed that the stabilizing fluid substantially preserved the integrity of ternary complexes over the course of at least 30 seconds. Similar procedures showed that ternary complexes were maintained stable for at least 5 minutes, and for at least 10 minutes. Correct base calls were made using only fluorescent imaging data acquired during the imaging wash step (i.e., with ternary complexes in contact with the stabilizing fluid, and after non-complexed labeled nucleotides were removed from the flow cell). While processing of ternary complexes prepared from synthetic oligonucleotides immobilized to beads is described here, similar procedures can be carried out using template strands synthesized in situ within a flow cell (e.g., using a rolling circle amplification protocol). Again, an organic oil (i.e., a purified higher alkane) served as the stabilizing fluid in this Example. Good results also have been achieved using mineral oils, paraffin oils, inorganic silicone oils, perfluorocarbons, ethanol and aqueous ethanol solutions, isopropanol and aqueous isopropanol solutions, 2-butanol, air, etc. Neither the nucleotide nor the polymerase used for assembling ternary complexes could substantially dissolve or partition into any of these reagents.

Example 4

Sequencing Procedure Employing a Stabilizing Fluid that Simultaneously Stabilized Ternary Complexes and Reduced Background Signal Beads harboring synthetic oligonucleotides hybridized to sequencing primers (i.e., primed template nucleic acid molecules) were used for conducting Sequencing By Binding™ reactions with a fluorescently labeled nucleotide analog, where the examination step included an imaging wash to remove or displace from a flow cell any non-complexed polymerase and nucleotide prior to fluorescent image capture. Imaging washes used either a stabilizing fluid (e.g., n-decane) or the aqueous pre-incorporation solution of Example 3. Streptavidin-coated beads bound to an inner surface of a flow cell harbored biotinylated template DNA that was hybridized to a complementary oligonucleotide primer. Enzymatic incorporation of a cognate nucleotide with a 3'-$ONH_2$ reversible terminator moiety into the primer strand was carried out essentially as described under Example 3 to result in a reversibly terminated (i.e., "blocked") primed template nucleic acid molecule. Examination reagent solutions used in the procedure included pre-incorporation solution supplemented with either 400 nM Cy5 base-labeled dATP, 200 nM Cy5 base-labeled dGTP, 400 nM Cy5 base-labeled dCTP, or 800 nM Cy5 base-labeled dTTP. Four separate examination buffers that included a polymerase and a single nucleotide labeled on its base with a Cy5 fluorescent moiety (i.e., Cy5-dATP, Cy5-dGTP, Cy5-dCTP, or Cy5-dTTP) were introduced into the flow cell one after the other to permit formation of ternary complexes with the reversibly terminated primed template nucleic acid when the nucleotide was the next correct nucleotide. Each ternary complex included an immobilized blocked primed template nucleic acid molecule, a polymerase, and a fluorescently labeled cognate nucleotide. Polymerase used in the procedure was the native Therminator DNA polymerase (New England BioLabs) that retained catalytic activity. Following introduction of each different examination buffer into the flow cell to permit formation of ternary complexes, the flow cell was flushed completely with either decane or the aqueous pre-incorporation of Example 3 that did not contain either polymerase or nucleotide. This removed non-complexed fluorescent nucleotide analogs remaining free in solution within the flow cell. An imaging step measured fluorescent signal associated with the beads during the wash step, and before any other reagent was flowed into the flow cell. After investigating ternary complex formation using each of four different nucleotides, the polymerase and cognate nucleotide were stripped from the blocked primed template nucleic acid by washing the flow cell with an EDTA-containing high-salt (e.g., 1M NaCl) buffer. The blocking group on the primer was then removed using a cleavage or deblocking solution that included sodium acetate buffer and $NaNO_2$. The next cognate nucleotide containing a reversible terminator blocking group was incorporated as described above. This advanced or lengthened the primer by a single nucleotide. Thereafter, binding interaction of the blocked primed template nucleic acid molecule with polymerase and the next test nucleotide was investigated by repeating the procedure and imaging fluorescent signals during the wash steps.

Polymerase used in this procedure did not include any exogenous fluorescent label that was detected to make the cognate nucleotide identification (i.e., polymerase was unlabeled). Interrogation of blocked primed template nucleic acid molecules, including cycles of examination, fluorescent imaging during wash steps, de-blocking, and incorporation of unlabeled reversible terminator nucleotides was repeated for 11 complete cycles to determine the identity or sequence of consecutive cognate nucleotides. Images were captured 10 seconds after flowing decane into the flow cell to replace the solution containing polymerase and nucleotide. Notably, essentially identical procedures that extended the decane exposure time to 5 minutes or 10 minutes gave results substantially identical to the procedure employing the 10 second exposure period. Use of a non-catalytic metal ion that inhibits incorporation alternatively can be used in place of the blocked primed template nucleic acid molecule to stabilize ternary complexes and preclude or prevent polymerase-mediated nucleotide incorporation. An engineered polymerase incapable of catalyzing phosphodiester bond formation also can be used to stabilize ternary complexes and prevent nucleotide incorporation.

Results from these procedures indicated that an imaging wash with a stabilizing fluid reduced fluorescent background while maintaining fluorescent signal specific for ternary complex formation. Signal specific for ternary complexes was not detected for control reactions conducted using the aqueous pre-incorporation solution as the imaging wash. This was because ternary complexes dissociated to the point of being undetectable in the aqueous imaging wash solution before images could be captured. This was especially problematic for the labeled dTTP nucleotide, which seemed to be lost from the ternary complex immediately upon exposure to wash solutions in which the nucleotide was soluble. In contrast, FIG. 5A shows images of a single bead during the imaging wash step performed using decane as the stabilizing fluid. Each row of four images represents a complete cycle of examination with four different fluorescently labeled nucleotides (i.e., in order: Cy5-dATP, Cy5-dGTP, Cy5-dCTP, and Cy5-dTTP). Consecutive rows represent consecutive nucleotide positions being examined, where a reversible terminator moiety was removed and a subsequent reversible terminator nucleotide incorporated to advance the primer by a single nucleotide. Quantitation of the image intensities is graphically presented in FIG. 5B. Correct base calls corresponded to the highest magnitude signal from each set of four nucleotides for each complete examination cycle. Again, all fluorescent readings used to make the cognate nucleotide identification were acquired during the imaging wash steps when the flow cell contained the stabilizing fluid, and when non-complexed nucleotides had been removed from the flow cell.

Following are descriptions showing how air could be used as an alternative stabilizing fluid for flushing or washing immobilized ternary complexes to improve detectability of the complexes. Again, constituents or components of the complexes to be detected did not dissolve or partition into the stabilizing fluid, and so the transient or reversible complexes were maintained in a stable configuration during the imaging wash step.

Example 5 further illustrates how a stabilizing fluid simultaneously reduced non-specific background signal and stabilized ternary complexes in a flow cell system. The procedure employed fluorescently labeled polymerase and native nucleotides to form ternary complexes with primed template nucleic acid molecules. Good results also have been achieved using fluorescently labeled nucleotides and unlabeled polymerase to form the ternary complexes. Primed template nucleic acids included either nucleic acid amplification products immobilized to a surface within a flow cell, or synthetic oligonucleotides that were immobilized to beads contained within flow cells. Air served as the stabilizing fluid in this Example. The excellent discrimination results presented below indicated that correct base calls could be made using only the fluorescent imaging results acquired during the imaging wash step (e.g., after air displaced examination buffer from within a flow cell).

Example 5

Use of a Stabilizing Fluid to Simultaneously Reduce Background Signal and Stabilize Ternary Complexes: Labeled Polymerase Platform Beads harboring synthetic primed template nucleic acid molecules were used for conducting Sequencing By Binding™ reactions with a fluorescently labeled polymerase, where the examination step included either an "air wash" or an aqueous buffer wash to remove non-complexed polymerase and nucleotide prior to fluorescent image capture. Streptavidin-coated beads covalently bound to an inner surface of a flow cell harbored biotinylated template DNA hybridized to a complementary oligonucleotide primer. Enzymatic incorporation into the primer strand of a single nucleotide having a 3'-$ONH_2$ reversible terminator moiety resulted in a reversibly terminated (i.e., "blocked") primed template nucleic acid molecule for use in a subsequent examination step. An examination buffer that included a fluorescently labeled polymerase, a single native test nucleotide, and a non-catalytic metal ion (i.e., $SrCl_2$) was introduced into the flow cell to permit formation of ternary complexes when the nucleotide was the next correct nucleotide. Notably, use of either a blocked primer or a non-catalytic metal ion that inhibits incorporation is sufficient to stabilize ternary complex formation and preclude or prevent polymerase-mediated nucleotide incorporation (i.e., it is unnecessary to include both). Alternatively, an engineered polymerase incapable of catalyzing magnesium-dependent phosphodiester bond formation can instead be used to stabilize ternary complexes and prevent nucleotide incorporation. An exemplary crippled DNA polymerase useful in this regard is described in commonly assigned U.S. patent application Ser. No. 15/581,822, the disclosure of which is incorporated by reference in its entirety. In the present procedure, however, the polymerase was a Bsu-derived polymerase that retained catalytic activity, and that was covalently attached to a Cy5 fluorophore. Next, the flow cell was flushed completely with either: (a) air; or (b) examination buffer that omitted polymerase and nucleotide. An imaging step then captured a digital image of the flow cell containing beads under each condition. Quantitative data from the imaging steps, which were collected during the wash steps and before any other reagent contacted the immobilized beads, was used to assess the efficiency of removing fluorescent reagent that remained free in solution and not part of an immobilized ternary complex. Polymerase and nucleotide complexed with the blocked primed template nucleic acid molecule were removed by washing the flow cell with an EDTA-containing, high-salt (e.g., 1M NaCl) buffer. Thereafter, the binding interaction of the blocked primed template nucleic acid molecule with polymerase and the next test nucleotide was investigated by repeating the procedure and imaging fluorescent signals during the wash steps. After investigating ternary complex formation using each of four different nucleotides, the blocking group on the primer was removed by chemical cleavage, and the next cognate nucleotide containing a reversible terminator blocking group was incorporated. This advanced or lengthened the primer by a single nucleotide. Reversible terminator nucleotides used in this procedure did not include exogenous fluorescent labels that were detected (i.e., reversible terminator nucleotides were unlabeled). Interrogation of blocked primed template nucleic acid molecules, including cycles of nucleotide examination, fluorescent imaging during wash steps, de-blocking to remove reversible terminator moieties, and incorporation of unlabeled reversible terminator nucleotides, was repeated for 40 cycles.

In a related procedure, stability of ternary complexes during an air wash within a flow cell was assessed using either beads displaying synthetic oligonucleotides that were hybridized to sequencing primers, or alternatively using DNA templates synthesized in situ by Rolling Circle Amplification and then hybridized to a sequencing primer. Immobilized beads and immobilized amplification products located at fixed positions (but not necessarily pre-determined positions) within the flow cell are sometimes referred to herein as "features." Examination buffer that included fluorescently labeled polymerase, a single nucleotide (i.e., either dATP or dCTP), and a non-catalytic metal ion (i.e., $SrCl_2$) was flowed into a flow cell to permit ternary complex formation when the nucleotide being examined was the next correct nucleotide. In this procedure, dCTP was the next correct nucleotide, while dATP served as a model incorrect nucleotide. After flushing the flow cell with air to remove the liquid contents, there was a delay of 0, 20, 40, or 60 seconds before fluorescent imaging was performed. To avoid photobleaching effects, different trials were conducted for samples subjected to the different delay times. Again, digital images of the flow cells were captured while the flow cell was filled with air that displaced the examination buffer (i.e., during the air wash), and before any subsequent reagent was introduced into the flow cell. Fluorescent signal specifically associated with different features (i.e., either beads or clusters representing individual amplification products) were determined by subtracting measured fluorescent background signal from raw fluorescent signals associated with the different features. Background signal was determined as the fluorescent signal that was not associated with immobilized beads (sometimes referred to as "off signal").

Figure 6A:
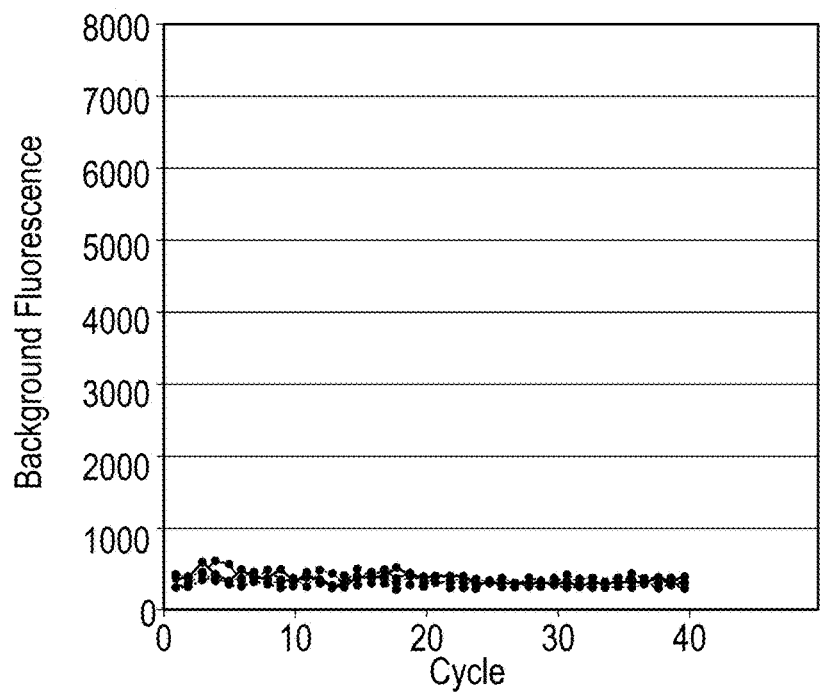
FIGS. 6A-6B show results from replicate fluorescent background determinations using different wash reagents.
Figure 6B:
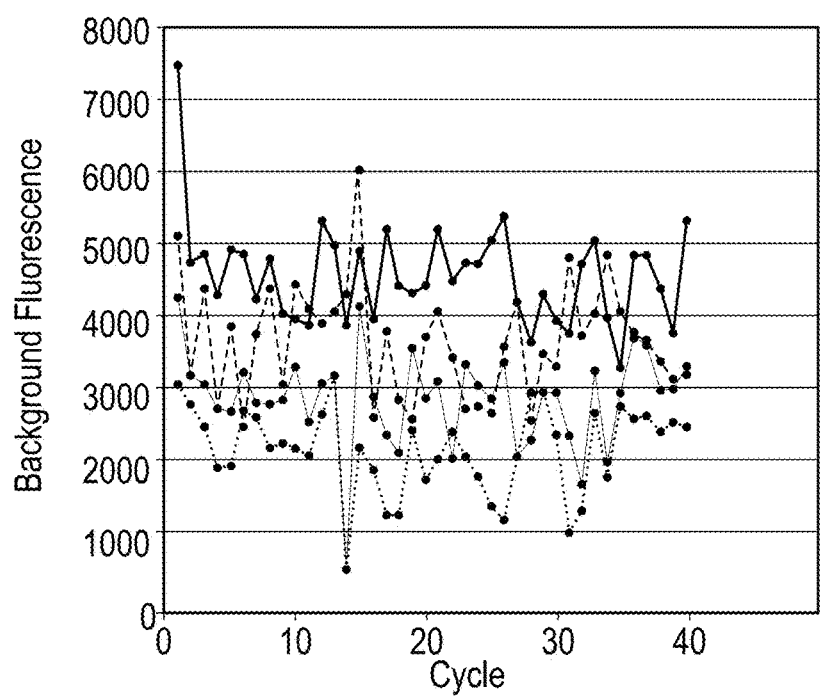
Figure 7A:
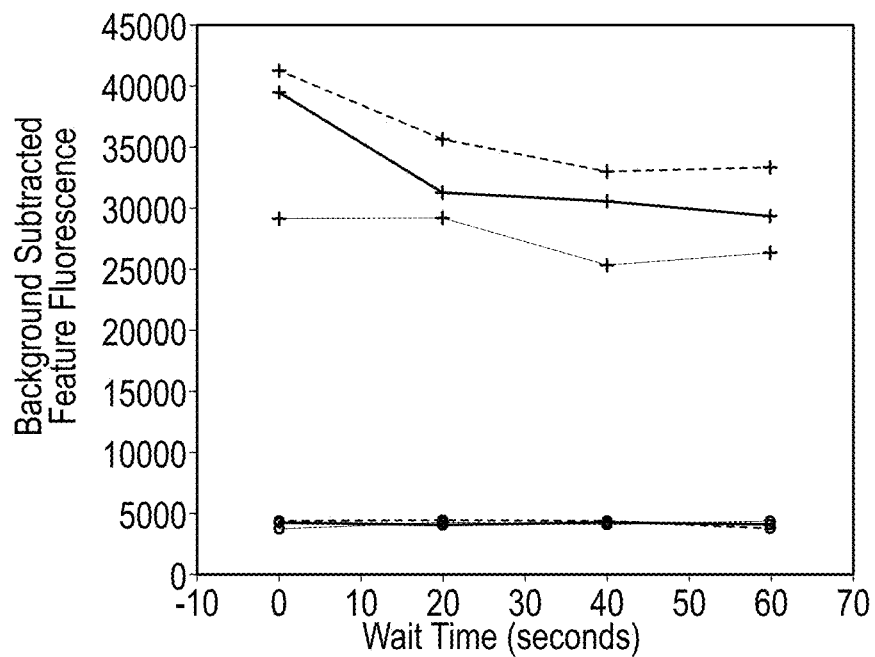
FIGS. 7A-7B show results from three replicates of background-subtracted fluorescence readings measured for nucleic acid features contacted with either cognate or non-cognate labeled nucleotide, where fluorescence data was gathered after an air flow displaced examination buffer that included nucleotide and labeled polymerase. Nucleic acid features in the procedure were either beads harboring synthetic oligonucleotides hybridized to primers (FIG. 7A), or RCA amplification products synthesized in situ and then hybridized to sequencing primers (FIG. 7B). In each of the two plots, the upper sets of three replicates correspond to results obtained using cognate nucleotides (+), while the lower sets of three replicates correspond to results obtained using non-cognate nucleotides (°). Fluorescence intensities were measured in relative fluorescence units.
Figure 7B:
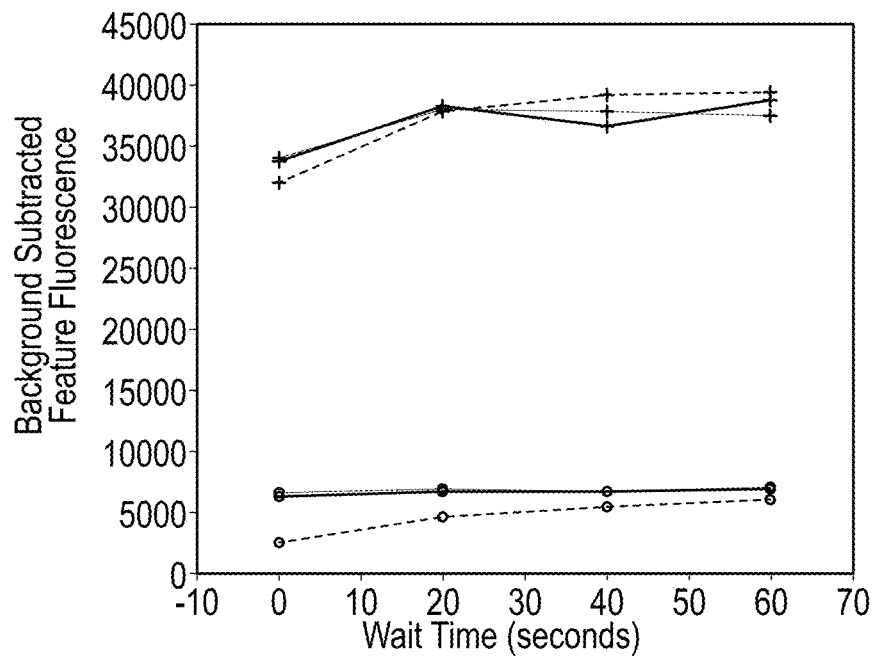

Results from these procedures indicated that an air wash could be used to reduce fluorescent background while maintaining fluorescent signal specific for ternary complex formation. In addition, the fluctuations in background fluorescence were reduced when using air as the imaging wash fluid or reagent. Reduced background fluctuations advantageously can improve sequencing accuracy and increase sequence read-length. FIGS. 6A (air wash) and 6B (aqueous buffer wash) show the fiftieth percentile of the fluorescent background signal for each of the four examined nucleotides per cycle. Inclusion of the air wash imaging step, where fluorescence data was captured following displacement of the examination buffer by air (i.e., as the wash step was taking place), reduced fluorescent background signal by about 80%-90% when compared to wash steps performed using a buffer in which polymerase and nucleotide were both soluble. FIGS. 7A and 7B, each presenting three replicates of testing using cognate and non-cognate nucleotides, show the ninetieth percentile of background-subtracted (e.g., "extracted") signal intensity. FIG. 7A presents results obtained using beads as features, and shows that extracted intensity for the cognate nucleotide was higher at all time points compared to signals measured using the non-cognate nucleotide. In this instance the ternary complex-specific signal decreased somewhat over the course of the wait period, but remained very stable for wait times of from 20-60 seconds. FIG. 7B presents results obtained using RCA products as the features, and also shows that extracted intensity for cognate nucleotide was higher at all time points compared to signals measured using the non-cognate nucleotide. In this instance, the ternary complex-specific signal remained very steady in air after displacing the polymerase- and nucleotide-containing examination buffer (i.e., during the air wash).

Taken together, these results demonstrated how an air wash step simultaneously reduced background fluorescence while stabilizing ternary complexes. Ternary complexes remained stable for at least 60 seconds, and discrimination between correct and incorrect nucleotides could be carried out using air to reduce background fluorescence by removal of non-complexed fluorescent reagent after ternary complex formation but prior to fluorescent imaging. Moreover, the difference between the correct and incorrect extracted intensities remained surprisingly stable over time without compromising the ability to strip polymerase and nucleotide from ternary complexes to prepare the flow cell for the next round of cycling reactions. Notably, substantially similar results were obtained when: (a) the primed template nucleic acid was blocked by the presence of a reversible terminator moiety, or (b) the primed template nucleic acid included a 3'-end that was available for polymerization, but was contained in a reaction mixture that included a non-catalytic metal ion that inhibits incorporation.

This invention has been described with reference to a number of specific examples and embodiments thereof. Of course, a number of different embodiments of the present invention will suggest themselves to those having ordinary skill in the art upon review of the foregoing detailed description. Thus, the true scope of the present invention is to be determined upon reference to the appended claims.

What is claimed is:

1. A method of identifying cognate nucleotides for each of a plurality of nucleic acid features, each feature comprising a primed template nucleic acid molecule, said method comprising the steps of:
    (a) preparing first stabilized ternary complexes at each of the plurality of nucleic acid features, each stabilized ternary complex comprising the primed template nucleic acid molecule at its respective nucleic acid feature, a reversible terminator nucleotide, and a polymerase;
    (b) contacting the first stabilized ternary complexes from step (a) with a reagent comprising a catalytic metal ion, at least one distinguishably labeled incorporable nucleotide, and a polymerase, to produce a reaction mixture,
    whereby the reversible terminator nucleotide incorporates into the primed template nucleic acid molecule to produce a blocked primed template nucleic acid molecule at each of the plurality of nucleic acid features, and
    whereby there forms at each of the plurality of nucleic acid features a second stabilized ternary complex comprising the blocked primed template nucleic acid molecule and one of the distinguishably labeled incorporable nucleotides; and
    (c) identifying cognate nucleotides for the primed template nucleic acid molecules at each of the plurality of nucleic acid features by detecting, in the reaction mixture, a label joined to the distinguishably labeled incorporable nucleotide of the second stabilized ternary complex.

2. The method of claim 1, wherein the polymerase of step (b) is the same type of polymerase as in step (a).

3. The method of claim 1, wherein the blocked primed template nucleic acid molecule of step (b) comprises a reversible terminator moiety at its 3' terminus, and wherein the method further comprises the step of cleaving the reversible terminator moiety from the blocked primed template nucleic acid molecule to produce a 3' terminus available for polymerization.

4. The method of claim 1, wherein the catalytic metal ion in the second reaction mixture is selected from the group consisting of $Mg^{2+}$ ion and $Mn^{2+}$ ion.

5. The method of claim 1, wherein the blocked primed template nucleic acid molecule of step (b) is immobilized to a solid support and wherein the solid support is contained within a flow cell.

6. The method of claim 5, wherein each of the plurality of nucleic acid features is contained within the flow cell.

7. The method of claim 1, wherein the label on the distinguishably labeled incorporable nucleotides is a distinguishable fluorescent label.

8. The method of claim 7, wherein the distinguishable fluorescent label does not comprise an intercalating dye that changes fluorescence after contacting DNA.

9. The method of claim 7, wherein the distinguishable fluorescent label is covalently attached to the incorporable nucleotide by a linker at a position on the nitrogenous base.

10. The method of claim 1, further comprising, after step (c), the steps of:
    (i) stripping the polymerase and the distinguishably labeled incorporable nucleotide of the second stabilized ternary complex from the blocked primed template nucleic acid molecule;
    (ii) cleaving a reversible terminator moiety from the blocked primed template nucleic acid molecule to create a deblocked primed template nucleic acid molecule comprising a 3' terminus available for polymerization; and
    (iii) incorporating a reversible terminator into the deblocked primed template nucleic acid molecule.

11. The method of claim 1, wherein the distinguishably labeled incorporable nucleotides in step (b) comprise at least two types of distinguishably labeled incorporable nucleotides, and wherein the detectable labels are different for each type of distinguishably labeled incorporable nucleotides.

12. The method of claim 1, wherein the distinguishably labeled incorporable nucleotides in step (b) comprises at least three types of distinguishably labeled incorporable nucleotides, and wherein the detectable labels are different for each type of distinguishably labeled incorporable nucleotides.

13. The method of claim 1, wherein the distinguishably labeled incorporable nucleotides in step (b) comprises four types of distinguishably labeled incorporable nucleotides, and wherein the detectable labels are different for each type of distinguishably labeled incorporable nucleotides.

14. The method of claim 1, wherein none of the distinguishably labeled incorporable nucleotides of step (c) includes a reversible terminator moiety.

15. The method of claim 1, wherein the reversible terminator nucleotide is unlabeled.

* * * * *